US008993738B2

(12) United States Patent
Prakash et al.

(10) Patent No.: US 8,993,738 B2
(45) Date of Patent: Mar. 31, 2015

(54) MODIFIED NUCLEOSIDES, ANALOGS THEREOF AND OLIGOMERIC COMPOUNDS PREPARED THEREFROM

(75) Inventors: Thazha P. Prakash, Carlsbad, CA (US); Punit P. Seth, Carlsbad, CA (US); Eric E. Swayze, Encinitas, CA (US)

(73) Assignee: Isis Pharmaceuticals, Inc., Carlsbad, CA (US)

(*) Notice: Subject to any disclaimer, the term of this patent is extended or adjusted under 35 U.S.C. 154(b) by 95 days.

(21) Appl. No.: 13/642,827

(22) PCT Filed: Apr. 26, 2011

(86) PCT No.: PCT/US2011/033968
§ 371 (c)(1),
(2), (4) Date: Dec. 17, 2012

(87) PCT Pub. No.: WO2011/139702
PCT Pub. Date: Nov. 10, 2011

(65) Prior Publication Data
US 2013/0084576 A1 Apr. 4, 2013

Related U.S. Application Data

(60) Provisional application No. 61/328,990, filed on Apr. 28, 2010, provisional application No. 61/393,100, filed on Oct. 14, 2010, provisional application No. 61/409,684, filed on Nov. 3, 2010.

(51) Int. Cl.
C07H 17/00 (2006.01)
C07H 21/04 (2006.01)
C12N 15/00 (2006.01)
C07H 19/067 (2006.01)
C07H 19/10 (2006.01)
C07H 19/167 (2006.01)
C07H 19/20 (2006.01)
C07H 21/00 (2006.01)
C07H 21/02 (2006.01)

(52) U.S. Cl.
CPC .............. *C07H 21/00* (2013.01); *C07H 19/067* (2013.01); *C07H 19/10* (2013.01); *C07H 19/167* (2013.01); *C07H 19/20* (2013.01); *C07H 21/02* (2013.01)
USPC ........... 536/4.1; 536/23.1; 536/24.5; 435/455

(58) Field of Classification Search
USPC .......................... 536/4.1, 23.1, 24.5; 435/455
See application file for complete search history.

(56) References Cited

U.S. PATENT DOCUMENTS

| 3,687,808 | A | 8/1972 | Merigan et al. |
| 4,415,732 | A | 11/1983 | Caruthers et al. |
| 4,458,066 | A | 7/1984 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,668,777 | A | 5/1987 | Caruthers et al. |
| 4,725,677 | A | 2/1988 | Koster et al. |
| 4,845,205 | A | 7/1989 | Huynh et al. |
| 4,973,679 | A | 11/1990 | Caruthers et al. |
| 4,981,957 | A | 1/1991 | Lebleu et al. |
| 5,013,830 | A | 5/1991 | Ohtsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| RE34,069 | E | 9/1992 | Koster et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,185,444 | A | 2/1993 | Summerton et al. |
| 5,188,897 | A | 2/1993 | Suhadolnik et al. |
| 5,194,599 | A | 3/1993 | Froehler |
| 5,214,134 | A | 5/1993 | Weis et al. |
| 5,216,141 | A | 6/1993 | Benner |
| 5,220,007 | A | 6/1993 | Pederson et al. |
| 5,235,033 | A | 8/1993 | Summerton et al. |
| 5,256,775 | A | 10/1993 | Froehler |

(Continued)

FOREIGN PATENT DOCUMENTS

| WO | WO 92/13869 | 8/1992 |
| WO | WO 94/02499 | 2/1994 |

(Continued)

OTHER PUBLICATIONS

Agrawal et al., *Protocols for Oligonucleotide Conjugates*, Humana Press; New Jersey, 1994, 26, Ch 3.
Altschul et al., "Basic Local Alignment Search Tool" J. Mol. Biol. (1990) 215:403-410.
Ausubel et al., Current Protocols in Molecular Biology, vol. 2, pp. 11.12.1-11.12.9, John Wiley & Sons, 1997.
Barany et al., "A New Amino Protecting Group Removable by Reduction. Chemistry of the Dithiasuccinoyl (Dts) Function" J. Am. Chem. Soc. (1977) 99:7363-7365.
Barany et al., "Kinetics and Mechanisms of the Thiolytic Removal of the Dithiasuccinoyl (Dts) Amino Protecting Group" J. Am. Chem. Soc. (1980) 102:3084-3095.

(Continued)

*Primary Examiner* — Jezia Riley
(74) *Attorney, Agent, or Firm* — Isis Pharmaceuticals, Inc. Patent Dept.; Casimir Jones, S.C.

(57) ABSTRACT

The present invention provides modified nucleosides, analogs thereof and oligomeric compounds prepared therefrom. More particularly, the present invention provides modified nucleosides and analogs thereof that are useful for incorporation at the terminus of an oligomeric compound. Such oligomeric compounds can also be included in a double stranded composition. In some embodiments, the oligomeric compounds provided herein are expected to hybridize to a portion of a target RNA resulting in loss of normal function of the target RNA.

19 Claims, No Drawings

(56) References Cited

U.S. PATENT DOCUMENTS

| | | |
|---|---|---|
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,712,378 A | 1/1998 | Wang |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,830,653 A | 11/1998 | Froehler et al. |
| 5,929,226 A | 7/1999 | Padmapriya et al. |
| 5,969,116 A | 10/1999 | Martin |
| 6,005,096 A | 12/1999 | Matteucci et al. |
| 6,426,220 B1 | 7/2002 | Bennett et al. |
| 6,600,032 B1 | 7/2003 | Manoharan et al. |
| 7,427,672 B2 | 9/2008 | Imanishi et al. |
| 2004/0171570 A1 | 9/2004 | Allerson et al. |
| 2006/0074035 A1 | 4/2006 | Hong et al. |
| 2011/0076681 A1 | 3/2011 | Waterhouse et al. |

FOREIGN PATENT DOCUMENTS

| | | |
|---|---|---|
| WO | WO 94/17093 | 8/1994 |
| WO | WO 94/22890 | 10/1994 |
| WO | WO 96/04295 | 2/1996 |
| WO | WO 98/00434 | 1/1998 |
| WO | WO 99/14226 | 3/1999 |
| WO | WO 01/14400 | 3/2001 |
| WO | WO 02/36743 | 5/2002 |
| WO | WO 2005/012371 | 12/2005 |
| WO | WO 2005/012372 | 12/2005 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |

OTHER PUBLICATIONS

Bass, "Double-stranded RNA as a template for gene silencing" Cell (2000) 101:235-238.

Beaucage et al., "The Functionalization of Oligonucleotides via Phosphoramidite Derivatives" Tetrahedron (1993) 49:1925-1963.

Beaucage et al., "The Synthesis of Specific Ribonucleotides and Unrelated Phosphorylated Biomolecules by the Phosphoramidite Method" Tetrahedron (1993) 49:10441-10488.

Beaucage et al., "Advances in the Synthesis of Oligonucleotides by the Phosphoramidite Approach" Tetrahedron (1992) 48:2223-2311.

Belikova et al., "Synthesis of Ribonucleosides and Diribonucleoside Phosphates Containing 2-Chloro-Ethylamine and Nitrogen Mustard Residues" Tet. Lett. (1967) 37:3557-3562.

Brazma et al., "Gene expression data analysis" FEBS Letters (2000) 480:17-24.

Carulli et al., "High Throughput Analysis of Differential Gene Expression" J. Cell. Biochem. Suppl. (1998) 30:286-296.

Celis et al., "Gene expression profiling: monitoring transcription and translation products using DNA microarrays and proteomics" FEBS Lett (2000) 480:2-16.

Chen et al., "Strand-specific 5'-O-methylation of siRNA duplexes controls guide strand selection and targeting specificity" RNA (2008) 14:263-274.

De Mesmaeker et al., "Amide-Modified Oligonucleotides with Preorganized Backbone and Furanose Rings: Highly Increased Thermodynamic Stability of the Duplexes Formed with their RNA and DNA Complements" Synlett (1997) 1287-1290.

Elbashir, "Duplexes of 21-nucleotide RNAs mediate RNA interference in cultured mammalian cells" Nature (2001) 411:494-498.

Elbashir, "RNA interference is mediated by 21- and 22-nucleotide RNAs" Genes & Devel. (2001) 15:188-200.

Englisch et al., "Chemically Modified Oligonucleotides as Probes and Inhibitors" Agnew Chem. Int. Ed. Engl. (1991) 30:613-629.

(56) References Cited

OTHER PUBLICATIONS

Eppacher et al., "Synthesis and Incorporation of C(5')-Ethynylated Uracil-Derived Phosphoramidites into RNA" Helvetica Chimica Acta (2004) 87(12):3004-3020.
Fire et al., "Potent and Specific Genetic Interference by Double-Stranded RNA in *Caenorhabditis elegans*" Nature (1998) 391:806-811.
Fuchs et al., "Identification of Differentially Expressed Genes by Mutually Subtracted RNA Fingerprinting" Anal. Biochem. (2000) 286:91-98.
Gait et al., "Application of chemically synthesized RNA" RNA: Protein Interactions (1998) 1-36.
Gallo et al., "2'-C-Methyluridine Phosphoramidite: A New Building Block for the Preparation of RNA Analogues Carrying the 2'-Dydroxyl Group" Tetrahedron (2001) 57: 5707-5713.
Going et al., "Molecular Pathology and Future Developments" Eur. J. Cancer (1999) 35:1895-1904.
Haringsma et al., "mRNA knockdown by single strand RNA is improved by chemical modifications" Nucleic Acids Research (2012) 40(9):4125-4136.
Jahn-Hofmann et al., "Efficient Solid Phase Synthesis of Cleavable Oligodeoxynucleotides Based on a Novel Strategy for the Synthesis of 5'-S-(4,4'-Dimethoxytrityl)-2'-deoxy-5'-thionucleoside Phosphoramidites" Helvetica Chimica Acta (2004) 87:2812-2828.
Jungblut et al., "Proteomics in human disease: Cancer, heart and infections diseases" Electrophoresis (1999) 20:2100-2110.
Jurecic et al., "Long-distance DD-PCR and cDNA microarrays" Curr. Opin. Microbiol. (2000) 3:316-321.
Kroschwitz, "Polynucleotides" Concise Encyclopedia of Polymer Science and Engineering (1990) John Wiley & Sons, NY pp. 858-859.
Larson et al., "Rapid DNA Fingerprinting of Pathogens by Flow Cytometry" Cytometry (2000) 41:203-208.
Larsson et al., "High-throughput protein expression of cDNA products as a tool in functional genomics" J. Biotech. (2000) 80:143-157.
Lima et al., "Binding and Cleavage Specificities of Human Argonatue2" Journal of Biological Chemistry (2009) 284(38):26017-26028.
Lima et al., "Single-Stranded siRNAs Activate RNAi in Animals" Cell (2012) 15:883-894.
Liu et al., "Uridylyl-(3'-5')-(5'-thiouridine). An Exceptionally Base-labile Di-ribonucleoside Phosphate Analogue" Tetrahedron Letters (1995) 36(19):3413-3416.
Madden et al., "Serial analysis of gene expression: from gene discovery to target identification" DDT (2000) 5:415-425.
Mag et al., "Synthesis and selective cleavage of oligodeoxyribonucleotldes containing non-chiral intemucieotlde phosphoramidate linkages" Nucleic Acids Res. (1989) 17(15):5973-5988.
Matulic-Ademic et al., "Synthesis and incorporation of 5'-amino- and 5'-mercapto-5'-deoxy-2'-O-methyl nucleosides into hammerhead ribozymes" Nucleosides & Nucleotides (1997) 16:1933-1950.
Mikhailov et al., "Substrate Properties of C'-Methylnucleoside and C'-Methyl-2'-Deoxynucleoside 5'Triphosphates in RNA and DNA Synthesis Reactions Catalysed by RNA and DNA Polymerases" Nucleosides &Nucleotides (1991) 10(1-3):339-343.
Miura et al., "Fluorometric determination of total mRNA with oligo(dT) immobilized on microtiter plates" Clin. Chem. (1996) 42:1758-1764.
Montgomery et al., "RNA as a target of double-stranded RNA-mediated genetic interference in *Caenorhabditis elegans*" Proc Natl. Acad. Sci. (1998) 95:15502-7.
Nishikura, "A Short Primer on RNAi: RNA-Directed RNA Polymerase Acts as a Key Catalyst" Cell (2001) 107:415-418.
Prashar et al., "READS: A Method for Display of 3'-End Fragment of Restriction Enzyme-Digested cDNAs for Analysis of Differential Gene Expression" Methods Enzymol. (1999) 303:258-272.

Saha et al., "5'-Me-DNA—A New Oligonucleotide Analog: Synthesis and Biochemical Properties" J. Org. Chem. (1995) 60:788-789.
Sanghvi, Chapter 15, Antisense Research and Applications, pp. 289-302, Crooke and Lebleu ed., CRC Press (1993).
Sutcliffe et al., "TOGA: An automated parsing technology for analyzing expression of nearly all genes" PNAS (2000) 97:1976-1981.
Swayze et al., "The Medicinal Chemistry of Oligonucleotides" Antisense Drug Technology: Principles, Strategies, and Applications, Chapter 6, pp. 143-182, Jul. 25, 2007, CRC Press.
Tabara et al., "RNAi in *C. elegans*: Soaking in the Genome Sequence" Science (1998) 282:430-431.
Tijsterman et al., "RNA hellcase MUT-14-dependent gene silencing triggered in *C. elegans* by short antisense RNAs" Science (2002) 295:694-7.
Timmons et al., "Ingestion of bacterially expressed dsRNAs can produce specific and potent genetic interference in *Caenorhabditis elegans*" Gene (2001) 263:103-112.
Timmons et al., "Specific Interference by Ingested dsRNA" Nature (1998) 395:854.
To, "Identification of Differential Gene Expression by High Throughput Analysis" Comb. Chem. High Throughput Screen (2000) 3:235-241.
Tuschl et al., "Targeted mRNA degradation by double-stranded RNA in vitro" Genes Dev. (1999) 13:3191-7.
Wang et al., "Biophysical and Biochemical Properties of Oligodeoxynucleotides Containing 4'-C- and 5'-C-Substituted Thymidines" Bioorg. Med. Chem. Lett. (1999) 9:885-890.
Wang et al., "Synthesis of Azole Nucleoside 5'-Monophosphate Mimics (P1Ms) and Their Inhibitory Properties of IMP Dehydrogenases" Nucleosides Nucleotides & Nucleic Acids (2004) 23(1&2):317-337.
Wu et al., "Functionalization of the Sugar Moiety of Oligoribonucleotides on Solid Support" Bioconjugate Chem. (1999) 10:921-924.
Wu et al., "Synthesis of 5'-C- and 2'-O-(Bromoalkyl)-Substituted Ribonucleoside Phosphoramidites for the Post-synthetic Functionalization of Oligonucleotides on Solid Support" Helvetica Chimica Acta (2000) 83:1127-1143.
Zamecnik et al., "Inhibition of Rous sarcoma virus replication and cell transformation by a specific oligodeoxynucleotide" PNAS (1978) 75:280-284.
Zhang et al., "PowerBLAST: A New Network BLAST Application for Interactive or Automated Sequence Analysis and Annotation" Genome Res. (1997) 7:649-656.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
European Search Report for application EP 12151431.9 dated Oct. 2, 2012.
International Search Report for application PCT/US2009/061913 dated Jul. 27, 2010.
International Search Report for application PCT/US2009/061959 dated Aug. 19, 2010.
Elbashir et al., "Functional anatomy of siRNAs for mediating efficient RNAi in Drosophila melanogaster embryo lysate" EMBO Journal (2001) 20(23):6877-6888.
Abbas et al., "Commercially Available 5'-DMT Phosphoramidites as Reagents for the Synthesis of Vinylphosphonate-Linked Oligonucleic Acids" Organic Letters (2001) 3(21):3365-3367.
Whittaker el al., "Stereoselective synthesis of highly functionalised P-stereogenic nucleosides via palladium-catalysed P-C cross-coupling reactions" Tetrahedron Letters (2008) 49:6984-6987.
Zhao, "Synthesis and preliminary biochemical studies with 5'-deoxy-5'-methylidyne phosphonate linked thymidine oligonucleotides" Tetrahedron Letters (1996) 37(35):6239-6242.
International Search Report for application PCT/US2011/033968 dated Mar. 11, 2013.
Bohringer et al., "Synheses of 5'-deoxy-5'-methylphosphonate Linked Thymidine Oligonucleotides" Tetrahedron Lett. (1993) 13(17):2723-2726.

SEQUENCE LISTING

<160> NUMBER OF SEQ ID NOS: 26

<210> SEQ ID NO 1
<211> LENGTH: 3160
<212> TYPE: DNA
<213> ORGANISM: Homo sapiens

<400> SEQUENCE: 1

```
cctcccctcg cccggcgcgg tcccgtccgc ctctcgctcg cctcccgcct cccctcggtc    60
ttccgaggcg cccgggctcc cggcgcggcg gcggaggggg cgggcaggcc ggcgggcggt   120
gatgtggcag gactctttat gcgctgcggc aggatacgcg ctcggcgctg ggacgcgact   180
gcgctcagtt ctctcctctc ggaagctgca gccatgatga agtttgaga gttgagccgc    240 tgtgaggcga ggccgggctc aggcgaggga gatgagagac ggcggcggcc gcggcccgga   300
gcccctctca gcgcctgtga gcagccgcgg gggcagcgcc ctcggggagc cggccggcct   360
gcggcggcgg cagcggcggc gtttctcgcc tcctcttcgt cttttctaac cgtgcagcct   420
cttcctcggc ttctcctgaa agggaaggtg gaagccgtgg gctcgggcgg gagccggctg   480
aggcgcggcg gcggcggcgg cggcacctcc cgctcctgga gcgggggga gaagcggcgg   540 cggcggcggc cgcggcggct gcagctccag ggaggggtc tgagtcgcct gtcaccattt    600
ccagggctgg gaacgccgga gagttggtct ctcccttct actgcctcca acacggcggc   660
ggcggcggcg gcacatccag ggacccgggc cggttttaaa cctcccgtcc gccgccgccg   720
caccccccgt ggcccgggct ccggaggccg ccggcggagg cagccgttcg gaggattatt   780
cgtcttctcc ccattccgct gccgccgctg ccaggcctct ggctgctgag gagaagcagg   840
cccagtcgct gcaaccatcc agcagccgcc gcagcagcca ttacccggct gcggtccaga   900
gccaagcggc ggcagagcga ggggcatcag ctaccgccaa gtccagagcc atttccatcc   960
tgcagaagaa gccccgccac cagcagcttc tgccatctct ctcctccttt tcttcagcc   1020 acaggctccc agacatgaca gccatcatca aagagatcgt tagcagaaac aaaaggagat  1080
atcaagagga tggattcgac ttagacttga cctatattta tccaaacatt attgctatgg  1140
gatttcctgc agaaagactt gaaggcgtat acaggaacaa tattgatgat gtagtaaggt  1200
ttttggattc aaagcataaa aaccattaca agatatacaa tctttgtgct gaaagacatt  1260
atgacaccgc caaatttaat tgcagagttg cacaatatcc ttttgaagac cataacccac  1320
cacagctaga acttatcaaa ccctttttgtg aagatcttga ccaatggcta agtgaagatg  1380
acaatcatgt tgcagcaatt cactgtaaag ctggaaaggg acgaactggt gtaatgatat  1440
gtgcatattt attacatcgg ggcaaatttt taaaggcaca agaggcccta gatttctatg  1500
gggaagtaag gaccagagac aaaaagggag taactattcc cagtcagagg cgctatgtgt  1560
```

```
attattatag ctacctgtta aagaatcatc tggattatag accagtggca ctgttgtttc    1620
acaagatgat gttttgaaact attccaatgt tcagtggcgg aacttgcaat cctcagtttg    1680
tggtctgcca gctaaaggtg aagatatatt cctccaattc aggacccaca cgacgggaag    1740
acaagttcat gtactttgag ttccctcagc cgttacctgt gtgtggtgat atcaaagtag    1800
agttcttcca caaacagaac aagatgctaa aaaaggacaa aatgtttcac ttttgggtaa    1860
atacattctt cataccagga ccagaggaaa cctcagaaaa agtagaaaat ggaagtctat    1920
gtgatcaaga aatcgatagc atttgcagta tagagcgtgc agataatgac aaggaatatc    1980
tagtacttac tttaacaaaa aatgatcttg acaaagcaaa taaagacaaa gccaaccgat    2040
acttttctcc aaattttaag gtgaagctgt acttcacaaa aacagtagag gagccgtcaa    2100
atccagaggc tagcagttca acttctgtaa caccagatgt tagtgacaat gaacctgatc    2160
attatagata ttctgacacc actgactctg atccagagaa tgaacctttt gatgaagatc    2220
agcatacaca aattacaaaa gtctgaattt ttttttatca agagggataa aacaccatga    2280
aaataaactt gaataaactg aaaatggacc ttttttttt taatggcaat aggacattgt    2340
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460 tatataccctt tttgtgtcaa aaggacattt aaaattcaat taggattaat aaagatggca    2520 cttttcccgtt ttattccagt tttataaaaa gtggagacag actgatgtgt atacgtagga    2580 atttttttcct tttgtgttct gtcaccaact gaagtggcta aagagctttg tgatatactg    2640
gttcacatcc taccccttttg cacttgtggc aacagataag tttgcagttg gctaagagag    2700
gtttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaa                          3160

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aatggctaag tgaagatgac aatcat                                            26

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tgcacatatc attacaccag ttcgt                                             25
```

```
<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4
ttgcagcaat tcactgtaaa gctggaaagg                                    30

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2-21
<223> OTHER INFORMATION: bases at these positions are RNA

<400> SEQUENCE: 5
tugucucugg uccuuacuua a                                             21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2-21
<223> OTHER INFORMATION: bases at these positions are RNA

<400> SEQUENCE: 6
tuaucuauaa ugaucaggua a                                             21

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2-21
<223> OTHER INFORMATION: bases at these positions are RNA

<400> SEQUENCE: 7
tgaacauugg aauaguuuca a                                             21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2-18, 20, 21
<223> OTHER INFORMATION: bases at these positions are RNA

<400> SEQUENCE: 8
tugucucugg uccuuacuta a                                             21

<210> SEQ ID NO 9
<211> LENGTH: 21
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2-14, 16-21
<223> OTHER INFORMATION: bases at these positions are RNA

<400> SEQUENCE: 9
tugucucugg uccutacuua a                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2-10, 12-21
<223> OTHER INFORMATION: bases at these positions are RNA

<400> SEQUENCE: 10
tugucucugg tccuuacuua a                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2-5, 7-21
<223> OTHER INFORMATION: bases at these positions are RNA

<400> SEQUENCE: 11
tuguctcugg uccuuacuua a                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2-20
<223> OTHER INFORMATION: bases at these positions are RNA

<400> SEQUENCE: 12
tugucucugg uccuuacuua t                                              21

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
ctgctagcct ctggatttga                                                20

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_feature
<222> LOCATION: 2-13, 15-18, 20, 21
<223> OTHER INFORMATION: bases at these positions are RNA

<400> SEQUENCE: 14
tuaucuauaa ugatcaggta a                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2-18, 20, 21
<223> OTHER INFORMATION: bases at these positions are RNA

<400> SEQUENCE: 15
tuaucuauaa ugaucaggta a                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2-5, 7-13, 15-21
<223> OTHER INFORMATION: bases at these positions are RNA

<400> SEQUENCE: 16
tuauctauaa ugatcaggua a                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2-10, 12-18, 20, 21
<223> OTHER INFORMATION: bases at these positions are RNA

<400> SEQUENCE: 17
tuaucuauaa tgaucaggta a                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2-21
<223> OTHER INFORMATION: bases at these positions are RNA

<400> SEQUENCE: 18
tuaagacuug agaugaucca a                                              21

<210> SEQ ID NO 19
<211> LENGTH: 20
<212> TYPE: DNA
<213> ORGANISM: Artificial Sequence
<220> FEATURE:
```

<223> OTHER INFORMATION: Synthetic oligonucleotide

<400> SEQUENCE: 19
gaccctggtg tacaccccaa                    20

<210> SEQ ID NO 20
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 20
cctggtgtac accc                          14

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1-19
<223> OTHER INFORMATION: bases at these positions are RNA

<400> SEQUENCE: 21
guaagacuug agaugaucct t                  21

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2-21
<223> OTHER INFORMATION: bases at these positions are RNA

<400> SEQUENCE: 22
tcuuaucacc uuuagcucua a                  21

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
tgtcatattc ctggatcctt                    20

<210> SEQ ID NO 24
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 24
gcgtttgctc ttcttcttgc gtttttt            27

<210> SEQ ID NO 25
<211> LENGTH: 21
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: misc_feature
<222> LOCATION: 1-19
<223> OTHER INFORMATION: bases at these positions are RNA

<400> SEQUENCE: 25
uugucucugg uccuuacuut t                                          21

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
gtacgcttgg tccctacatg                                            20
```

MODIFIED NUCLEOSIDES, ANALOGS THEREOF AND OLIGOMERIC COMPOUNDS PREPARED THEREFROM

CROSS REFERENCED TO RELATED APPLICATIONS

This application is a U.S. National Phase filing under 35 U.S.C. §371 claiming priority to International Serial No. PCT/US2011/033968 filed Apr. 26, 2011, which claims priority to U.S. Provisional Application 61/328,990, filed Apr. 28, 2010, and U.S. Provisional Application 61/393,100, filed Oct. 14, 2010, and U.S. Provisional Application 61/409,684, filed Nov. 3, 2010, each of which is incorporated herein by reference in its entirety.

STATEMENT OF GOVERNMENT SUPPORT

This invention was made with United States Government support under contract #5R44GM076793-03 awarded by the NIH. The United States Government has certain rights in the invention.

SEQUENCE LISTING

The present application is being filed along with a Sequence Listing in electronic format. The Sequence Listing is provided as a file entitled CHEM0067USASEQ.txt created on Sep. 25, 2012, which is 12 Kb in size. The information in the electronic format of the sequence listing is incorporated herein by reference in its entirety.

FIELD OF THE INVENTION

Provided herein are 5' modified nucleosides, analogs thereof and oligomeric compounds prepared therefrom. More particularly, 5' modified nucleosides and analogs thereof are provided that are useful for incorporation at one of the terminal positions of an oligomeric compound, preferably the 5' position. In certain embodiments, the oligomeric compounds provided herein are expected to have enhanced nuclease stability. In certain embodiments, the oligomeric compounds and compositions provided herein that incorporate one or more of these 5' modified nucleosides or analog thereof are expected to hybridize to a portion of a target RNA resulting in loss of normal function of the target RNA. The oligomeric compounds are also expected to be useful as primers and probes in diagnostic applications.

BACKGROUND OF THE INVENTION

Targeting disease-causing gene sequences was first suggested more than thirty years ago (Belikova et al., Tet. Lett., 1967, 37, 3557-3562), and antisense activity was demonstrated in cell culture more than a decade later (Zamecnik et al., Proc. Natl. Acad. Sci. U.S.A., 1978, 75, 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Generally, the principle behind antisense technology is that an antisense compound hybridizes to a target nucleic acid and modulates gene expression activities or function, such as transcription or translation. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels. An additional example of modulation of RNA target function by an occupancy-based mechanism is modulation of microRNA function. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense technology is an effective means for reducing the expression of one or more specific gene products and can therefore prove to be uniquely useful in a number of therapeutic, diagnostic, and research applications. Chemically modified nucleosides are routinely used for incorporation into antisense compounds to enhance one or more properties, such as nuclease resistance, pharmacokinetics or affinity for a target RNA. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

The synthesis of 5'-substituted DNA and RNA derivatives and their incorporation into oligomeric compounds has been reported in the literature (Saha et al., *J. Org. Chem.*, 1995, 60, 788-789; Wang et al., *Bioorganic & Medicinal Chemistry Letters*, 1999, 9, 885-890; and Mikhailov et al., *Nucleosides & Nucleotides*, 1991, 10(1-3), 339-343; Leonid et al., 1995, 14(3-5), 901-905; and Eppacher et al., *Helvetica Chimica Acta*, 2004, 87, 3004-3020). The 5'-substituted monomers have also been made as the monophosphate with modified bases (Wang et al., *Nucleosides Nucleotides & Nucleic Acids*, 2004, 23 (1 & 2), 317-337).

A genus of modified nucleosides including optional modification at a plurality of positions including the 5'-position and the 2'-position of the sugar ring and oligomeric compounds incorporating these modified nucleosides therein has been reported (see International Application Number: PCT/US94/02993, Published on Oct. 13, 1994 as WO 94/22890).

The synthesis of 5'-CH₂ substituted 2'-O-protected nucleosides and their incorporation into oligomers has been previously reported (see Wu et al., *Helvetica Chimica Acta,* 2000, 83, 1127-1143 and Wu et al. *Bioconjugate Chem.* 1999, 10, 921-924).

Amide linked nucleoside dimers have been prepared for incorporation into oligonucleotides wherein the 3' linked nucleoside in the dimer (5' to 3') comprises a 2'-OCH₃ and a 5'-(S)—CH₃ (Mesmaeker et al., *Synlett,* 1997, 1287-1290).

A genus of 2'-substituted 5'-CH₂ (or O) modified nucleosides and a discussion of incorporating them into oligonucleotides has been previously reported (see International Application Number: PCT/US92/01020, published on Feb. 7, 1992 as WO 92/13869).

The synthesis of modified 5'-methylene phosphonate monomers having 2'-substitution and their use to make modified antiviral dimers has been previously reported (see U.S. patent application Ser. No. 10/418,662, published on Apr. 6, 2006 as US 2006/0074035).

Various analogs of 5'-alkynylphosphonate ribonucleosides have been prepared and reported in the literature (see Meurillon et al., *Tetrahedron,* 2009, 65, 6039-6046 and *Nucleic Acids Symposium Series,* 2008, 52(1), 565-566; Lera et al., *Org. Lett.,* 2000, 2(24), 3873-3875).

The preparation of 5'-vinylphosphonate DNA and RNA monomers and their use to make dimeric compounds for oligonucleotide synthesis have been described. Their biochemical studies have also been discussed (see Whittaker et al., *Tet. Lett.,* 2008, 49, 6984-6987; Abbas et al., *Org. Lett.,* 2001, 3(21), 3365-3367; Bertram et al., *Biochemistry,* 2002, 41, 7725-7731; Zhao et al., *Tet. Lett.,* 1996, 37(35), 6239-6242 and Jung, et al., *Bioorg. Med Chem.,* 2000, 8, 2501-2509).

Various BNA's have been prepared and reported in the patent literature as well as in scientific literature, see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Wengel et al., PCT International Application WO 98-DK393 19980914; Singh et al., J. Org. Chem., 1998, 63, 10035-10039, the text of each is incorporated by reference herein, in their entirety. Examples of issued US patents and published applications include for example: U.S. Pat. Nos. 7,053,207, 6,770,748, 6,268,490 and 6,794,499 and published U.S. applications 20040219565, 20040014959, 20030207841, 20040192918, 20030224377, 20040143114 and 20030082807; the text of each is incorporated by reference herein, in their entirety.

The synthesis of various cyclohexitol nucleoside analogs has been reported in the literature, see for example: Verheggen et al., *J. Med. Chem.,* 1995, 38, 826-835; Altmann et al., *Chimia,* 1996, 50, 168-176; Herdewijn et al., *Bioorganic & Medicinal Chemistry Letters,* 1996, 6 (13), 1457-1460; Verheggen et al., *Nucleosides & Nucleotides,* 1996, 15(1-3), 325-335; Ostrowski et al., *J. Med. Chem.,* 1998, 41, 4343-4353; Allart et al., *Tetrahedron.,* 1999, 55, 6527-6546; Wouters et al., *Bioorganic & Medicinal Chemistry Letters,* 1999, 9, 1563-1566; Brown, et al., *Drug Development Res.,* 2000, 49, 253-259; published PCT application: WO 93/25565; WO 02/18406; and WO 05/049582; U.S. Pat. Nos. 5,314,893; 5,607,922; and 6,455,507.

Various cyclohexitol nucleoside analogs have been described as monomers and have also been incorporated into oligomeric compounds (see for example: Published PCT application, WO 93/25565, published Dec. 23, 1993; Augustyns et al. *Nucleic Acids Res.,* 1993, 21(20), 4670-4676; Verheggen et al., *J. Med Chem.,* 1993, 36, 2033-2040; Van Aerschot et al., *Angew. Chem. Int. Ed. Engl.,* 1995, 34(12), 1338-1339; Anderson et al., *Tetrahedron Letters,* 1996, 37(45), 8147-8150; Herdewijn et al., *Liebigs Ann.,* 1996, 1337-1348; De Bouvere et al., *Liebigs Ann./Recueil,* 1997, 1453-1461; 1513-1520; Hendrix et al., *Chem. Eur. J.,* 1997, 3(1), 110-120; Hendrix et al., *Chem. Eur. J.,* 1997, 3(9), 1513-1520; Hossain et al, *J. Org. Chem.,* 1998, 63, 1574-1582; Allart et al., *Chem. Eur. J.,* 1999, 5(8), 2424-2431; Boudou et al., *Nucleic Acids Res.,* 1999, 27(6), 1450-1456; Kozlov et al., *J. Am. Chem. Soc.,* 1999, 121, 1108-1109; Kozlov et al., *J. Am. Chem. Soc.,* 1999, 121, 2653-2656; Kozlov et al., *J. Am. Chem. Soc.,* 1999, 121, 5856-5859; Pochet et al., *Nucleosides & Nucleotides,* 1999, 18 (4&5), 1015-1017; Vastmans et al., *Collection Symposium Series,* 1999, 2, 156-160; Froeyen et al., *Helvetica Chimica Acta,* 2000, 83, 2153-2182; Kozlov et al., *Chem. Eur. J.,* 2000, 6(1), 151-155; Atkins et al., *Parmazie,* 2000, 55(8), 615-617; Lescrinier et al., *Chemistry & Biology,* 2000, 7, 719-731; Lescrinier et al., *Helvetica Chimica Acta,* 2000, 83, 1291-1310; Wang et al., *J. Am. Chem.,* 2000, 122, 8595-8602; US Patent Application US 2004/0033967; Published US Patent Application US 2008/0038745; Published and Issued U.S. Pat. No. 7,276,592). DNA analogs have also been reviewed in an article (see: Leumann, J. C, *Bioorganic & Medicinal Chemistry,* 2002, 10, 841-854) which included a general discussion of cyclohexitol nucleoside analogs (under the name: hexitol nucleic acid family).

Oligomeric compounds having phosphodiester linked hexitol nucleic acids (HNA, or 1,5-anhydrohexitol nucleic acids) have also been prepared for evaluation in cell assays. The different motifs that have been evaluated are fully modified wherein each monomer is a phosphodiester linked hexitol nucleic acid analog and gapped wherein each monomer in the 3' and 5' external regions of the oligomeric compound are each phosphodiester linked hexitol nucleic acid analogs and each monomer in the internal region is a phosphorothioate linked deoxyribonucleoside (see: Kang et al., *Nucleic Acids Research,* 2004, 32(14), 4411-4419; Vandermeeren et al., 2000, 55, 655-663; Flores et al., *Parasitol Res.,* 1999, 85, 864-866; and Hendrix et al., *Chem. Eur. J* 1997, 3(9), 1513-1520).

Oligomeric compounds having phosphodiester linked analogs having the 3'-OH group which are referred to in the art as ANA or D-altritol nucleic acids have been prepared and evaluated both structurally and in vitro (Allart et al., *Chem. Eur. J.,* 1999, 5(8), 2424-2431).

Chemically modified siRNA's having incorporated hexitol nucleotides (also referred to in the art as HNA nucleic acids) have been prepared and tested for silencing capacity (see: Published PCT application, WO 06/047842, published May 11, 2006.

Cyclohexenyl nucleic acids and analogs thereof have been reported in the scientific and patent literature as monomers as well as in oligomeric compounds, see for example: Robeyns et al., *J. Am. Chem. Soc.,* 2008, 130(6), 1979-1984; Horvath et al., *Tetrahedron Letters,* 2007, 48, 3621-3623; Nauwelaerts et al., *J. Am. Chem. Soc.,* 2007, 129(30), 9340-9348; Gu et al., *Nucleosides, Nucleotides & Nucleic Acids,* 2005, 24(5-7), 993-998; Nauwelaerts et al., *Nucleic Acids Research,* 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., *J. Org. Chem.,* 2003, 68, 4499-4505; Verbeure et al., Nucleic Acids Research, 2001, 29(24), 4941-4947; Wang et al., *J. Org. Chem.,* 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety.

The synthesis of various tetrahydropyran nucleoside analogs has been reported in the literature, see for example: Verheggen et al., *J. Med. Chem.*, 1995, 38, 826-835; Altmann et al., *Chimia*, 1996, 50, 168-176; Herdewijn et al., *Bioorganic & Medicinal Chemistry Letters*, 1996, 6 (13), 1457-1460; Verheggen et al., *Nucleosides & Nucleotides*, 1996, 15(1-3), 325-335; Ostrowski et al., *J. Med. Chem.*, 1998, 41, 4343-4353; Allart et al., *Tetrahedron.*, 1999, 55, 6527-6546; Wouters et al., *Bioorganic & Medicinal Chemistry Letters*, 1999, 9, 1563-1566; Brown, et al., *Drug Development Res.*, 2000, 49, 253-259; published PCT application: WO 93/25565; WO 02/18406; and WO 05/049582; U.S. Pat. Nos. 5,314,893; 5,607,922; and 6,455,507.

Various tetrahydropyran nucleoside analogs have been described as monomers and have also been incorporated into oligomeric compounds (see for example: Published PCT application, WO 93/25565, published Dec. 23, 1993; Augustyns et al. *Nucleic Acids Res.*, 1993, 21(20), 4670-4676; Verheggen et al., *J. Med. Chem.*, 1993, 36, 2033-2040; Van Aerschol et al., *Angew. Chem. Int. Ed. Engl.*, 1995, 34(12), 1338-1339; Anderson et al., *Tetrahedron Letters*, 1996, 37(45), 8147-8150; Herdewijn et al., *Liebigs Ann.*, 1996, 1337-1348; De Bouvere et al., *Liebigs Ann./Recueil*, 1997, 1453-1461; 1513-1520; Hendrix et al., *Chem. Eur. J.*, 1997, 3(1), 110-120; Hendrix et al., *Chem. Eur. J.*, 1997, 3(9), 1513-1520; Hossain et al, *J. Org. Chem.*, 1998, 63, 1574-1582; Allart et al., *Chem. Eur. J.*, 1999, 5(8), 2424-2431; Boudou et al., *Nucleic Acids Res.*, 1999, 27(6), 1450-1456; Kozlov et al., *J. Am. Chem. Soc.*, 1999, 121, 1108-1109; Kozlov et al., *J. Am. Chem. Soc.*, 1999, 121, 2653-2656; Kozlov et al., *J. Am. Chem. Soc.*, 1999, 121, 5856-5859; Pochet et al., *Nucleosides & Nucleotides*, 1999, 18 (4&5), 1015-1017; Vastmans et al., *Collection Symposium Series*, 1999, 2, 156-160; Froeyen et al., *Helvetica Chimica Acta*, 2000, 83, 2153-2182; Kozlov et al., *Chem. Eur.* 2000, 6(1), 151-155; Atkins et al., *Parmazie*, 2000, 55(8), 615-617; Lescrinier et al., *Chemistry & Biology*, 2000, 7, 719-731; Lescrinier et al., *Helvetica Chimica Acta*, 2000, 83, 1291-1310; Wang et al., *J. Am. Chem.*, 2000, 122, 8595-8602; US Patent Application US 2004/0033967; Published US Patent Application US 2008/0038745; Published and Issued U.S. Pat. No. 7,276,592). DNA analogs have also been reviewed in an article (see: Leumann, J. C, *Bioorganic & Medicinal Chemistry*, 2002, 10, 841-854) which included a general discussion of tetrahydropyran nucleoside analogs (under the name: hexitol nucleic acid family).

Oligomeric compounds having phosphodiester linked 3'-H tetrahydropyran nucleoside analogs (also referred to in the art as HNA—hexitol nucleic acids or 1,5-anhydrohexitol nucleic acids) have been prepared for evaluation in cell assays. The different motifs that have been evaluated are fully modified wherein each monomer is a phosphodiester linked 3'-H tetrahydropyran nucleoside analog and gapped wherein each monomer in the 3' and 5' external regions of the oligomeric compound are each phosphodiester linked 3'-H tetrahydropyran nucleoside analogs and each monomer in the internal region is a phosphorothioate linked deoxyribonucleoside (see: Kang et al., *Nucleic Acids Research*, 2004, 32(14), 4411-4419; Vandermeeren et al.,2000, 55, 655-663; Flores et al., *Parasitol Res.*, 1999, 85, 864-866; and Hendrix et al., *Chem. Eur. J.* 1997, 3(9), 1513-1520).

Oligomeric compounds having phosphodiester linked 3'-OH tetrahydropyran nucleoside analogs (also referred to in the art as ANA or D-altritol nucleic acids) have been prepared and evaluated both structurally and in vitro (Allart et al., *Chem. Eur. J.*, 1999, 5(8), 2424-2431).

Chemically modified siRNA's having incorporated hexitol nucleotides (also referred to in the art as HNA nucleic acids) have been prepared and tested for silencing capacity (see: Published PCT application, WO 06/047842, published May 11, 2006.

BRIEF SUMMARY OF THE INVENTION

Provided herein are 5' modified nucleosides, analogs thereof and oligomeric compounds prepared therefrom. More particularly, the 5' modified nucleosides and analogs thereof, provided herein, are linked to the terminus of an oligomeric compound, preferably at the 5' terminus. In certain embodiments, the oligomeric compounds provided herein are expected to have enhanced nuclease stability. In certain embodiments, the oligomeric compounds and compositions provided herein that incorporate one or more of the 5' modified nucleosides or an analog thereof are expected to hybridize to a portion of a target RNA resulting in loss of normal function of the target RNA. The oligomeric compounds are also expected to be useful as primers and probes in diagnostic applications.

The variables are defined individually in further detail herein. It is to be understood that the 5'-modified nucleosides, analogs thereof and oligomeric compounds provided herein include all combinations of the embodiments disclosed and variables defined herein.

In certain embodiments, compounds are provided having Formula Ic:

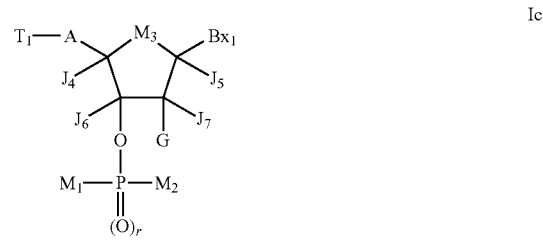

wherein:

T₁ is an optionally protected phosphorus moiety;

M₁ is H, OH or OR₁;

M₂ is OH, OR₁ or N(R₁)(R₂);

each R₁ and R₂ is, independently, C₁-C₆ alkyl or substituted C₁-C₆ alkyl;

r is 0 or 1;

A has one of the formulas:

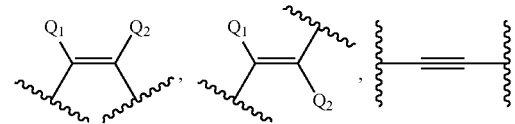

-continued

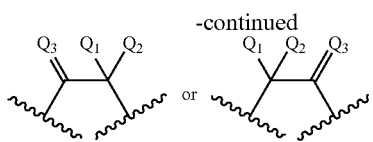

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{15})$, $C(R_{15})$=$C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$Bx_1$ is a heterocyclic base moiety;

or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})$=$C(R_{21})$, $C[$=$C(R_{20})(R_{21})]$ and $C($=$O)$ and the other two of $J_5$, $J_6$ and bare each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O—$[C(R_8)(R_9)]_n$—$[(C$=$O)_m$—$X_1]_j$—Z;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, =$NJ_1$, $SJ_1$, $N_3$, CN, $OC($=$X_2)J_1$, $OC($=$X_2)N(J_1)(J_2)$ and $C($=$X_2)N(J_1)(J_2)$;

$X_2$ is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

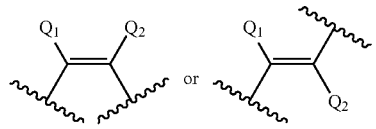

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

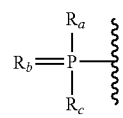

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $OCH(CH_3)_2$.

In certain embodiments, r is 0, $M_1$ is $O(CH_2)_2CN$ and $M_2$ is $N[CH(CH_3)_2]_2$.

In certain embodiments, G is halogen, $OCH_3$, $OCH_2F$, $OCHF_{52}$, $OCF_3$, $OCH_2CH_3$, $O(CH_2)_2F$, $OCH_2CHF_2$, $OCH_2CF_3$, $OCH_2$—CH=$CH_2$, $O(CH_2)_2$-$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})R_{11})$, $OCH_2C($=$O)$—$N(R_{10})(R_{11})$, $OCH_2C($=$O)$—$N(R_{12})$—$(CH_2)_2$—$N(R_{10})(R_{11})$ or $O(CH_2)_2$—$N(R_{12})$—$C($=$NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C($=$O)$—$N(H)CH_3$, $OCH_2C($=$O)$—$N(H)$—$(CH_2)_2$—$N(CH_3)_2$ or $OCH_2$—$N(H)$—$C($=$NH)NH_2$. In certain embodiments, G is F, $OCH_3$ or $O(CH_2)_2$—$OCH_3$. In certain embodiments, G is $O(CH_2)_2$—$OCH_3$.

In certain embodiments, the heterocyclic base moiety is a pyrimidine, substituted pyrimidine, purine or substituted purine. In certain embodiments, the heterocyclic base moiety is uracil, thymine, cytosine, 5-methylcytosine, adenine or guanine.

In certain embodiments, compounds are provided having the configuration of Formula Ie:

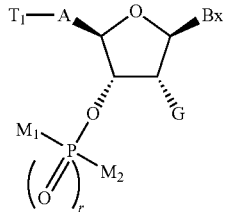

Ie wherein Bx is a heterocyclic base moiety selected from a pyrimidine, substituted pyrimidine, purine or substituted purine and the other variables are as described previously.

In certain embodiments, compounds of Formula Ie are provided wherein A has the formula:

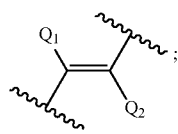

wherein $Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, compounds of Formula Ie are provided wherein $Q_1$ and $Q_2$ are each, independently, H, F, $CH_3$ or $OCH_3$. In certain embodiments, compounds of Formula Ie are provided wherein $T_1$ has the formula:

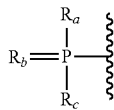

wherein;

$R_b$ is O; and $R_a$ and $R_c$ are each, independently, $OCH_3$, $OCH_2CH_3$ or $OCH(CH_3)_2$.

In certain embodiments, oligomeric compounds are provided having Formula IIc:

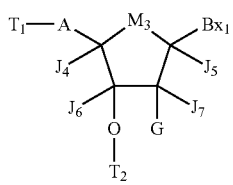

IIc wherein:

$T_1$ is an optionally protected phosphorus moiety;

$T_2$ is an internucleoside linking group linking the compound of Formula IIc to the oligomeric compound;

A has one of the formulas:

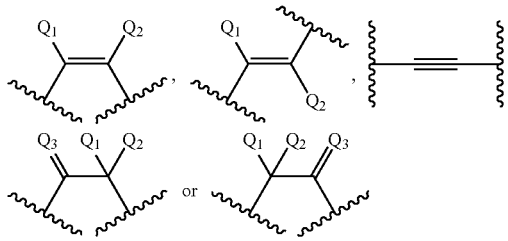

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{18})$, $C(R_{15})=C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$Bx_1$ is a heterocyclic base moiety;

or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O—$[C(R_8)(R_9)]_n$—$[(C=O)_m$—$X_1]_j$—Z;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, hand bare each H. In certain embodiments, $J_4$ forms a bridge with one of $J_5$ or $J_7$.

In certain embodiments, A has one of the formulas:

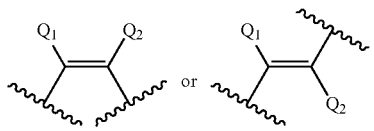

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

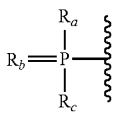

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})(R_{11})$, $OCH_2C(=O)$—$N(R_{10})(R_{11})$, $OCH_2C(=O)$—$N(R_{12})$—$(CH_2)_2$—$N(R_{10})(R_{11})$ or $O(CH_2)_2$—$N(R_{12})$—$C(=NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ or $OCH_2$—$N(H)$—$C(=NH)NH_2$. In certain embodiments, G is F, $OCH_3$ or $O(CH_2)_2$—$OCH_3$. In certain embodiments, G is $O(CH_2)_2$—$OCH_3$.

In certain embodiments, the heterocyclic base moiety is a pyrimidine, substituted pyrimidine, purine or substituted purine. In certain embodiments, the heterocyclic base moiety is uracil, thymine, cytosine, 5-methylcytosine, adenine or guanine.

In certain embodiments, oligomeric compounds are provided wherein each 5'-terminal compound having Formula IIc further has the configuration of Formula IId:

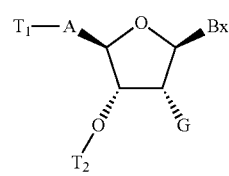

wherein Bx is a heterocyclic base moiety selected from a pyrimidine, substituted pyrimidine, purine or substituted purine.

In certain embodiments, A has the formula:

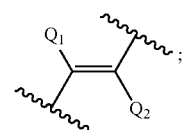

wherein $Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each, independently, H, F, $CH_3$ or $OCH_3$.

In certain embodiments, $T_1$ has the formula:

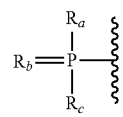

wherein;

$R_b$ is O; and $R_a$ and $R_c$ are each, independently, $OCH_3$, $OCH_2CH_3$ or $OCH(CH_3)_2$.

In certain embodiments, oligomeric compounds are provided wherein said 5'-terminal compound has Formula IIe:

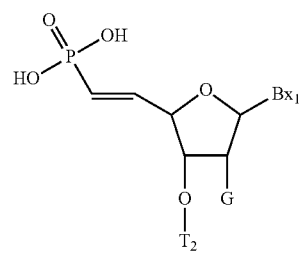

wherein:

Bx is uracil, thymine, cytosine, 5-methyl cytosine, adenine or guanine;

$T_2$ is a phosphorothioate internucleoside linking group linking the compound of Formula IIe to the oligomeric compound; and G is halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ or $OCH_2$—$N(H)$—$C(=NH)NH_2$.

In certain embodiments, oligomeric compounds are provided wherein said 5'-terminal compound has Formula IIe wherein G is F, $OCH_3$ or $O(CH_2)_2$—$OCH_3$.

In certain embodiments, oligomeric compounds are provided comprising linked monomeric subunits wherein each internucleoside linking group is, independently, a phosphodiester internucleoside linking group or a phosphorothioate internucleoside linking group. In certain embodiments, each internucleoside linking group is a phosphorothioate internucleoside linking group.

In certain embodiments, double stranded compositions are provided comprising:
a first oligomeric compound and a second oligomeric compound wherein the first oligomeric compound is complementary to the second oligomeric compound and the second oligomeric compound is complementary to a nucleic acid target;
at least one of the first and second oligomeric compounds is an oligomeric compound as provided herein; and
wherein said composition optionally comprises one or more 5' or 3' terminal groups.

In certain embodiments, methods of inhibiting gene expression are provided comprising contacting a cell with an oligomeric compound as provided herein or a double stranded composition as provided herein wherein said oligomeric compound alone or in a double stranded composition comprises from about 8 to about 40 monomeric subunits and is complementary to a target RNA. In certain embodiments, the cell is in an animal. In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function. In certain embodiments, the method further comprises detecting the levels of target RNA.

In certain embodiments, an in vitro method of inhibiting gene expression is provided comprising contacting one or more cells or a tissue with an oligomeric compound as provided herein or a double stranded composition as provided herein.

In certain embodiments, oligomeric compounds and double stranded compositions are provided for use in an in vivo method of inhibiting gene expression said method comprising contacting one or more cells, a tissue or an animal with an oligomeric compound as provided herein or a double stranded composition as provided herein.

In certain embodiments, an oligomeric compound or a double stranded composition as provided herein is provided for use in medical therapy.

In certain embodiments, an oligomeric compound for use alone or in a double stranded composition is provided comprising at-the 5'-position a compound having one of the formulas:

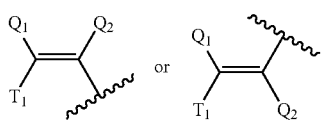

wherein:
$T_1$ is an optionally protected phosphorus moiety;
$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;
each $R_3$ and $R_4$ is, independently, H, $C_1$-$C_6$ alkyl, substituted $C_1$-$C_6$ alkyl or $C_1$-$C_6$ alkoxy;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;
$X_2$ is O, S or $NJ_3$;
each $J_1$, $J_2$ and $J_3$ is, independently, H or $C_1$-$C_6$ alkyl;
when j is 1 then Z is other than halogen or $N(E_2)(E_3)$; and
wherein said oligomeric compound or double stranded composition works through a ssRNAi or dsRNAi RISC based mechanism respectively and provides enhanced activity relative to an oligomeric compound that doesn't have the 5' modification. Such modification can be at the terminal 5' position of an oligomeric compound or at the equivalent 5' position for an oligomeric compounds comprising non-furanosyl monomers. Attachment of one of the vinyl groups as depicted above to monomers having non non-furanosyl rings is illustrated in the examples.

In certain embodiments, an oligomeric compound for use alone or in a double stranded composition is provided comprising at the 5'-position a compound having one of the formulas:

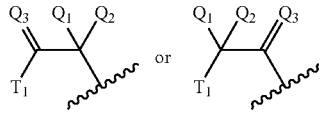

wherein:
$T_1$ is an optionally protected phosphorus moiety;
$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;
$Q_3$ is O, S, $N(R_5)$ or $C(R_6)(R_7)$;
each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;
each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;
$X_2$ is O, S or $NJ_3$;
each $J_1$, $J_2$ and $J_3$ is, independently, H or $C_1$-$C_6$ alkyl; and
when j is 1 then Z is other than halogen or $N(E_2)(E_3)$; and
wherein said oligomeric compound or double stranded composition works through a ssRNAi or dsRNAi RISC based mechanism respectively and provides enhanced activity relative to an oligomeric compound that doesn't have the 5' modification. Such modification can be at the terminal 5' position of an oligomeric compound or at the equivalent 5' position for an oligomeric compounds comprising non-furanosyl monomers.

In certain embodiments, an oligomeric compound for use alone or in a double stranded composition is provided comprising at the 5'-position a compound having the formula:

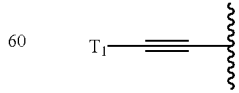

wherein:
$T_1$ is an optionally protected phosphorus moiety; and
wherein said oligomeric compound or double stranded composition works through a ssRNAi or dsRNAi RISC based mechanism respectively and provides enhanced activity relative to an oligomeric compound that doesn't have the 5' modification. Such modification can be at the terminal 5' position of an oligomeric compound or at the equivalent 5' position for an oligomeric compounds comprising non-furanosyl monomers.

In certain embodiments, the 5' modified nucleosides and the analogs thereof are each included in a compound of Formula Ic:

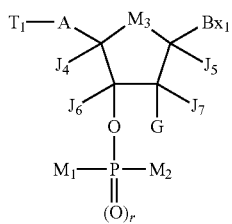

wherein:
$T_1$ is an optionally protected phosphorus moiety;
$M_1$ is H, OH or $OR_1$;
$M_2$ is OH, $OR_1$ or $N(R_1)(R_2)$;
each $R_1$ and $R_2$ is, independently, $C_1$-$C_6$ alkyl, substituted $C_1$-$C_6$ alkyl;
r is 0 or 1;
A has one of the formulas:

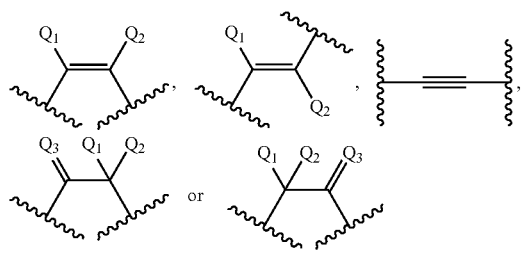

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;
$Q_3$ is O, S, $N(R_5)$ or $C(R_6)(R_7)$;
each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;
$M_3$ is O, S, $NR_{14}$, $C(R_{15})(R_{16})$, $C(R_{15})(R_{16})C(R_{17})(R_{18})$, $C(R_{15})=C(R_{17})$, $OC(R_{15})(R_{16})$ or $OC(R_{15})(Bx_2)$;
$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
one of $Bx_1$ and $Bx_2$ is a heterocyclic base moiety and the other of $Bx_1$ and $Bx_2$, if present, is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
or $J_4$ forms a bridge with either $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
G is H, OH, halogen or $O-[C(R_8)(R_9)]_n-[(C=O)_m-X_1]_j-Z$;
each $R_8$ and $R_9$ is, independently, H, halogen, $C_1$-$C_6$ alkyl or substituted $C_1$-$C_6$ alkyl;
$X_1$ is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;
$X_2$ is O, S or $NJ_3$;
each $J_1$, $J_2$ and $J_3$ is, independently, H or $C_1$-$C_6$ alkyl; and
when j is 1 then Z is other than halogen or $N(E_2)(E_3)$.

In certain embodiments, $M_3$ is O, $CH_2CH_2$, CH=CH, $OCH_2$ or $OC(H)(Bx_2)$ wherein $Bx_2$ is a heterocyclic base moiety.

In certain embodiments, $J_4$, $J_5$, $J_6$ and $J_7$ are each H.
In certain embodiments, A has the formula:

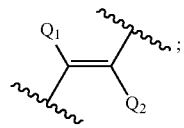

wherein $Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each, independently, H or halogen.

In certain embodiments, the 5' modified nucleosides each have Formula I:

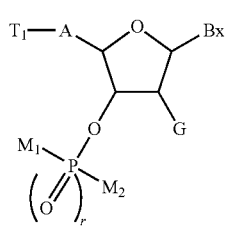

wherein:
Bx is a heterocyclic base moiety;
$T_1$ is an optionally protected phosphorus moiety;
$M_1$ is H, OH or $OR_1$;
$M_2$ is OH, $OR_1$ or $N(R_1)(R_2)$;
each $R_1$ and $R_2$ is, independently, alkyl or substituted alkyl;
r is 0 or 1;
A has one of the formulas:

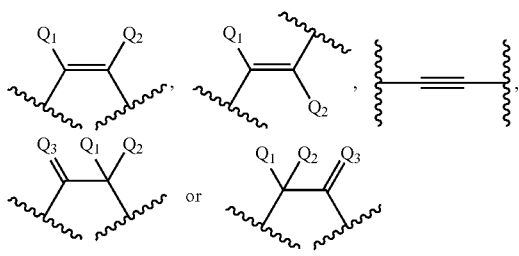

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;
$Q_3$ is O, S, $N(R_5)$ or $C(R_6)(R_7)$;
each $R_3$, $R_4$, $R_5$, $R_6$ and $R_7$ is, independently, H, $C_1$-$C_6$ alkyl, substituted $C_1$-$C_6$ alkyl or $C_1$-$C_6$ alkoxy;
G is H, OH, halogen or O—$[C(R_8)(R_9)]_n$—$[(C=O)_m$—$X]_j$—Z;
each $R_8$ and $R_9$ is, independently, H, halogen, $C_1$-$C_6$ alkyl or substituted $C_1$-$C_6$ alkyl;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl; n is from 1 to about 6;
m is 0 or 1;
j is 0 or 1;
each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;
L is O, S or $NJ_3$;
each $J_1$, $J_2$ and $J_3$ is, independently, H or $C_1$-$C_6$ alkyl; and when j is 1 then Z is other than halogen or $N(E_2)(E_3)$.
In certain embodiments, Bx is a pyrimidine, substituted pyrimidine, purine or substituted purine. In certain embodiments, Bx is uracil, 5-thiazolo-uracil, thymine, cytosine, 5-methylcytosine, 5-thiazolo-cytosine, adenine, guanine or 2,6-diaminopurine.
In certain embodiments, $T_1$ has the formula:

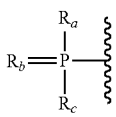

wherein:
$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and
$R_b$ is O or S.

In certain embodiments, $T_1$ has the formula:

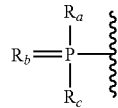

wherein:
$R_a$ and $R_c$ are each a protected hydroxyl; and
$R_b$ is O or S.
In certain embodiments, $T_1$ has the formula:

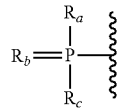

wherein:
$R_a$ and $R_c$ are each, independently, $OCH_3$, $OCH_2CH_3$ or $OCH(CH_3)_2$; and
$R_b$ is O.
In certain embodiments, r is 1, $M_1$ is H and $M_2$ is OH. In certain embodiments, r is 0, $M_1$ is $O(CH_2)_2CN$ and $M_2$ is $N[CH(CH_3)_2]_2$.
In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$-$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})(R_{11})$, $OCH_2C(=O)$—$N(R_{10})(R_{11})$, $OCH_2C(=O)$—$N(R_{12})$—$(CH_2)_2$—$N(R_{10})(R_{11})$ or $O(CH_2)_2$—$N(R_{12})$—$C(=NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ or $OCH_2$—$N(H)$—$C(=NH)NH_2$. In certain embodiments, G is F, $OCH_3$, $O(CH_2)_2$—$OCH_3$, $OCH_2C(=O)$—$N(H)CH_3$ or $OCH_2C(=O)$—$N(H)$—$(CH_2)_2$—$N(CH_3)_2$. In certain embodiments, G is $O(CH_2)_2$—$OCH_3$. In certain embodiments, G is F.
In certain embodiments, A has one of the formulas:

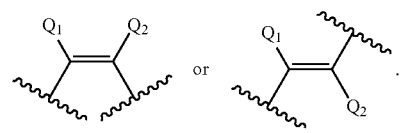

In certain embodiments, A has the formula:

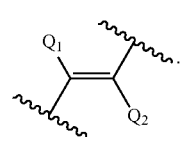

In certain embodiments, A has one of the formulas:

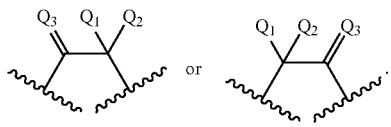

In certain embodiments, $Q_1$ and $Q_2$ are each H. In certain embodiments, $Q_1$ and $Q_2$ is H and the other of $Q_1$ and $Q_2$ is halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ is H and the other of $Q_1$ and $Q_2$ is F or $CH_3$. In certain embodiments, $Q_1$ and $Q_2$ are each, independently, F or $CH_3$. In certain embodiments, $Q_3$ is O. In certain embodiments, $Q_3$ is S. In certain embodiments, $Q_3$ is $N(R_5)$. In certain embodiments, $R_5$ is H. In certain embodiments, $R_5$ is $C_1$-$C_6$ alkyl or substituted $C_1$-$C_6$ alkyl. In certain embodiments, $R_5$ is $CH_3$. In certain embodiments, $Q_3$ is $C(R_6)(R_7)$. In certain embodiments, $R_6$ and $R_7$ are each H. In certain embodiments, one of $R_6$ and $R_7$ is H and the other of $R_6$ and $R_7$ is $C_1$-$C_6$ alkyl or substituted $C_1$-$C_6$ alkyl. In certain embodiments, one of $R_6$ and $R_7$ is H and the other of $R_6$ and $R_7$ is $CH_3$. In certain embodiments, $R_6$ and $R_7$ are each, independently, $C_1$-$C_6$ alkyl, substituted $C_1$-$C_6$ alkyl or $C_1$-$C_6$ alkoxy.

In certain embodiments, A has the formula:

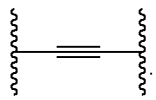

In certain embodiments, the 5' modified nucleosides each have Formula Ia:

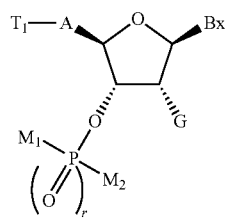

wherein:
Bx is a heterocyclic base moiety;
$T_1$ is an optionally protected phosphorus moiety;
$M_1$ is H, OH or $OR_1$;
$M_2$ is OH, $OR_1$ or $N(R_1)(R_2)$;
each $R_1$ and $R_2$ is, independently, alkyl or substituted alkyl;
r is 0 or 1;
A has one of the formulas:

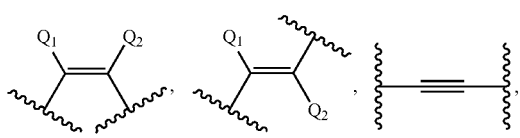

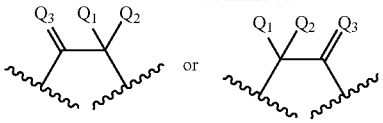

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;
$Q_3$ is O, S, $N(R_5)$ or $C(R_6)(R_7)$;
each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;
G is H, OH, halogen or O—$[C(R_8)(R_9)]_n$—$[(C=O)_m$—$X]_j$—Z;
each $R_8$ and $R_9$ is, independently, H, halogen, $C_1$-$C_6$ alkyl or substituted $C_1$-$C_6$ alkyl;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;
L is O, S or $NJ_3$;
each $J_1$, $J_2$ and $J_3$ is, independently, H or $C_1$-$C_6$ alkyl; and
when j is 1 then Z is other than halogen or $N(E_2)(E_3)$.

In certain embodiments, the 5' modified nucleosides each have Formula Ib:

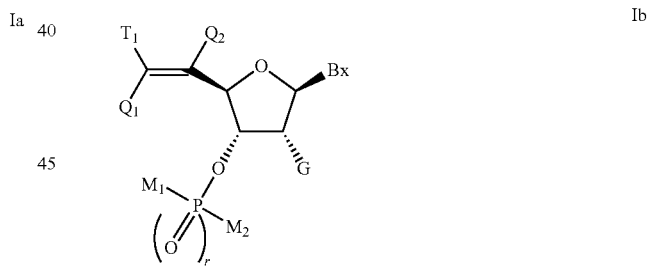

wherein:
Bx is a heterocyclic base moiety;
$T_1$ is an optionally protected phosphorus moiety;
$M_1$ is H, OH or $OR_1$;
$M_2$ is OH, $OR_1$ or $N(R_1)(R_2)$;
each $R_1$ and $R_2$ is, independently, alkyl or substituted alkyl;
r is 0 or 1;
$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;
each $R_3$ and $R_4$ is, independently, H, $C_1$-$C_6$ alkyl, substituted $C_1$-$C_6$ alkyl or $C_1$-$C_6$ alkoxy;
G is H, OH, halogen or O—$[C(R_8)(R_9)]_n$—$[(C=O)_m$—$X]_j$—Z;
each $R_8$ and $R_9$ is, independently, H, halogen, $C_1$-$C_6$ alkyl or substituted $C_1$-$C_6$ alkyl;

X is O, S or N($E_1$);

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl; n is from 1 to about 6;

m is 0 or 1;

j is 0 or 1;

each substituted group comprises one or more optionally protected substituent groups independently selected from halogen, $OJ_1$, N($J_1$)($J_2$), $NJ_1$, $SJ_1$, $N_3$, CN, OC(=L)$J_1$, OC(=L)N($J_1$)($J_2$) and C(=L)N($J_1$)($J_2$);

L is O, S or $NJ_3$;

each $J_1$, $J_2$ and $J_3$ is, independently, H or $C_1$-$C_6$ alkyl; and when j is 1 then Z is other than halogen or N($E_2$)($E_3$).

In certain embodiments, the 5' modified nucleosides each have Formula Ib:

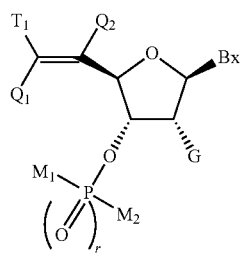

Ib wherein:

Bx is a heterocyclic base moiety;

$T_1$ is an optionally protected phosphorus moiety;

$M_1$ is O($CH_2$)$_2$CN;

$M_2$ is N[(CH($CH_3$)$_2$]$_2$;

r is 0;

$Q_1$ and $Q_2$ are each H;

G is halogen or O—[C($R_8$)($R_9$)]$_n$—[(C=O)$_m$—X]$_j$—Z;

each $R_8$ and $R_9$ is, independently, H, halogen, $C_1$-$C_6$ alkyl or substituted $C_1$-$C_6$ alkyl;

X is O, S or N($E_1$);

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, N($J_1$)($J_2$), =$NJ_1$, $SJ_1$, $N_3$, CN, OC(=L)$J_1$, OC(=L)N($J_1$)($J_2$) and C(=L)N($J_1$)($J_2$);

L is O, S or $NJ_3$;

each $J_1$, $J_2$ and $J_3$ is, independently, H or $C_1$-$C_6$ alkyl; and when j is 1 then Z is other than halogen or N($E_2$)($E_3$).

In certain embodiments, the 5' modified nucleosides each have Formula Ib:

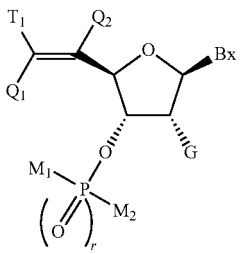

Ib wherein:

Bx is a heterocyclic base moiety;

$T_1$ is an optionally protected phosphorus moiety;

$M_1$ is O($CH_2$)$_2$CN;

$M_2$ is N[($CH_3$)$_2$]$_2$;

r is 0;

$Q_1$ and $Q_2$ are each H;

G is O($CH_2$)$_2$OCH$_3$.

each substituted group comprises one or more optionally protected substituent groups independently selected from halogen, $OJ_1$, N($J_1$)($J_2$), =$NJ_1$, $SJ_1$, $N_3$, CN, OC(=L)$J_1$, OC(=L)N($J_1$)($J_2$) and C(=L)N($J_1$)($J_2$);

L is O, S or $NJ_3$;

each $J_1$, $J_2$ and $J_3$ is, independently, H or $C_1$-$C_6$ alkyl; and when j is 1 then Z is other than halogen or N($E_2$)($E_3$).

In certain embodiments, oligomeric compounds are provided comprising a compound having Formula IIc:

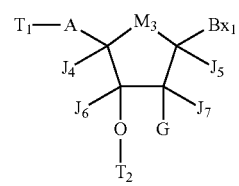

IIc wherein:

$T_1$ is an optionally protected phosphorus moiety;

$T_2$ is an internucleoside linking group linking the compound of Formula IIc to the oligomeric compound;

$M_1$ is H, OH or $OR_1$;

$M_2$ is OH, $OR_1$ or N($R_1$)($R_2$);

each $R_1$ and $R_2$ is, independently, $C_1$-$C_6$ alkyl, substituted $C_1$-$C_6$ alkyl;

r is 0 or 1;

A has one of the formulas:

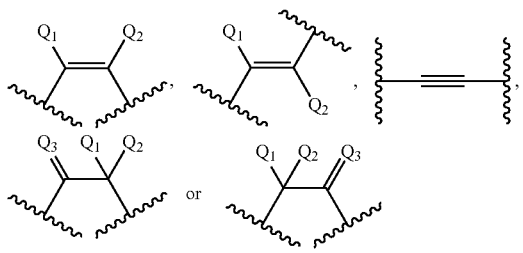

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or N($R_3$)($R_4$);

$Q_3$ is O, S, $N(R_5)$ or $C(R_6)(R_7)$;

each $R_3, R_4, R_5, R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{13})$, $C(R_{15})=C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}, R_{16}, R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

one of $Bx_1$ and $Bx_2$ is a heterocyclic base moiety and the other of $Bx_1$ and $Bx_2$, if present, is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4, J_5, J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with either $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5, J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}, R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O—$[C(R_8)(R_9)]_n$—$[(C=O)_m$—$X_1]_j$—Z;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1, E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1, J_2$ and $J_3$ is, independently, H or $C_1$-$C_6$ alkyl; and when j is 1 then Z is other than halogen or $N(E_2)(E_3)$.

In certain embodiments, oligomeric compounds are provided having Formula IIc wherein $M_3$ is O, $CH_2CH_2$, CH=CH, $OCH_2$ or $OC(H)(Bx_2)$ wherein $Bx_2$ is a heterocyclic base moiety.

In certain embodiments, oligomeric compounds are provided having Formula IIc wherein $J_4, J_5, J_6$ and $J_7$ are each H.

In certain embodiments, oligomeric compounds are provided comprising a compound having Formula IIc wherein A has the formula:

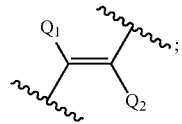

wherein $Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy.

In certain embodiments, oligomeric compounds are provided comprising a compound having Formula IIc wherein $Q_1$ and $Q_2$ are each, independently, H or halogen.

In certain embodiments, oligomeric compounds are provided comprising a 5'-terminal compound having Formula II:

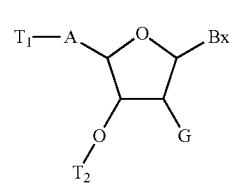

II wherein:

Bx is a heterocyclic base moiety;

$T_1$ is an optionally protected phosphorus moiety;

$T_2$ is an internucleoside linking group linking the compound of Formula II to the oligomeric compound;

A has one of the formulas:

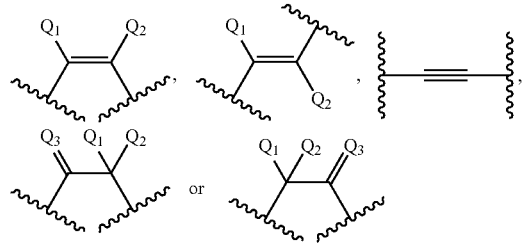

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

$Q_3$ is O, S, $N(R_5)$ or $C(R_6)(R_7)$;

each $R_3, R_4, R_5, R_6$ and $R_7$ is, independently, H, $C_1$-$C_6$ alkyl, substituted $C_1$-$C_6$ alkyl or $C_1$-$C_6$ alkoxy;

G is H, OH, halogen or O—$[C(R_8)(R_9)]_n$—$[(C=O)_m$—$X]_j$—Z;

each $R_8$ and $R_9$ is, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1, E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)J_2$ and $C(=L)N(J_1)(J_2)$;

L is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, oligomeric compounds are provided comprising a compound having Formula II wherein Bx is a pyrimidine, substituted pyrimidine, purine or substituted purine. In certain embodiments, oligomeric compounds are provided comprising a compound having Formula II wherein Bx is uracil, 5-thiazolo-uracil, thymine, cytosine, 5-methylcytosine, 5-thiazolo-cytosine, adenine, guanine or 2,6-diaminopurine.

In certain embodiments, oligomeric compounds are provided comprising a compound having Formula II or Formula IIc wherein $T_1$ has the formula:

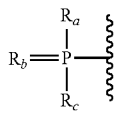

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S.

In certain embodiments, oligomeric compounds are provided comprising a compound having Formula II or Formula IIc wherein $T_1$ has the formula:

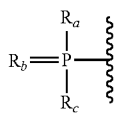

wherein:

$R_a$ and $R_c$ are each a protected hydroxyl; and $R_b$ is O or S.

In certain embodiments, oligomeric compounds are provided comprising a compound having Formula II or Formula IIc wherein $T_1$ has the formula:

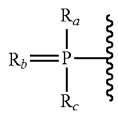

wherein:

$R_a$ and $R_c$ are each, independently, $OCH_3$, $OCH_2CH_3$ or $OCH(CH_3)_2$; and $R_b$ is O.

In certain embodiments, oligomeric compounds are provided comprising a compound having Formula II or Formula IIc wherein G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2—CH=CH_2$, $O(CH_2)_2—OCH_3$, $O(CH_2)_2—SCH_3$, $O(CH_2)_2—OCF_3$, $O(CH_2)_3—N(R_{10})R_{11}$, $O(CH_2)_2—ON(R_{10})(R_{11})$, $O(CH_2)_2—O(CH_2)_2—N(R_{10})(R_{11})$, $OCH_2C(=O)—N(R_{10})(R_{11})$, $OCH_2C(=O)—N(R_{12})—(CH_2)_2—N(R_{10})(R_{11})$ or $O(CH_2)_2—N(R_{12})—C(=NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, oligomeric compounds are provided comprising a compound having Formula II or Formula IIe wherein G is halogen, $OCH_3$, $OCF_3$, $OCH_2CH_3$, $OCH_2CF_3$, $OCH_2—CH=CH_2$, $O(CH_2)_2—OCH_3$, $O(CH_2)_2—O(CH_2)_2—N(CH_3)_2$, $OCH_2C(=O)—N(H)CH_3$, $OCH_2C(=O)—N(H)—(CH_2)_2—N(CH_3)_2$ or $OCH_2—N(H)—C(=NH)NH_2$. In certain embodiments, oligomeric compounds are provided comprising a compound having Formula II or Formula IIc wherein G is F, $OCH_3$, $O(CH_2)_2—OCH_3$, $OCH_2C(=O)—N(H)CH_3$ or $OCH_2C(=O)—N(H)—(CH_2)_2—N(CH_3)_2$. In certain embodiments, oligomeric compounds are provided comprising a compound having Formula II or Formula IIc wherein G is $O(CH_2)_2—OCH_3$. In certain embodiments, oligomeric compounds are provided comprising a compound having Formula II or Formula IIe wherein G is F.

In certain embodiments, oligomeric compounds are provided comprising a compound having Formula II or Formula IIc wherein A has one of the formulas:

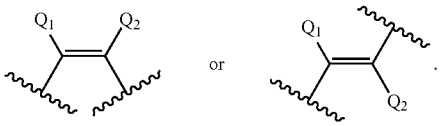

In certain embodiments, oligomeric compounds are provided comprising a compound having Formula II or Formula IIe wherein A has the formula:

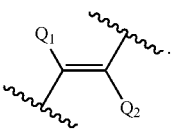

In certain embodiments, oligomeric compounds are provided comprising a compound having Formula II or Formula IIc wherein A has one of the formulas:

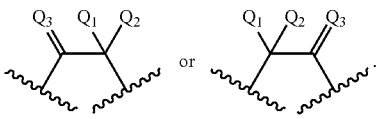

In certain embodiments, oligomeric compounds are provided comprising a compound having Formula II or Formula IIe wherein $Q_1$ and $Q_2$ are each H. In certain embodiments, oligomeric compounds are provided comprising a compound having Formula II or Formula IIe wherein one of $Q_1$ and $Q_2$ is H and the other of $Q_1$ and $Q_2$ is halogen, $C_1$-$C_6$ alkyl, substituted $C_1$-$C_6$ alkyl, $C_1$-$C_6$ alkoxy or substituted $C_1$-$C_6$ alkoxy. In certain embodiments, oligomeric compounds are provided comprising a compound having Formula II or Formula IIe wherein one of $Q_1$ and $Q_2$ is H and the other of $Q_1$ and $Q_2$ is F or $CH_3$. In certain embodiments, oligomeric compounds are provided comprising a compound having Formula II or Formula IIe wherein $Q_1$ and $Q_2$ are each, independently, F or $CH_3$. In certain embodiments, oligomeric compounds are provided comprising a compound having Formula II or Formula IIc wherein $Q_3$ is O. In certain embodiments, oligomeric compounds are provided comprising a compound having Formula II or Formula IIc wherein $Q_3$ is S. In certain embodiments, oligomeric compounds are provided comprising a compound having Formula II or Formula IIc wherein $Q_3$ is $N(R_5)$.

In certain embodiments, oligomeric compounds are provided comprising a compound having Formula II or Formula IIc wherein Q is $N(R_5)$ and $R_5$ is H. In certain embodiments, oligomeric compounds are provided comprising a compound having Formula II or Formula IIc wherein $Q_3$ is $N(R_5)$ and $R_5$ is $C_1$-$C_6$ alkyl or substituted $C_1$-$C_6$ alkyl. In certain embodiments, oligomeric compounds are provided comprising a compound having Formula II or Formula IIc wherein Q is $N(R_5)$ and $R_5$ is $CH_3$.

In certain embodiments, oligomeric compounds are provided comprising a compound having Formula II or Formula IIc wherein $Q_3$ is $C(R_6)(R_7)$.

In certain embodiments, oligomeric compounds are provided comprising a compound having Formula II or Formula IIc wherein $Q_3$ is $C(R_6)(R_7)$ and $R_6$ and $R_7$ are each H. In certain embodiments, oligomeric compounds are provided comprising a compound having Formula II or Formula IIc wherein $Q_3$ is $C(R_6)(R_7)$ and one of $R_6$ and $R_7$ is H and the other of $R_6$ and $R_7$ is $C_1$-$C_6$ alkyl or substituted $C_1$-$C_6$ alkyl. In certain embodiments, oligomeric compounds are provided comprising a compound having Formula II or Formula IIc wherein Q is $C(R_6)(R_7)$ and one of $R_6$ and $R_7$ is H and the other of $R_6$ and $R_7$ is $CH_3$. In certain embodiments, oligomeric compounds are provided comprising a compound having Formula II or Formula IIc wherein Q is $C(R_6)(R_7)$ and $R_6$ and $R_7$ are each, independently, $C_1$-$C_6$ alkyl, substituted $C_1$-$C_6$ alkyl or $C_1$-$C_6$ alkoxy.

In certain embodiments, oligomeric compounds are provided comprising a compound having Formula II or Formula IIc wherein A has the formula:

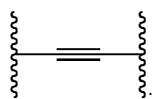

In certain embodiments, oligomeric compounds are provided comprising a compound having Formula IIa:

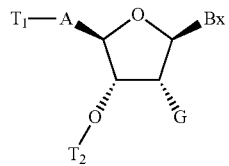

wherein:

Bx is a heterocyclic base moiety;

$T_1$ is an optionally protected phosphorus moiety;

$T_2$ is an internucleoside linking group linking the compound of Formula II to the remainder of the oligomeric compound;

A has one of the formulas:

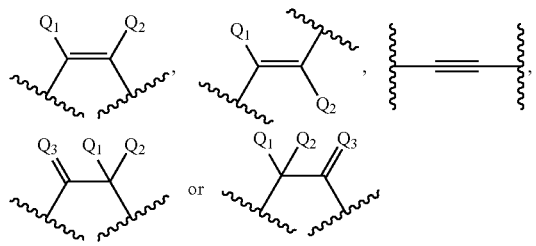

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

G is H, OH, halogen or O—$[C(R_8)(R_9)]_n$—$[(C=O)_m$—$X]_j$—Z;

each $R_8$ and $R_9$ is, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, oligomeric compounds are provided comprising a compound having Formula IIb:

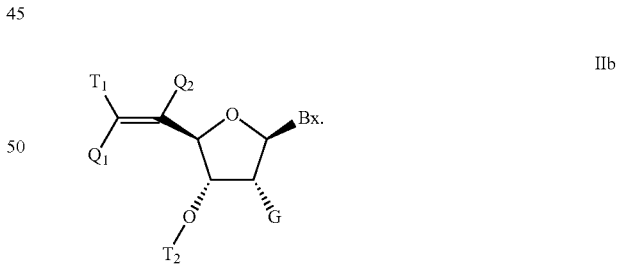

In certain embodiments, oligomeric compounds are provided comprising a compound having Formula IIb wherein $Q_1$ and $Q_2$ are each H.

In certain embodiments, oligomeric compounds are provided comprising a compound having Formula IIa or IIb wherein G is $O(CH_2)_2OCH_3$.

In certain embodiments, oligomeric compounds are provided wherein each internucleoside linking group is, independently, a phosphodiester internucleoside linking group or a phosphorothioate internucleoside linking group. In certain embodiments, oligomeric compounds are provided wherein essentially each inter-nucleoside linking group is a phosphorothioate internucleoside linking group.

In certain embodiments, double stranded compositions are provided each comprising:

a first oligomeric compound and a second oligomeric compound wherein the first oligomeric compound is complementary to the second oligomeric compound and the second oligomeric compound is complementary to a nucleic acid target;

at least one of the first and second oligomeric compounds is an oligomeric compound comprising a 5' terminal compound having Formula II, IIa IIb or IIc; and wherein said composition optionally comprises one or more 5' or 3' terminal groups.

In certain embodiments, methods of inhibiting gene expression are provided that comprise contacting a cell with an oligomeric compound comprising a 5' terminal compound having Formula II, IIa IIb or IIc or double stranded composition comprising at least one 5' terminal compound having Formula II, IIa IIb or IIc wherein the oligomeric compound and the first and second oligomeric compounds in the double stranded composition each comprise from about 8 to about 40 monomeric subunits and the oligomeric compound or one of the first and second oligomeric compounds in the double stranded composition is complementary to a target RNA. In certain embodiments, the cell is in an animal. In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function. In certain embodiments, the methods further comprise detecting the levels of target RNA.

In certain embodiments, methods of inhibiting gene expression are provided comprising contacting one or more cells or a tissue with an oligomeric compound comprising a 5' terminal compound having Formula II, IIa IIb or IIc or double stranded composition comprising at least one 5' terminal compound having Formula II, IIa IIb or IIc.

In certain embodiments, oligomeric compounds comprising a 5' terminal compound having Formula II, IIa IIb or IIc or double stranded composition comprising at least one 5' terminal compound having Formula II, IIa IIb or IIc are provided for use in an in vivo method of inhibiting gene expression the method comprises contacting one or more cells, a tissue or an animal with an oligomeric compound comprising a 5' terminal compound having Formula II, IIa IIb or IIc or double stranded composition comprising at least one 5' terminal compound having Formula II, IIa IIb or IIc.

In certain embodiments, oligomeric compounds comprising a 5' terminal compound having Formula II, IIa IIb or IIc or double stranded composition comprising at least one 5' terminal compound having Formula II, IIa IIb or IIc are provided for use in medical therapy.

In certain embodiments, the remainder of the oligomeric compound other than the 5' modified nucleoside or analog thereof, will have one or more modifications thereto. Such modifications include sugar modification or replacement with a sugar surrogate, base modifications, other 3' and 5' terminal groups (double stranded compositions, which include at least one of the oligomeric compounds as described herein, inherently have two 5' ends), internucleoside linkage modifications and motifs. Such modifications are described herein and many of which are known to the art skilled. All such modifications are amenable to the oligomeric compounds and double stranded compositions disclosed herein.

In certain such embodiments, the remainder of the oligomeric compound comprises at least one modified nucleoside.

In certain embodiments, the oligomeric compound comprises a modified base. In certain embodiments, the oligomeric compound comprises a sugar surrogate. In certain such embodiments, the sugar surrogate is a tetrahydropyran. In certain embodiments, the tetrahydropyran is F-HNA.

In certain embodiments, the remainder of the oligomeric compound comprises at least one nucleoside comprising a modified sugar. In certain embodiments, the at least one modified nucleoside comprising a modified sugar is selected from a bicyclic nucleoside and a 2'-modified nucleoside. In certain embodiments, the at least one modified nucleoside is a bicyclic nucleoside. In certain embodiments, the bicyclic nucleoside is a (4'-$CH_2$—O-2') BNA nucleoside. In certain embodiments, the bicyclic nucleoside is a (4'-$(CH_2)_2$—O-2') BNA nucleoside. In certain embodiments, the bicyclic nucleoside is a (4'-$C(CH_3)H$—O-2') BNA nucleoside. In certain embodiments, the at least one modified nucleoside is a 2'-modifed nucleoside. In certain embodiments, the at least one 2'-modified nucleoside is selected from a 2'-F nucleoside, a 2'-$OCH_3$ nucleoside, and a 2'-$O(CH_2)_2OCH_3$ nucleoside. In certain embodiments, the at least one 2'-modified nucleoside is a 2'-F nucleoside. In certain embodiments, the at least one 2'-modified nucleoside is a 2'-$OCH_3$ nucleoside. In certain embodiments, the at least one 2'-modified nucleoside is a 2'-$O(CH_2)_2OCH_3$ nucleoside.

In certain embodiments, the remainder of the oligomeric compound comprises at least one unmodified nucleoside. In certain embodiments, the unmodified nucleoside is a ribonucleoside. In certain embodiments, the unmodified nucleoside is a deoxyribonucleoside.

In certain embodiments, the remainder of the oligomeric compound comprises at least two modified nucleosides. In certain embodiments, the at least two modified nucleosides comprise the same modification. In certain embodiments, the at least two modified nucleosides comprise different modifications. In certain embodiments, at least one of the at least two modified nucleosides comprises a sugar surrogate. In certain embodiments, at least one of the at least two modified nucleosides comprises a 2'-modification. In certain embodiments, each of the at least two modified nucleosides is independently selected from 2'-F nucleosides, 2'-$OCH_3$ nucleosides and 2'-$O(CH_2)_2OCH_3$ nucleosides. In certain embodiments, each of the at least two modified nucleosides is a 2'-F nucleoside. In certain embodiments, each of the at least two modified nucleosides is a 2'-$OCH_3$ nucleoside. In certain embodiments, each of the at least two modified nucleosides is a 2'-$O(CH_2)_2OCH_3$ modified nucleoside. In certain embodiments, essentially every nucleoside of the oligomeric compound is a modified nucleoside. In certain embodiments, every nucleoside of the oligomeric compound is a modified nucleoside.

In certain embodiments, the remainder of the oligomeric compound comprises: 1-20 first-type regions, each first-type region independently comprising 1-20 contiguous nucleosides wherein each nucleoside of each first-type region comprises a first-type modification; 0-20 second-type regions, each second-type region independently comprising 1-20 contiguous nucleosides wherein each nucleoside of each second-type region comprises a second-type modification; and 0-20 third-type regions, each third-type region independently comprising 1-20 contiguous nucleosides wherein each nucleoside of each third-type region comprises a third-type modification; wherein the first-type modification, the second-type modification, and the third-type modification are each independently selected from 2'-F, 2'-$OCH_3$, 2'-$O(CH_2)_2OCH_3$, BNA, F-HNA, 2'-H and 2'-OH; provided that the first-type modification, the second-type modification, and the third-type modification are each different from one another.

In certain embodiments, the remainder of the oligomeric compound comprises 2-20 first-type regions; 3-20 first-type regions; 4-20 first-type regions; 5-20 first-type regions; or 6-20 first-type regions. In certain embodiments, the remainder of the oligomeric compound comprises 1-20 second-type regions; 2-20 second-type regions; 3-20 second-type regions; 4-20 second-type regions; or 5-20 second-type regions. In certain embodiments, the remainder of the oligomeric compound comprises 1-20 third-type regions; 2-20 third-type regions; 3-20 third-type regions; 4-20 third-type regions; or 5-20 third-type regions.

In certain embodiments, the remainder of the oligomeric compound comprises a third-type region at the 3'-end of the oligomeric compound. In certain embodiments, the remainder of the oligomeric compound comprises a third-type region at the 3'-end of the oligomeric compound. In certain embodiments, the third-type region contains from 1 to 3 modified nucleosides and the third-type modification is 2'-O(CH$_2$)$_2$OCH$_3$. In certain embodiments, the third same type region contains two modified nucleosides and the third-type modification is 2'-O(CH$_2$)$_2$OCH$_3$.

In certain embodiments, each first-type region contains from 1 to 5 modified nucleosides. In certain embodiments, each first-type region contains from 6 to 10 modified nucleosides. In certain embodiments, each first-type region contains from 11 to 15 modified nucleosides. In certain embodiments, each first-type region contains from 16 to 20 modified nucleosides.

In certain embodiments, the first-type modification is 2'-F. In certain embodiments, the first-type modification is 2'-OMe. In certain embodiments, the first-type modification is DNA. In certain embodiments, the first-type modification is 2'-O(CH$_2$)$_2$OCH$_3$. In certain embodiments, the first-type modification is 4'-CH$_2$—O-2'. In certain embodiments, the first-type modification is 4'-(CH$_2$)$_2$—O-2'. In certain embodiments, the first-type modification is 4'-C(CH$_3$)H—O-2'. In certain embodiments, each second-type region contains from 1 to 5 modified nucleosides. In certain embodiments, each second-type region contains from 6 to 10 modified nucleosides. In certain embodiments, each second-type region contains from 11 to 15 modified nucleosides. In certain embodiments, each second-type region contains from 16 to 20 modified nucleosides. In certain embodiments, the second-type modification is 2'-F. In certain embodiments, the second-type modification is 2'-OMe. In certain embodiments, the second-type modification is DNA. In certain embodiments, the second-type modification is 2'-O(CH$_2$)$_2$OCH$_3$. In certain embodiments, the second-type modification is 4'-CH$_2$—O-2'. In certain embodiments, the second-type modification is 4'-(CH$_2$)$_2$—O-2'. In certain embodiments, the second-type modification is 4'-C(CH$_3$)H—O-2'. In certain embodiments, the oligomeric compound has an alternating motif wherein the first-type regions alternate with the second-type regions.

In certain embodiments, the invention provides oligomeric compounds wherein the 5' terminal nucleoside is a compound of Formula II, IIa, IIb, IIc, IId or IIe and the remainder of the oligomeric compound comprises at least one region of nucleosides having a nucleoside motif: $(A)_n$-$(B)_n$-$(A)_n$-$(B)_n$, wherein: A an B are differently modified nucleosides; and each n is independently selected from 1, 2, 3, 4, and 5.

In certain embodiments, A and B are each independently selected from a bicyclic and a 2'-modified nucleoside. In certain embodiments, at least one of A and B is a bicyclic nucleoside. In certain embodiments, at least one of A and B is a (4'-CH$_2$—O-2') BNA nucleoside. In certain embodiments, at least one of A and B is a (4'-(CH$_2$)$_2$—O-2') BNA nucleoside. In certain embodiments, at least one of A and B is a (4'-C(CH$_3$)H—O-2') BNA nucleoside. In certain embodiments, at least one of A and B is a 2'-modified nucleoside. In certain embodiments, the 2'-modified nucleoside is selected from: a 2'-F nucleoside, a 2'-OCH$_3$ nucleoside, and a 2'-O(CH$_2$)$_2$OCH$_3$ nucleoside. In certain embodiments, A and B are each independently selected from: a 2'-F nucleoside, a 2'-OCH$_3$ nucleoside, a 2'-O(CH$_2$)$_2$OCH$_3$ nucleoside, a (4'-CH$_2$—O-2') BNA nucleoside, a (4'-(CH$_2$)$_2$—O-2') BNA nucleoside, a (4'-C(CH$_3$)H—O-2') BNA nucleoside, a DNA nucleoside, an RNA nucleoside, and an F-HNA nucleoside. In certain embodiments, A and B are each independently selected from: a 2'-F nucleoside, a 2'-OCH$_3$ nucleoside, a (4'-CH$_2$—O-2') BNA nucleoside, a (4'-(CH$_2$)$_2$—O-2') BNA nucleoside, a (4'-C(CH$_3$)H—O-2') BNA nucleoside, and a DNA nucleoside. In certain embodiments, one of A and B is a 2'-F nucleoside. In certain embodiments, one of A and B is a 2'-OCH$_3$ nucleoside. In certain embodiments, one of A and B is a 2'-O(CH$_2$)$_2$OCH$_3$ nucleoside. In certain embodiments, A is a 2'-F nucleoside and B is a 2'-OCH$_3$ nucleoside. In certain embodiments, A is a 2'-OCH$_3$ nucleoside and B is a 2'-F nucleoside. In certain embodiments, one of A and B is selected from a (4'-CH$_2$—O-2') BNA nucleoside, a (4'-(CH$_2$)$_2$—O-2') BNA nucleoside, and a (4'-C(CH$_3$)H—O-2') BNA nucleoside and the other of A and B is a DNA nucleoside.

In certain embodiments, the invention provides oligomeric compounds wherein the 5' terminal nucleoside is a compound of Formula II, IIa, IIb, IIc, IId or IIe and the remainder of the oligomeric compound comprises at least one region of nucleosides having a nucleoside motif: $(A)_x$-$(B)_2$-$(A)_y$-$(B)_2$-$(A)_z$-$(B)_3$ wherein: A is a nucleoside of a first type; B is a nucleoside of a second type; X is 0-10; Y is 1-10; and Z is 1-10.

In certain embodiments, X is selected from 0, 1, 2 and 3. In certain embodiments, X is selected from 4, 5, 6 and 7. In certain embodiments, Y is selected from 1, 2 and 3. In certain embodiments, Y is selected from 4, 5, 6 and 7. In certain embodiments, Z is selected from 1, 2 and 3. In certain embodiments, Z is selected from 4, 5, 6 and 7. In certain embodiments, A is a 2'-F nucleoside. In certain embodiments, B is a 2'-OCH$_3$ nucleoside.

In certain embodiments, the invention provides oligomeric compounds wherein the 5' terminal nucleoside is a compound of Formula II, IIa, IIb, IIc, IId or IIe and wherein the oligomeric compounds comprises a 3'-region consisting of from 1 to 5 nucleosides at the 3'-end of the oligomeric compound wherein: the nucleosides of the 3'-region each comprises the same modification as one another; and the nucleosides of the 3'-region are modified differently than the last nucleoside adjacent to the 3'-region.

In certain embodiments, the modification of the 3'-region is different from any of the modifications of any of the other nucleosides of the oligomeric compound. In certain embodiments, the nucleosides of the 3'-region are 2'-O(CH$_2$)$_2$OCH$_3$ nucleosides. In certain embodiments, the 3'-region consists of 2 nucleosides. In certain embodiments, the 3'-region consists of 3 nucleosides. In certain embodiments, each nucleoside of the 3'-region comprises a uracil base. In certain embodiments, each nucleoside of the 3'-region comprises an adenine base. In certain embodiments, each nucleoside of the 3'-region comprises a thymine base.

In certain embodiments, the remainder of the oligomeric compound comprises a region of uniformly modified nucleosides. In certain embodiments, the region of uniformly modified nucleosides comprises 2-20 contiguous uniformly modified nucleosides. In certain embodiments, the region of uniformly modified nucleosides comprises 3-20 contiguous uniformly modified nucleosides. In certain embodiments, the region of uniformly modified nucleosides comprises 4-20 contiguous uniformly modified nucleosides. In certain embodiments, the region of uniformly modified nucleosides comprises 5-20 contiguous uniformly modified nucleosides. In certain embodiments, the region of uniformly modified nucleosides comprises 6-20 contiguous uniformly modified nucleosides. In certain embodiments, the region of uniformly modified nucleosides comprises 5-15 contiguous uniformly modified nucleosides. In certain embodiments, the region of uniformly modified nucleosides comprises 6-15 contiguous uniformly modified nucleosides. In certain embodiments, the region of uniformly modified nucleosides comprises 5-10 contiguous uniformly modified nucleosides. In certain embodiments, the region of uniformly modified nucleosides comprises 6-10 contiguous uniformly modified nucleosides.

In certain embodiments, the remainder of the oligomeric compound comprises a region of alternating modified nucleosides and a region of uniformly modified nucleosides. In certain embodiments, the region of alternating nucleotides is 5' of the region of fully modified nucleosides. In certain embodiments, the region of alternating nucleotides is 3' of the region of fully modified nucleosides. In certain embodiments, the alternating region and the fully modified region are immediately adjacent to one another. In certain embodiments, the oligomeric compound has additional nucleosides between the alternating region and the fully modified region.

In certain embodiments, the remainder of the oligomeric compound comprises at least one region of nucleosides having a motif I: $N_f(PS)N_m(PO)$, wherein: $N_f$ is a 2'-F nucleoside, $N_m$ is a 2'-OCH$_3$ nucleoside PS is a phosphorothioate linking group; and PO is a phosphodiester linking group.

In certain embodiments, the 5' terminal nucleoside is a compound of formula II, IIa, IIb, IIc, IId or IIe and the second nucleoside from the 5' terminal end is $N_f$.

In certain embodiments, the oligomeric compound comprises at least 2, or 3, or 4, or 6, or 7, or 8, or 9, or 10 separate regions having motif I.

In certain embodiments, the remainder of the oligomeric compound comprises at least one region having a nucleoside motif selected from: AABBAA; ABBABB; AABAAB; ABBABAABB; ABABAA; AABABAB; ABABAA; ABBAABBABABAA; BABBAABBABABAA; or ABAB-BAAB-BABABAA; wherein A is a nucleoside of a first type and B is a nucleoside of a second type.

In certain embodiments, oligomeric compounds of the invention comprise one or more conjugate groups. In certain embodiments, oligomeric compounds of the invention consist of an oligonucleotide.

In certain embodiments, the invention provides oligomeric compounds having the formula: 5'-(Z)-(L-Q$_a$-L-Q$_b$)$_t$-(L-Q$_a$)$_u$-(L-Q$_c$)$_v$-(G)$_a$-3' wherein: each L is an internucleoside linking group; G is a conjugate or a linking group linking the oligomeric compound to a conjugate; a is 0 or 1; each of Q$_a$, Q$_b$ and Q$_c$ is, independently, a 2'-modified nucleoside having a 2'-substituent group selected from halogen, allyl, amino, azido, O-allyl, O—C$_1$-C$_6$ alkyl, OCF$_3$, O—(CH$_2$)$_2$—O—CH$_3$, O(CH$_2$)$_2$SCH$_3$, O—(CH$_2$)$_2$—O—N(J$_5$)(J$_6$) and O—CH$_2$—C(=O)—N(J$_a$)(J$_b$), where each J$_a$ and J$_b$ is, independently, H, an amino protecting group or substituted or unsubstituted C$_1$-C$_6$ alkyl; provided that Q$_a$, Q$_b$ and Q$_c$ are different from one another; t is from 4 to 8; u is 0 or 1; v is from 1 to 3; and Z is a compound of formula II, IIa, IIb, IIc, IId or IIe.

In certain embodiments, each Q$_a$ and Q$_b$ is, independently, a 2'-modified nucleoside having a 2'-substituent group selected from halogen and O—C$_1$-C$_6$ alkyl. In certain embodiments, each Q$_a$ and Q$_b$ is, independently, a 2'-modified nucleoside having a 2'-substituent group selected from F and O-methyl. In certain embodiments, each Q is a 2'-modified nucleoside having a 2'-substituent group of O—(CH$_2$)$_2$—OCH$_3$. In certain embodiments, a is 0. In certain embodiments, v is 2. In certain embodiments, u is 0. In certain embodiments, u is 1.

In certain of any of the above embodiments, the remainder of the oligomeric compound comprises an oligonucleotide consisting of 8-80 linked nucleosides; 8-26 linked nucleosides; 10-24 linked nucleosides; 16-22 linked nucleosides; 16-18 linked nucleosides; or 19-22 linked nucleosides. In certain of any of the above embodiments, the second nucleoside from the 5'-end comprises a sugar moiety comprising a 2'-substituent selected from OH and a halogen. In certain embodiments, the second nucleoside from the 5'-end is a 2'-F modified nucleoside.

In certain of any of the above embodiments, the oligomeric compound comprises at least one modified linking group. In certain embodiments, each internucleoside linking group is, independently, phosphodiester or phosphorothioate. In certain embodiments, the 5'-most internucleoside linking group is a phosphorothioate linking group. In certain embodiments, oligomeric compounds comprise at least one phosphorothioate region comprising at least two contiguous phosphorothioate linking groups. In certain embodiments, the at least one phosphorothioate region comprises from 3 to 12 contiguous phosphorothioate linking groups. In certain embodiments, the at least one phosphorothioate region comprises from 6 to 8 phosphorothioate linking groups. In certain embodiments, the at least one phosphorothioate region is located at the 3'-end of the oligomeric compound. In certain embodiments, the at least one phosphorothioate region is located within 3 nucleosides of the 3'-end of the oligomeric compound. In certain embodiments, the 7-9 internucleoside linkages at the 3'end of the oligonucleotide are phosphorothioate linkages and the internucleoside linkage at the 5'-end is a phosphorothioate linkage.

In certain embodiments, the invention provides oligomeric compounds comprising an oligonucleotide consisting of 10 to 30 linked nucleosides wherein:
(a) the nucleoside at the 5' end has formula II, IIa, IIb, IIc, IId or IIe:
(b) the sugar moiety of the second nucleoside from the 5'-end is selected from an unmodified 2'-OH sugar, and a modified sugar comprising a modification selected from: 2'-halogen, 2'O-alkyl, and 2'-O-substituted alkyl; and
(c) the first internucleoside linkage at the 5'-end and the last seven internucleoside linkages at the 3'-end are phosphorothioate linkages; and
(d) at least one internucleoside linkage is other than a phosphorothioate linkage.

In certain embodiments, the oligomeric compound is an antisense compound. In certain embodiments, the antisense compound is an RNAi compound. In certain embodiments, the antisense compound is a single-stranded RNAi compound. In certain embodiments, the antisense compound is a double-stranded RNAi compound (siRNA) in which one or both strands is an oligomeric compound as disclosed herein. In certain embodiments, the antisense compound is a microRNA mimic. In certain embodiments, the antisense compound is an RNase H antisense compound. In certain embodiments, the antisense compound modulates splicing.

In certain embodiments, at least a portion of the nucleobase sequence of the oligomeric compound is complementary to a portion of a target nucleic acid, wherein the target nucleic acid is selected from: a target mRNA, a target pre-mRNA, a target microRNA, and a target non-coding RNA. In certain embodiments, the nucleobase sequence of the oligomeric compound comprises a region of 100% complementarity to the target nucleic acid and wherein the region of 100% complementarity is at least 10 nucleobases. In certain embodiments, the region of 100% complementarity is at least 15 nucleobases. In certain embodiments, the region of 100% complementarity is at least 20 nucleobases. In certain embodiments, the oligonucleotide is at least 85% complementary to the target nucleic acid. In certain embodiments, the oligonucleotide is at least 90% complementary to the target nucleic acid. In certain embodiments, the oligonucleotide is at least 95% complementary to the target nucleic acid. In certain embodiments, the oligonucleotide is at least 98% complementary to the target nucleic acid. In certain embodiments, the oligonucleotide is 100% complementary to the target nucleic acid.

In certain embodiments, the antisense compound is a microRNA mimic having a nucleobase sequence comprising a portion that is at least 80% identical to the seed region of a microRNA and that has overall identity with the microRNA of at least 70%. In certain embodiments, the nucleobase sequence of the microRNA mimic has a portion that is at least 80% identical to the sequence of the seed region of a microRNA and has overall identity with the microRNA of at least 75%. In certain embodiments, the nucleobase sequence of the microRNA mimic has a portion that is at least 80% identical to the sequence of the seed region of a microRNA and has overall identity with the microRNA of at least 80%. In certain embodiments, the nucleobase sequence of the microRNA mimic has a portion that is at least 100% identical to the sequence of the seed region of a microRNA and has overall identity with the microRNA of at least 80%. In certain embodiments, the nucleobase sequence of the microRNA mimic has a portion that is at least 100% identical to the sequence of the seed region of a microRNA and has overall identity with the microRNA of at least 85%. In certain embodiments, the nucleobase sequence of the microRNA mimic has a portion that is 100% identical to the sequence of the microRNA. In certain embodiments, nucleobase sequence of the oligonucleotide comprises a region of 100% complementarity to a seed match segment of a target nucleic acid. In certain embodiments, the antisense compound is a microRNA mimic having a nucleobase sequence comprising a portion that is at least 80% identical to the seed region of a microRNA and that has overall identity with the microRNA of at least 50%. In certain embodiments, the antisense compound is a microRNA mimic having a nucleobase sequence comprising a portion that is at least 80% identical to the seed region of a microRNA and that has overall identity with the microRNA of at least 55%. In certain embodiments, the antisense compound is a microRNA mimic having a nucleobase sequence comprising a portion that is at least 80% identical to the seed region of a microRNA and that has overall identity with the microRNA of at least 60%. In certain embodiments, the antisense compound is a microRNA mimic having a nucleobase sequence comprising a portion that is at least 80% identical to the seed region of a microRNA and that has overall identity with the microRNA of at least 65%. In certain embodiments, the oligomeric compound comprises a nucleobase sequence selected from a microRNA sequence found in miRBase. In certain embodiments, the oligomeric compound consists of a nucleobase sequence selected from a microRNA sequence found in miRBase.

In certain embodiments, the target nucleic acid is a target mRNA. In certain embodiments, the target nucleic acid is a target pre-mRNA. In certain embodiments, the target nucleic acid is a non-coding RNA. In certain embodiments, the target nucleic acid is a microRNA. In certain embodiments, the target nucleic acid is a pre-mir. In certain embodiments, the target nucleic acid is a pri-mir.

In certain embodiments, the nucleobase sequence of the oligonucleotide comprises a region of 100% complementarity to the target nucleic acid and wherein the region of 100% complementarity is at least 10 nucleobases. In certain embodiments, the nucleobase sequence of the oligonucleotide comprises a region of 100% complementarity to the target nucleic acid and wherein the region of 100% complementarity is at least 6 nucleobases. In certain embodiments, the nucleobase sequence of the oligonucleotide comprises a region of 100% complementarity to the target nucleic acid and wherein the region of 100% complementarity is at least 7 nucleobases. In certain embodiments, the target nucleic acid is a mammalian target nucleic acid. In certain embodiments, the mammalian target nucleic acid is a human target nucleic acid.

In certain embodiments, oligomeric compounds comprise from 1 to 3 terminal group nucleosides on at least one end of the oligomeric compound. In certain embodiments, oligomeric compounds comprise from 1 to 3 terminal group nucleosides at the 3'-end. In certain embodiments, oligomeric compounds comprise from 1 to 3 terminal group nucleosides at the 5'-end.

In certain embodiments, oligomeric compounds of the invention are single stranded. In certain embodiments, oligomeric compounds of the invention are paired with a second oligomeric compound to form a double stranded composition.

In certain embodiments, the invention provides pharmaceutical compositions comprising an oligomeric compound and a pharmaceutically acceptable diluent or carrier. In certain embodiments, the pharmaceutically acceptable diluent or carrier is pharmaceutical grade sterile saline.

In certain embodiments, the invention provides methods comprising contacting a cell with an oligomeric compound described herein. In certain embodiments, such methods comprise detecting antisense activity. In certain embodiments, the detecting antisense activity comprises detecting a phenotypic change in the cell. In certain embodiments, the detecting antisense activity comprises detecting a change in the amount of target nucleic acid in the cell. In certain embodiments, the detecting antisense activity comprises detecting a change in the amount of a target protein. In certain embodiments, the cell is in vitro. In certain embodiments, the cell is in an animal. In certain embodiments, animal is a mammal. In certain embodiments, the mammal is a human.

In certain embodiments, the invention provides methods of modulating a target mRNA in a cell comprising contacting the cell with an oligomeric compound of the invention and thereby modulating the mRNA in a cell. In certain embodiments, such methods comprise detecting a phenotypic change in the cell. In certain embodiments, methods comprise detecting a decrease in mRNA levels in the cell. In certain embodiments, methods comprise detecting a change in the amount of a target protein. In certain embodiments, the cell is in vitro. In certain embodiments, the cell is in an animal. In certain embodiments, the animal is a mammal. In certain embodiments, the mammal is a human.

In certain embodiments, the invention provides methods of administering to an animal a pharmaceutical composition of the invention. In certain embodiments, the animal is a mammal. In certain embodiments, the mammal is a human. In certain embodiments, the methods comprise detecting antisense activity in the animal. In certain embodiments, the methods comprise detecting a change in the amount of target nucleic acid in the animal. In certain embodiments, the methods comprise detecting a change in the amount of a target protein in the animal. In certain embodiments, the methods comprise detecting a phenotypic change in the animal. In certain embodiments, the phenotypic change is a change in the amount or quality of a biological marker of activity.

In certain embodiments, the invention provides use of an oligomeric compound of the invention for the manufacture of a medicament for the treatment of a disease characterized by undesired gene expression.

In certain embodiments, the invention provides use of an oligomeric compound of the invention for the manufacture of a medicament for treating a disease by inhibiting gene expression.

In certain embodiments, the invention provides methods of comprising detecting antisense activity wherein the antisense activity is microRNA mimic activity. In certain embodiments, the detecting microRNA mimic activity comprises detecting a change in the amount of a target nucleic acid in a cell. In certain embodiments, the detecting microRNA mimic activity comprises detecting a change in the amount of a target protein in cell.

In certain embodiments, methods for inhibiting gene expression comprising contacting a cell with an oligomeric compound or a double stranded composition as provided herein wherein said oligomeric compound or one of the strands of the double stranded composition comprises from about 8 to about 40 monomeric subunits and is complementary to a target RNA. In certain embodiments, the cell is in an animal. In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function. In certain embodiments, the methods further comprise detecting the levels of target RNA.

In certain embodiments, an in vitro method of inhibiting gene expression is provided comprising contacting one or more cells or a tissue with an oligomeric compound or a double stranded composition as provided herein.

In certain embodiments, an oligomeric compound or a double stranded composition as provided herein is used for an in vivo method of inhibiting gene expression said method comprising contacting one or more cells, a tissue or an animal with an oligomeric compound or a double stranded composition as provided herein.

In certain embodiments, an oligomeric compound or a double stranded composition as provided herein is used in medical therapy.

DETAILED DESCRIPTION OF THE INVENTION

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

As used herein, "nucleoside" refers to a compound comprising a heterocyclic base moiety and a sugar moiety. Nucleosides include, but are not limited to, naturally occurring nucleosides (as found in DNA and RNA), abasic nucleosides, modified nucleosides, and nucleosides having mimetic bases and/or sugar groups. Nucleosides may be modified with any of a variety of substituents. Nucleosides may include a phosphate moiety.

As used herein, "sugar moiety" means a natural or modified sugar ring or sugar surrogate.

As used herein the term "sugar surrogate" refers to a structure that is capable of replacing the furanose ring of a naturally occurring nucleoside. In certain embodiments, sugar surrogates are non-furanose (or 4'-substituted furanose) rings or ring systems or open systems. Such structures include simple changes relative to the natural furanose ring, such as a six membered ring or may be more complicated as is the case with the non-ring system used in peptide nucleic acid. Sugar surrogates includes without limitation morpholinos, cyclohexenyls and cyclohexitols. In most nucleosides having a sugar surrogate group the heterocyclic base moiety is generally maintained to permit hybridization.

As used herein, "nucleotide" refers to a nucleoside further comprising a phosphate linking group. As used herein, "linked nucleosides" may or may not be linked by phosphate linkages and thus includes "linked nucleotides."

As used herein, "nucleobase" or "heterocyclic base moiety" refers to the heterocyclic base portion of a nucleoside. Nucleobases may be naturally occurring or may be modified. In certain embodiments, a nucleobase may comprise any atom or group of atoms capable of hydrogen bonding to a base of another nucleic acid.

As used herein, "modified nucleoside" refers to a nucleoside comprising at least one modification compared to naturally occurring RNA or DNA nucleosides. Such modification may be at the sugar moiety and/or at the nucleobases.

As used herein, "bicyclic nucleoside" or "BNA" refers to a nucleoside having a sugar moiety comprising a sugar-ring (including, but not limited to, furanose, such as sugar surrogates) comprising a bridge connecting two carbon atoms of the sugar ring to form a second ring. In certain embodiments, the bridge connects the 4' carbon to the 2' carbon of a 5-membered sugar ring.

As used herein, "4'-2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "2'-modified" or "2'-substituted" refers to a nucleoside comprising a sugar comprising a substituent at the 2' position other than H or OH. 2'-Modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thiol, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_n)$, or O—$CH_2$—C(=O)—N$(R_m)(R_n)$, where each $R_m$ and $R_n$ is, independently, H or substituted or unsubstituted $C_1$-$C_{10}$ alkyl. 2'-modifed nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

As used herein "oligonucleoside" refers to an oligonucleotide in which none of the internucleoside linkages contains a phosphorus atom. As used herein, oligonucleotides include oligonucleosides.

As used herein, "modified oligonucleotide" refers to an oligonucleotide comprising at least one modified nucleoside and/or at least one modified internucleoside linkage.

As used herein "internucleoside linkage" refers to a covalent linkage between adjacent nucleosides.

As used herein "naturally occurring internucleoside linkage" refers to a 3' to 5' phosphodiester linkage.

As used herein, "modified internucleoside linkage" refers to any internucleoside linkage other than a naturally occurring internucleoside linkage.

As used herein, "oligomeric compound" refers to a polymeric structure comprising two or more sub-structures or monomeric subunits. In certain embodiments, an oligomeric compound is an oligonucleotide. In certain embodiments, an oligomeric compound comprises one or more conjugate groups and/or terminal groups.

As used herein, unless otherwise indicated or modified, the term "double-stranded" refers to two separate oligomeric compounds that are hybridized to one another. Such double stranded compounds may have one or more or non-hybridizing nucleosides at one or both ends of one or both strands (overhangs) and/or one or more internal non-hybridizing nucleosides (mismatches) provided there is sufficient complementarity to maintain hybridization under physiologically relevant conditions.

As used herein, the term "self-complementary" or "hairpin" refers to a single oligomeric compound that comprises a duplex region formed by the oligomeric compound hybridizing to itself.

As used herein, the term "single-stranded" refers to an oligomeric compound that is not hybridized to its complement and that does not have sufficient self-complementarity to form a hair-pin structure under physiologically relevant conditions. A single-stranded compound may be capable of binding to its complement to become a double-stranded or partially double-stranded compound.

As used herein, "terminal group" refers to one or more atom attached to either, or both, the 3' end or the 5' end of an oligonucleotide. In certain embodiments a terminal group is a conjugate group. In certain embodiments, a terminal group comprises one or more additional nucleosides.

As used herein, "conjugate" refers to an atom or group of atoms bound to an oligonucleotide or oligomeric compound. In general, conjugate groups modify one or more properties of the compound to which they are attached, including, but not limited to pharmakodynamic, pharmacokinetic, binding, absorption, cellular distribution, cellular uptake, charge and clearance. Conjugate groups are routinely used in the chemical arts and are linked directly or via an optional linking moiety or linking group to the parent compound such as an oligomeric compound. In certain embodiments, conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. In certain embodiments, conjugates are terminal groups. In certain embodiments, conjugates are attached to a 3' or 5' terminal nucleoside or to an internal nucleosides of an oligonucleotide.

As used herein, "conjugate linking group" refers to any atom or group of atoms used to attach a conjugate to an oligonucleotide or oligomeric compound. Linking groups or bifunctional linking moieties such as those known in the art are amenable to the present invention.

As used herein, "antisense compound" refers to an oligomeric compound, at least a portion of which is at least partially complementary to a target nucleic acid to which it hybridizes. In certain embodiments, an antisense compound modulates (increases or decreases) expression or amount of a target nucleic acid. In certain embodiments, an antisense compound alters splicing of a target pre-mRNA resulting in a different splice variant. In certain embodiments, an antisense compound modulates expression of one or more different target proteins. Antisense mechanisms contemplated herein include, but are not limited to an RNase H mechanism, RNAi mechanisms, splicing modulation, translational arrest, altering RNA processing, inhibiting microRNA function, or mimicking microRNA function.

As used herein, "expression" refers to the process by which a gene ultimately results in a protein. Expression includes, but is not limited to, transcription, splicing, post-transcriptional modification, and translation.

As used herein, "RNAi" refers to a mechanism by which certain antisense compounds effect expression or amount of a target nucleic acid. RNAi mechanisms involve the RISC pathway.

As used herein, "RNAi compound" refers to an oligomeric compound that acts, at least in part, through an RNAi mechanism to modulate a target nucleic acid and/or protein encoded by a target nucleic acid. RNAi compounds include, but are not limited to double-stranded short interfering RNA (siRNA), single-stranded RNA (ssRNA), and microRNA, including microRNA mimics.

As used herein, "antisense oligonucleotide" refers to an antisense compound that is an oligonucleotide.

As used herein, "antisense activity" refers to any detectable and/or measurable activity attributable to the hybridization of an antisense compound to its target nucleic acid. In certain embodiments, such activity may be an increase or decrease in an amount of a nucleic acid or protein. In certain embodiments, such activity may be a change in the ratio of splice variants of a nucleic acid or protein. Detection and/or measuring of antisense activity may be direct or indirect. For example, in certain embodiments, antisense activity is assessed by detecting and/or measuring the amount of target protein or the relative amounts of splice variants of a target protein. In certain embodiments, antisense activity is assessed by detecting and/or measuring the amount of target nucleic acids and/or cleaved target nucleic acids and/or alternatively spliced target nucleic acids. In certain embodiments, antisense activity is assessed by observing a phenotypic change in a cell or animal.

As used herein "detecting" or "measuring" in connection with an activity, response, or effect indicate that a test for detecting or measuring such activity, response, or effect is performed. Such detection and/or measuring may include values of zero. Thus, if a test for detection or measuring results in a finding of no activity (activity of zero), the step of detecting or measuring the activity has nevertheless been performed. For example, in certain embodiments, the present invention provides methods that comprise steps of detecting antisense activity, detecting toxicity, and/or measuring a marker of toxicity. Any such step may include values of zero.

As used herein, "target nucleic acid" refers to any nucleic acid molecule the expression, amount, or activity of which is capable of being modulated by an antisense compound. In certain embodiments, the target nucleic acid is DNA or RNA. In certain embodiments, the target RNA is mRNA, pre-mRNA, non-coding RNA, pri-microRNA, pre-microRNA, mature microRNA, promoter-directed RNA, or natural antisense transcripts. For example, the target nucleic acid can be a cellular gene (or mRNA transcribed from the gene) whose expression is associated with a particular disorder or disease state, or a nucleic acid molecule from an infectious agent. In certain embodiments, target nucleic acid is a viral or bacterial nucleic acid.

As used herein, "target mRNA" refers to a pre-selected RNA molecule that encodes a protein.

As used herein, "target pre-mRNA" refers to a pre-selected RNA transcript that has not been fully processed into mRNA. Notably, pre-RNA includes one or more intron.

As used herein, "target microRNA" refers to a pre-selected non-coding RNA molecule about 18-30 nucleobases in length that modulates expression of one or more proteins or to a precursor of such a non-coding molecule.

As used herein, "target pdRNA" refers to refers to a pre-selected RNA molecule that interacts with one or more promoter to modulate transcription.

As used herein, "microRNA" refers to a naturally occurring, small, non-coding RNA that represses gene expression at the level of translation. In certain embodiments, a microRNA represses gene expression by binding to a target site within a 3' untranslated region of a target nucleic acid. In certain embodiments, a microRNA has a nucleobase sequence as set forth in miRBase, a database of published microRNA sequences found at http://microrna.sanger.ac.uk/sequences/. In certain embodiments, a microRNA has a nucleobase sequence as set forth in miRBase version 10.1 released December 2007, which is herein incorporated by reference in its entirety. In certain embodiments, a microRNA has a nucleobase sequence as set forth in miRBase version 12.0 released September 2008, which is herein incorporated by reference in its entirety.

As used herein, "microRNA mimic" refers to an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids.

As used herein, "seed region" refers to a region at or near the 5'end of an antisense compound having a nucleobase sequence that is import for target nucleic acid recognition by the antisense compound. In certain embodiments, a seed region comprises nucleobases 2-8 of an antisense compound. In certain embodiments, a seed region comprises nucleobases 2-7 of an antisense compound. In certain embodiments, a seed region comprises nucleobases 1-7 of an antisense compound. In certain embodiments, a seed region comprises nucleobases 1-6 of an antisense compound. In certain embodiments, a seed region comprises nucleobases 1-8 of an antisense compound.

As used herein, "microRNA seed region" refers to a seed region of a microRNA or microRNA mimic. In certain embodiments, a microRNA seed region comprises nucleobases 2-8 of a microRNA or microRNA mimic. In certain embodiments, a microRNA seed region comprises nucleobases 2-7 of a microRNA or microRNA mimic. In certain embodiments, a microRNA seed region comprises nucleobases 1-7 of a microRNA or microRNA mimic. In certain embodiments, a microRNA seed region comprises nucleobases 1-6 of a microRNA or microRNA mimic. In certain embodiments, a microRNA seed region comprises nucleobases 1-8 of a microRNA or microRNA mimic.

As used herein, "seed match segment" refers to a portion of a target nucleic acid having nucleobase complementarity to a seed region. In certain embodiments, a seed match segment has nucleobase complementarity to nucleobases 2-8 of an siRNA, ssRNA, natural microRNA or microRNA mimic. In certain embodiments, a seed match segment has nucleobase complementarity to nucleobases 2-7 of an siRNA, ssRNA, microRNA or microRNA mimic. In certain embodiments, a seed match segment has nucleobase complementarity to nucleobases 1-6 of an siRNA, ssRNA, microRNA or microRNA mimic. In certain embodiments, a seed match segment has nucleobase complementarity to nucleobases 1-7 of an siRNA, ssRNA, microRNA or microRNA mimic. In certain embodiments, a seed match segment has nucleobase complementarity to nucleobases 1-8 of an siRNA, ssRNA, microRNA or microRNA mimic.

As used herein, "seed match target nucleic acid" refers to a target nucleic acid comprising a seed match segment.

As used herein, "microRNA family" refers to a group of microRNAs that share a microRNA seed sequence. In certain embodiments, microRNA family members regulate a common set of target nucleic acids. In certain embodiments, the shared microRNA seed sequence is found at the same nucleobase positions in each member of a microRNA family. In certain embodiments, the shared microRNA seed sequence is not found at the same nucleobase positions in each member of a microRNA family. For example, a microRNA seed sequence found at nucleobases 1-7 of one member of a microRNA family may be found at nucleobases 2-8 of another member of a microRNA family.

As used herein, "target non-coding RNA" refers to a pre-selected RNA molecule that is not translated to generate a protein. Certain non-coding RNA are involved in regulation of expression. As used herein, "target viral nucleic acid" refers to a pre-selected nucleic acid (RNA or DNA) associated with a virus. Such viral nucleic acid includes nucleic acids that constitute the viral genome, as well as transcripts (including reverse-transcripts and RNA transcribed from RNA) of those nucleic acids, whether or not produced by the host cellular machinery. In certain instances, viral nucleic acids also include host nucleic acids that are recruited by a virus upon viral infection.

As used herein, "targeting" or "targeted to" refers to the association of an antisense compound to a particular target nucleic acid molecule or a particular region of nucleotides within a target nucleic acid molecule. An antisense compound targets a target nucleic acid if it is sufficiently complementary to the target nucleic acid to allow hybridization under physiological conditions.

As used herein, "target protein" refers to a protein, the expression of which is modulated by an antisense compound. In certain embodiments, a target protein is encoded by a target nucleic acid: In certain embodiments, expression of a target protein is otherwise influenced by a target nucleic acid.

As used herein, "nucleobase complementarity" or "complementarity" when in reference to nucleobases refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases refers to a pair of nucleobases that do not form hydrogen bonds with one another or otherwise support hybridization.

As used herein, "complementary" in reference to linked nucleosides, oligonucleotides, or nucleic acids, refers to the capacity of an oligomeric compound to hybridize to another oligomeric compound or nucleic acid through nucleobase complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

As used herein, "hybridization" refers to the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, "specifically.hybridizes" refers to the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "modulation" refers to a perturbation of amount or quality of a function or activity when compared to the function or activity prior to modulation. For example, modulation includes the change, either an increase (stimulation or induction) or a decrease (inhibition or reduction) in gene expression. As a further example, modulation of expression can include perturbing splice site selection of pre-mRNA processing, resulting in a change in the amount of a particular splice-variant present compared to conditions that were not perturbed. As a further example, modulation includes perturbing translation of a protein.

As used herein, "motif" refers to a pattern of modifications in an oligomeric compound or a region thereof. Motifs may be defined by modifications at certain nucleosides and/or at certain linking groups of an oligomeric compound.

As used herein, "nucleoside motif" refers to a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "linkage motif" refers to a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "different modifications" or "differently modified" refer to modifications relative to naturally occurring molecules that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified, unless otherwise indicated. For example, a nucleoside comprising a 2'-OMe modified sugar and an adenine nucleobase and a nucleoside comprising a 2'-OMe modified sugar and a thymine nucleobase are not differently modified.

As used herein, "the same modifications" refer to modifications relative to naturally occurring molecules that are the same as one another, including absence of modifications. Thus, for example, two unmodified DNA nucleoside have "the same modification," even though the DNA nucleoside is unmodified.

As used herein, "type of modification" in reference to a nucleoside or a nucleoside of a "type" refers to the modification of a nucleoside and includes modified and unmodified nucleosides. Accordingly, unless otherwise indicated, a "nucleoside having a modification of a first type" may be an unmodified nucleoside.

As used herein, "separate regions" refers to a portion of an oligomeric compound wherein the nucleosides and internucleoside linkages within the region all comprise the same modifications; and the nucleosides and/or the internucleoside linkages of any neighboring portions include at least one different modification.

As used herein, "alternating motif" refers to an oligomeric compound or a portion thereof, having at least four separate regions of modified nucleosides in a pattern $(AB)_nA_m$ where A represents a region of nucleosides having a first type of modification; B represent a region of nucleosides having a different type of modification; n is 2-15; and m is 0 or 1. Thus, in certain embodiments, alternating motifs include 4, 5, 6, 7, 8, 9, 10, 11, 12, 13, 14, 15, 16, 17, 18, 19, or 20 or more alternating regions. In certain embodiments, each A region and each B region independently comprises 1-4 nucleosides.

As used herein, "fully modified" refers to an oligomeric compound or portion thereon wherein each nucleoside is a modified nucleoside. The modifications of the nucleosides of a fully modified oligomeric compound may all be the same or one or more may be different from one another.

As used herein, "uniform modified" or "uniformly modified" refer to oligomeric compounds or portions thereof that comprise the same modifications. The nucleosides of a region of uniformly modified nucleosides all comprise the same modification.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein the sugar group of each monomer subunit within a particular region is essentially the same.

As used herein, "pharmaceutically acceptable carrier or diluent" refers to any substance suitable for use in administering to an animal. In certain embodiments, a pharmaceutically acceptable carrier or diluent is sterile saline. In certain embodiments, such sterile saline is pharmaceutical grade saline.

The terms "substituent" and "substituent group," as used herein, are meant to include groups that are typically added to other groups or parent compounds to enhance desired properties or provide other desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound.

Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino (=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—$SR_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S—(O)$_2R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

The term "alkyl," as used herein, refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

The term "alkenyl," as used herein, refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "acyl," as used herein, refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfmyls, aliphatic sulfinyls, aromatic phosphates, aliphatic phosphates and the like. Acyl groups as used herein may optionally include further substituent groups.

The term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

The term "alkoxy," as used herein, refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The term "aminoalkyl" as used herein, refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

The terms "aralkyl" and "arylalkyl," as used herein, refer to an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to-about 20 carbon atoms in one or more rings. Aryl groups as used herein may optionally include further substituent groups.

The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethyl, pyrimidinylethyl, napthyridinylpropyl and the like. Heteroarylalkyl groups as used herein may optionally include further substituent groups on one or both of the heteroaryl or alkyl portions.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic radical typically includes at least one atom selected from sulfur, nitrogen or oxygen. Examples of heterocyclic radicals include, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The term "hydrocarbyl" includes radical groups that comprise C, O and H. Included are straight, branched and cyclic groups having any degree of saturation. Such hydrocarbyl groups can include one or more heteroatoms selected from N, O and S and can be further mono or poly substituted with one or more substituent groups.

The term "mono or poly cyclic structure" as used herein includes all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylal1cyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =0 groups attached to one of the rings. Mono or poly cyclic structures can be attached to parent molecules using various strategies such as directly through a ring atom, through a substituent group or through a bifunctional linking moiety.

The term "oxo" refers to the group (=O).

Linking groups or bifunctional linking moieties such as those known in the art are useful for attachment of chemical functional groups, conjugate groups, reporter groups and other groups to selective sites in a parent compound such as for example an oligomeric compound. In general, a bifunctional linking moiety comprises a hydrocarbyl moiety having two functional groups. One of the functional groups is selected to bind to a parent molecule or compound of interest and the other is selected to bind to essentially any selected group such as a chemical functional group or a conjugate group. In some embodiments, the linker comprises a chain structure or a polymer of repeating units such as ethylene glycols or amino acid units. Examples of functional groups that are routinely used in bifunctional linking moieties include without limitation, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include without limitation, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

The term "phosphate moiety" as used herein, refers to a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified (di or tri-phosphates) or modified.

As used herein, the term "phosphorus moiety" refers to a group having the formula:

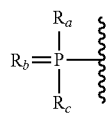

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $R_b$ is O or S.

Phosphorus moieties included herein can be attached to a monomer, which can be used in the preparation of oligomeric compounds, wherein the monomer may be attached using O, S, $NR_d$ or $CR_eR_f$ wherein $R_d$ includes without limitation H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl, and $R_e$ and $R_f$ each, independently, include without limitation H, halogen, $C_1$-$C_6$ alkyl, substituted $C_1$-$C_6$ alkyl, $C_1$-$C_6$ alkoxy or substituted $C_1$-$C_6$ alkoxy. Such linked phosphorus moieties include without limitation, phosphates, modified phosphates, thiophosphates, modified thiophosphates, phosphonates, modified phosphonates, phosphoramidates and modified phosphoramidates.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates,* Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.,* 1977, 99, 7363-7365; Barany et al., *J. Am. Chem. Soc.,* 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoro-acetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of protecting groups commonly used to protect phosphate and phosphorus hydroxyl groups include without limitation, methyl, ethyl, benzyl (Bn), phenyl, isopropyl, tent-butyl, allyl, cyclohexyl (cHex), 4-methoxybenzyl, 4-chlorobenzyl, 4-nitrobenzyl, 4-acyloxybenzyl, 2-methylphenyl, 2,6-dimethylphenyl, 2-chlorophenyl, diphenylmethyl, 4-methylthio-1-butyl, 2-(S-Acetylthio)ethyl (SATE), 2-cyanoethyl, 2-cyano-1,1-dimethylethyl (CDM), 4-cyano-2-butenyl, 2-(trimethylsilyl)ethyl (TSE), 2-(phenylthio)ethyl, 2-(triphenylsilyl)ethyl, 2-(benzylsulfonyl)ethyl, 2,2,2-trichloroethyl, 2,2,2-tribromoethyl, 2,3-dibromopropyl, 2,2,2-trifluoroethyl, thiophenyl, 2-chloro-4-tritylphenyl, 2-bromophenyl, 2-[N-isopropyl-N-(4-methoxybenzoyl)amino]ethyl, 4-(N-trifluoroacetylamino)butyl, 4-oxopentyl, 4-tritylaminophenyl, 4-benzylaminophenyl and morpholino. Wherein more commonly used phosphate and phosphorus protecting groups include without limitation, methyl, ethyl, benzyl (Bn), phenyl, isopropyl, tert-butyl, 4-methoxybenzyl, 4-chlorobenzyl, 2-chlorophenyl and 2-cyanoethyl.

Examples of amino protecting groups include without limitation, carbamate-protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyl-oxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage et al., *Tetrahedron*, 1993, 49(10), 1925-1963; Beaucage et al., *Tetrahedron*, 1993, 49(46), 10441-10488; Beaucage et al., *Tetrahedron*, 1992, 48(12), 2223-2311.

In certain embodiments, compounds having reactive phosphorus groups are provided that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. In certain embodiments, reactive phosphorus groups are selected from diisopropylcyanoethoxy phosphoramidite ($-O^*-P[N[(CH(CH_3)_2]_2]O(CH_2)_2CN$) and H-phosphonate ($-O^*-P(=O)(H)OH$), wherein the $O^*$ is provided from the Markush group for the monomer. A preferred synthetic solid phase synthesis utilizes phosphoramidites ($P^{III}$ chemistry) as reactive phosphites. The intermediate phosphite compounds are subsequently oxidized to the phosphate or thiophosphate ($P^V$ chemistry) using known methods to yield, phosphodiester or phosphorothioate internucleoside linkages. Additional reactive phosphates and phosphites are disclosed in Tetrahedron Report Number 309 (Beaucage and Iyer, *Tetrahedron*, 1992, 48, 2223-2311).

Certain Monomeric Compounds

In certain embodiments, compounds are provided having Formula Ic:

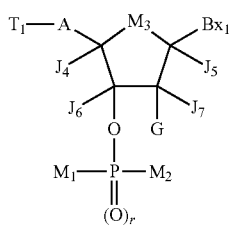

wherein:
$T_1$ is an optionally protected phosphorus moiety;
$M_1$ is H, OH or $OR_1$;
$M_2$ is OH, $OR_1$ or $N(R_1)(R_2)$;
each $R_1$ and $R_2$ is, independently, $C_1$-$C_6$ alkyl, substituted $C_1$-$C_6$ alkyl;
r is 0 or 1;

A has one of the formulas:

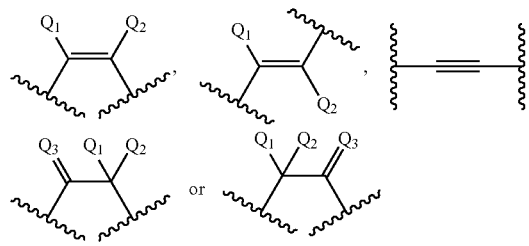

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{18})$, $C(R_{15})=C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

one of $Bx_1$ and $Bx_2$ is a heterocyclic base moiety and the other of $Bx_1$ and $Bx_2$, if present, is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with either $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or $O-[C(R_8)(R_9)]_n-[(C=O)_m-X_1]_j-Z$;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, compounds are provided having Formula I:

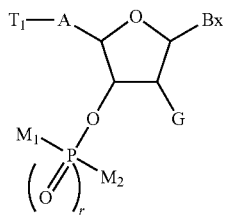

I wherein:
Bx is a heterocyclic base moiety;
$T_1$ is an optionally protected phosphorus moiety;
$M_1$ is H, OH or $OR_1$;
$M_2$ is OH, $OR_1$ or $N(R_1)(R_2)$;
each $R_1$ and $R_2$ is, independently, alkyl or substituted alkyl;
r is 0 or 1;
A has one of the formulas:

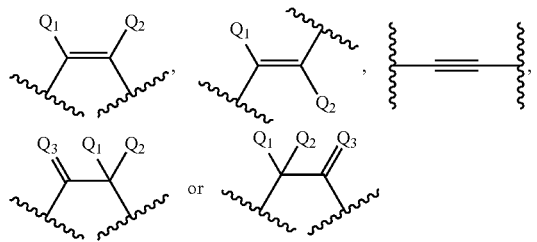

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

G is H, OH, halogen or $O-[C(R_8)(R_9)]_n-[(C=O)_m-X]_j-Z$;

each $R_8$ and $R_9$ is, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;
m is 0 or 1;
j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, compounds are provided having the configuration of Formula Ia:

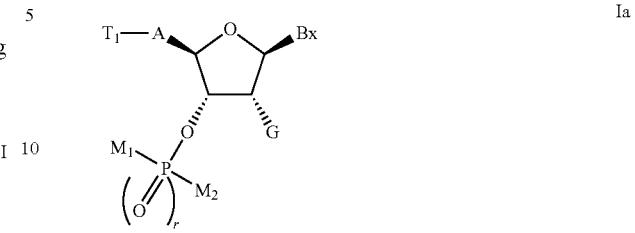

Ia wherein:
Bx is a heterocyclic base moiety;
$T_1$ is an optionally protected phosphorus moiety;
$M_1$ is H, OH or $OR_1$;
$M_2$ is OH, $OR_1$ or $N(R_1)(R_2)$;
each $R_1$ and $R_2$ is, independently, alkyl or substituted alkyl;
r is 0 or 1;
A has one of the formulas:

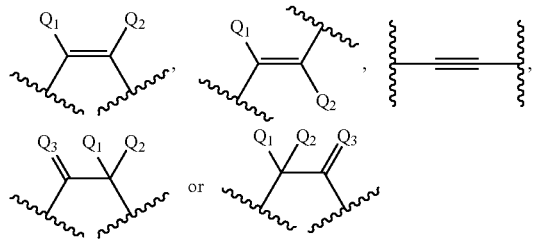

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

G is H, OH, halogen or $O-[C(R_8)(R_9)]_n-[(C=O)_m-X]_j-Z$;

each $R_8$ and $R_9$ is, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;
m is 0 or 1;
j is 0 or 1;

each substituted group comprises one or more optionally protected substituent groups independently selected from halogen, $OJ_1$, $N(J_1)(J_2)$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, G is other than H or OH.

In certain embodiments, compounds are provided having Formula Ib:

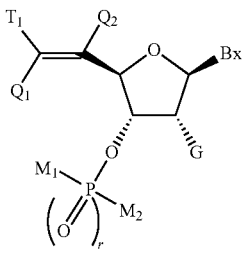

wherein:
Bx is a heterocyclic base moiety;
$T_1$ is an optionally protected phosphorus moiety;
$M_1$ is H, OH or $OR_1$;
$M_2$ is OH, $OR_1$ or $N(R_1)(R_2)$;
each $R_1$ and $R_2$ is, independently, alkyl or substituted alkyl;
r is 0 or 1;
$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;
each $R_3$ and $R_4$ is, independently, H, $C_1$-$C_6$ alkyl, substituted $C_1$-$C_6$ alkyl or $C_1$-$C_6$ alkoxy;
G is H, OH, halogen or O—$[C(R_8)(R_9)]_n$—$[(C=O)_m$—$X]_j$—Z;
each $R_8$ and $R_9$ is, independently, H, halogen, $C_1$-$C_6$ alkyl or substituted $C_1$-$C_6$ alkyl;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $B_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, $SJ_1$, $N_3$, CN, OC(=L)$J_1$, OC(=L)$N(J_1)(J_2)$ and C(=L)$N(J_1)(J_2)$;
L is O, S or $NJ_3$;
each $J_1$, $J_2$ and $J_3$ is, independently, H or $C_1$-$C_6$ alkyl; and
when j is 1 then Z is other than halogen or $N(E_2)(E_3)$.

Certain Oligomeric Compounds

In certain embodiments, oligomeric compounds are provided comprising a compound having Formula IIc:

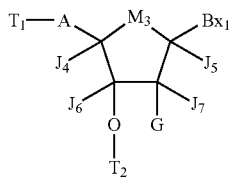

wherein:
$T_1$ is an optionally protected phosphorus moiety;
$T_2$ is an internucleoside linking group linking the compound of Formula IIc to the oligomeric compound;
$M_1$ is H, OH or $OR_1$;
$M_2$ is OH, $OR_1$ or $N(R_1)(R_2)$;

each $R_1$ and $R_2$ is, independently, $C_1$-$C_6$ alkyl, substituted $C_1$-$C_6$ alkyl;
r is 0 or 1;
A has one of the formulas:

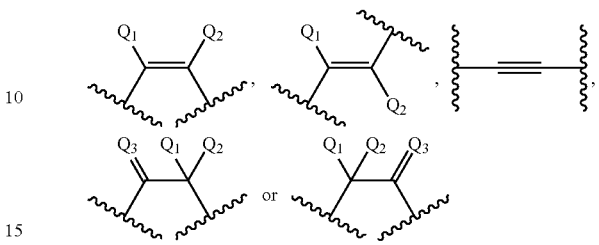

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;
$Q_3$ is O, S, $N(R_5)$ or $C(R_6)(R_7)$;
each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;
$M_3$ is O, S, $NR_{14}$, $C(R_{15})(R_{16})$, $C(R_{15})(R_{16})C(R_{17})(R_{18})$, $C(R_{15})$=$C(R_{17})$, $OC(R_{15})(R_{16})$ or $OC(R_{15})(Bx_2)$;
$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
one of $Bx_1$ and $Bx_2$ is a heterocyclic base moiety and the other of $Bx_1$ and $Bx_2$, if present, is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
or $J_4$ forms a bridge with either $J_5$ or $J_7$ wherein said bridge comprises from 1 to 3 linked biradical groups selected from O, S, $NR_{19}$, $C(R_{20})(R_{21})$, $C(R_{20})$=$C(R_{21})$, C[=$C(R_{20})(R_{21})$] and C(=O) and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
G is H, OH, halogen or O—$[C(R_8)(R_9)]_n$—$[(C=O)_m$—$X_1]_j$—Z;
each $R_8$ and $R_9$ is, independently, H, halogen, $C_1$-$C_6$ alkyl or substituted $C_1$-$C_6$ alkyl;
$X_1$ is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, oligomeric compounds are provided comprising a compound having Formula II:

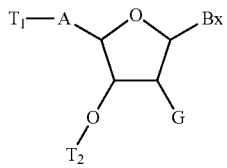

II wherein:

Bx is a heterocyclic base moiety;

$T_1$ is an optionally protected phosphorus moiety;

$T_2$ is an internucleoside linking group linking the compound of Formula II to the remainder of the oligomeric compound;

A has one of the formulas:

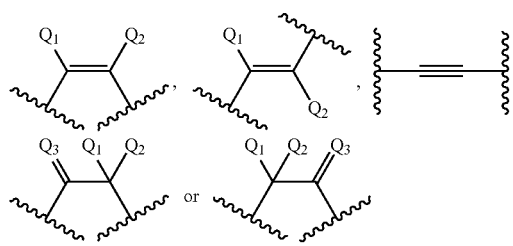

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

G is H, OH, halogen or $O-[C(R_8)(R_9)]_n-[(C=O)_m-X]_j-Z$;

each $R_8$ and $R_9$ is, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, oligomeric compounds are provided comprising a compound having Formula IIa:

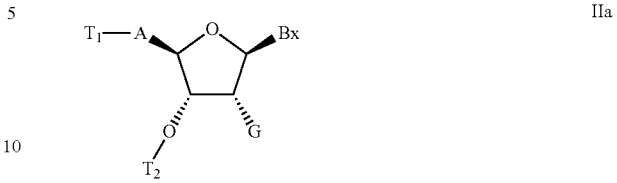

IIa wherein:

Bx is a heterocyclic base moiety;

$T_1$ is an optionally protected phosphorus moiety;

$T_2$ is an internucleoside linking group linking the compound of Formula II to the remainder of the oligomeric compound;

A has one of the formulas:

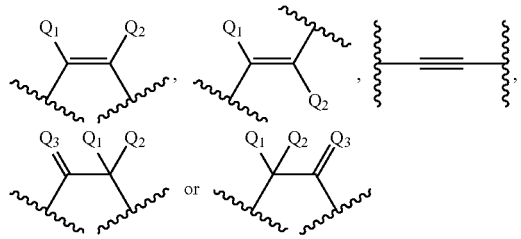

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

G is H, OH, halogen or $O-[C(R_8)(R_9)]_n-[(C=O)_m-X]_j-Z$;

each $R_8$ and $R_9$ is, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, oligomeric compounds are provided comprising a compound having Formula IIb:

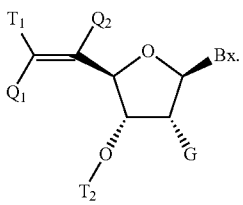

IIb

In certain embodiments, oligomeric compounds are provided comprising a compound having Formula IIb wherein $Q_1$ and $Q_2$ are each H. In certain embodiments, oligomeric compounds are provided comprising a compound having Formula IIb wherein G is $O(CH_2)_2OCH_3$.

In certain embodiments, oligomeric compounds comprise a nucleoside of Formula II, IIa, IIb, IIc, IId or IIe. In certain such embodiments, the nucleoside of Formula II, IIa, IIb, IIc, IId or IIe is at the 5'-terminus. In certain such embodiments, the remainder of the oligomeric compound comprises one or more modifications. Such modifications may include modified sugar moieties, modified nucleobases and/or modified internucleoside linkages. Certain such modifications which may be incorporated in an oligomeric compound comprising a nucleoside of Formula II, IIa, IIb, IIc, IId or IIe is at the 5'-terminus are known in the art.

Certain Modified Sugar Moieties

Oligomeric compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise a chemically modified ribofuranose ring moiety. Examples of chemically modified ribofuranose rings include, without limitation, addition of substitutent groups (including 5' and/or 2' substituent groups; bridging of two ring atoms to form bicyclic nucleic acids (BNA); replacement of the ribosyl ring oxygen atom with S, N(R), or $C(R_1)(R_2)$ (R=H, $C_1$-$C_{12}$ alkyl or a protecting group); and combinations thereof. Examples of chemically modified sugars include, 2'-F-5'-methyl substituted nucleoside (see, PCT International Application WO 2008/101157, published on Aug. 21, 2008 for other disclosed 5',2'-bis substituted nucleosides), replacement of the ribosyl ring oxygen atom with S with further substitution at the 2'-position (see, published U.S. Patent Application US2005/0130923, published on Jun. 16, 2005), or, alternatively, 5'-substitution of a BNA (see, PCT International Application WO 2007/134181, published on Nov. 22, 2007, wherein LNA is substituted with, for example, a 5'-methyl or a 5'-vinyl group).

Examples of nucleosides having modified sugar moieties include, without limitation, nucleosides comprising 5'-vinyl, 5'-methyl (R or S), 4'-S, 2'-F, 2'-OCH$_3$, and 2'-O(CH$_2$)$_2$OCH$_3$ substituent groups. The substituent at the 2' position can also be selected from allyl, amino, azido, thio, O-allyl, O—$C_1$-$C_{10}$ alkyl, OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted $C_1$-$C_{10}$ alkyl.

In certain embodiments, oligomeric compounds of the present invention include one or mre bicyclic nucleoside. In certain such embodimetns, the bicyclic nucleoside comprises a bridge between the 4' and the 2' ribosyl ring atoms. In certain embodiments, oligomeric compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2',and analogs thereof (see, U.S. Pat. No. 7,399,845, issued on Jul. 15, 2008); 4'-C(CH$_3$)(CH$_3$)—O-2' and analogs thereof, (see, published International Application WO2009/006478, published Jan. 8, 2009); 4'-CH$_2$—N(OCH$_3$)-2' and analogs thereof (see, published PCT International Application WO2008/150729, published Dec. 11, 2008); 4'-CH$_2$—O—N(CH$_3$)-2' (see published U.S. Patent Application US2004/0171570, published Sep. 2, 2004); 4'-CH$_2$—N(R)—O-2', wherein R is H, $C_1$-$C_{12}$ alkyl, or a protecting group (see, U.S. Pat. No. 7,427,672, issued on Sep. 23, 2008); 4'-CH$_2$—C(H)(CH$_3$)-2' (see Chattopadhyaya, et al., J. Org. Chem.,2009, 74, 118-134); and 4'-CH$_2$—C(=CH$_2$)-2' and analogs thereof (see, published PCT International Application WO 2008/154401, published on Dec. 8, 2008). Also see, for example: Singh et al., Chem. Commun., 1998, 4, 455-456; Koshkin et al., Tetrahedron, 1998, 54, 3607-3630; Wahlestedt et al., Proc. Natl. Acad Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129(26) 8362-8379 (Jul. 4, 2007); Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; U.S. Pat. Nos. 7,053,207, 6,268,490, 6,770,748, 6,794,499, 7,034,133, 6,525,191, 6,670,461, and 7,399,845; International applications WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S), —O—, —Si(R$_a$)$_2$—, —S(=O)$_x$—, and —N(R$_a$)—;
wherein:

x is 0, 1, or 2;

n is 1, 2, 3, or 4;

each R$_a$ and R$_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

In certain embodiments, the bridge of a bicyclic sugar moiety is, —[C($R_a$)($R_b$)]$_n$—, —[C($R_a$)($R_b$)]$_n$—O—, —C($R_a R_b$)—N(R)—O— or, —C($R_a R_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2', and 4'-CH$_2$—N(R)—O-2'-, wherein each R is, independently, H, a protecting group, or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-Methyleneoxy (4'-CH$_2$—O-2') BNA , (B) β-D-Methyleneoxy (4'-CH$_2$—O-2') BNA , (C) Ethyleneoxy (4'-(CH$_2$)$_2$—O-2') BNA, (D) Aminooxy (4'-CH$_2$—O—N(R)-2') BNA, (E) Oxyamino (4'-CH$_2$-N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

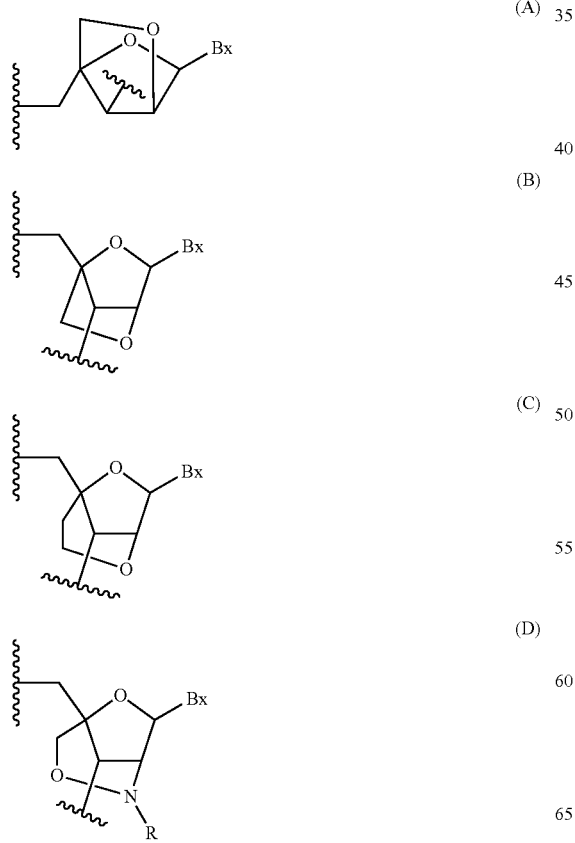

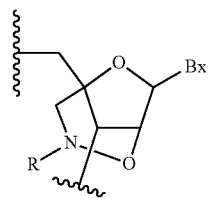

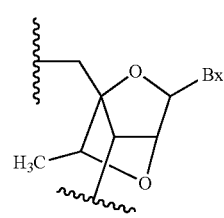

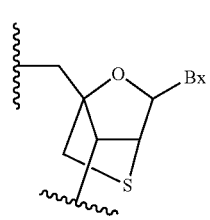

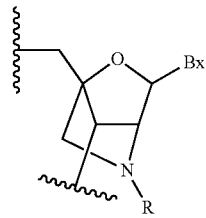

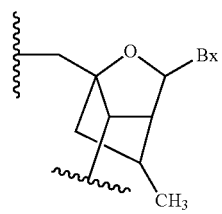

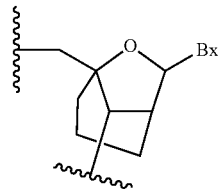

wherein Bx is the base moiety and R is, independently, H, a protecting group, or $C_1$-$C_{12}$ alkyl.

In certain embodiments, bicyclic nucleoside having Formula I:

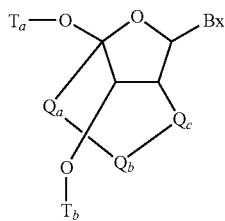

I wherein:

Bx is a heterocyclic base moiety;

$-Q_a-Q_b-Q_c-$ is $-CH_2-N(R_c)-CH_2-$, $-C(=O)-N(R_c)-CH_2-$, $-CH_2-O-N(R_c)-$, $-CH_2-N(R_c)-O-$, or $-N(R_c)-O-CH_2$;

$R_c$ is $C_1-C_{12}$ alkyl or an amino protecting group; and $T_a$ and $T_b$ are each, independently, H, a hydroxyl protecting group, a conjugate group, a reactive phosphorus group, a phosphorus moiety, or a covalent attachment to a support medium.

In certain embodiments, bicyclic nucleoside having Formula II:

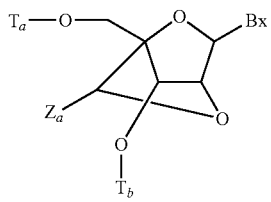

II wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$Z_a$ is $C_1-C_6$ alkyl, $C_2-C_6$ alkenyl, $C_2-C_6$ alkynyl, substituted $C_1-C_6$ alkyl, substituted $C_2-C_6$ alkenyl, substituted $C_2-C_6$ alkynyl, acyl, substituted acyl, substituted amide, thiol, or substituted thio.

In certain embodiments, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$, and $J_e$ is, independently, H, $C_1-C_6$ alkyl, or substituted $C_1-C_6$ alkyl and X is O or $NJ_c$.

In certain embodiments, bicyclic nucleoside having Formula III:

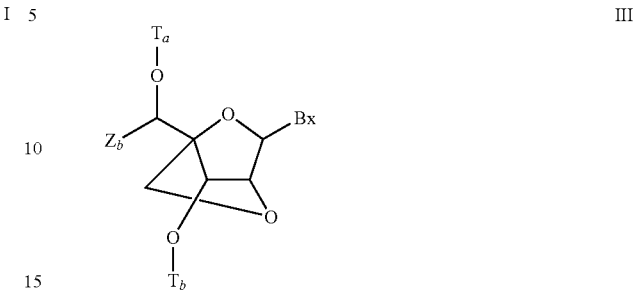

III wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$Z_b$ is $C_1-C_6$ alkyl, $C_2-C_6$ alkenyl, $C_2-C_6$ alkynyl, substituted $C_1-C_6$ alkyl, substituted $C_2-C_6$ alkenyl, substituted $C_2-C_6$ alkynyl, or substituted acyl (C(=O)—).

In certain embodiments, bicyclic nucleoside having Formula IV:

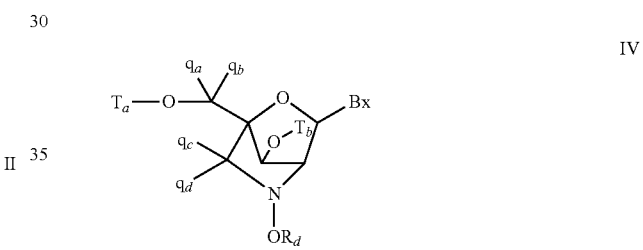

IV wherein:

Bx is a heterocyclic base moiety;

$T_a$ and $T_b$ are each, independently H, a hydroxyl protecting group, a conjugate group, a reactive phosphorus group, a phosphorus moiety, or a covalent attachment to a support medium;

$R_d$ is $C_1-C_6$ alkyl, substituted $C_1-C_6$ alkyl, $C_2-C_6$ alkenyl, substituted $C_2-C_6$ alkenyl, $C_2-C_6$ alkynyl, or substituted $C_2-C_6$ alkynyl;

each $q_a$, $q_b$, $q_c$ and $q_d$ is, independently, H, halogen, $C_1-C_6$ alkyl, substituted $C_1-C_6$ alkyl, $C_2-C_6$ alkenyl, substituted $C_2-C_6$ alkenyl, $C_2-C_6$ alkynyl, or substituted $C_2-C_6$ alkynyl, $C_1-C_6$ alkoxyl, substituted $C_1-C_6$ alkoxyl, acyl, substituted acyl, $C_1-C_6$ aminoalkyl, or substituted $C_1-C_6$ aminoalkyl;

In certain embodiments, bicyclic nucleoside having Formula V:

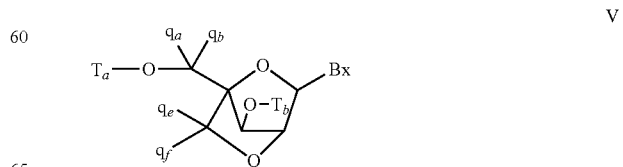

V wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl, or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine, and uracil, along with their oligomerization, and nucleic acid recognition properties have been described (see, e.g., Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA, methyleneoxy (4'-$CH_2$-O-2') BNA, and T-thio-BNAs, have also been prepared (see, e.g., Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel comformationally restricted high-affinity oligonucleotide analog, has been described in the art (see, e.g., Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleoside having Formula VI:

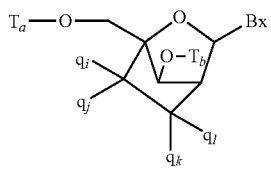

VI wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$, or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl, or substituted $C_1$-$C_{12}$ alkyl.

One carbocyclic bicyclic nucleoside having a 4'-($CH_2$)$_3$-2' bridge and the alkenyl analog, bridge 4'-CH=CH—$CH_2$-2', have been described (see, e.g., Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, oligomeric compounds comprise one or more modified tetrahydropyran nucleoside, which is a nucleoside having a six-membered tetrahydropyran in place of the pentofuranosyl residue in naturally occurring nucleosides. Modified tetrahydropyran nucleosides include, but are not limited to, what is referred to in the art as hexitol nucleic acid (HNA), anitol nucleic acid (ANA), manitol nucleic acid (MNA) (see Leumann, C J., *Bioorg. & Med. Chem.* (2002) 10:841-854), fluoro HNA (F-HNA), or those compounds having Formula VII:

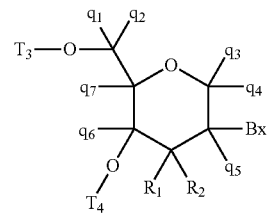

VII wherein independently for each of said at least one tetrahydropyran nucleoside analog of Formula X:

Bx is a heterocyclic base moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula X are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula X are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

In certain embodiments, oligomeric compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., *J. Org. Chem.*, 2003, 68, 4499-4505; Verbeure et al., Nucleic Acids Research, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula VIII.

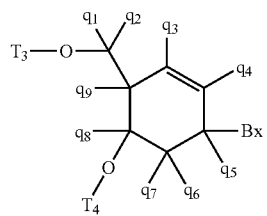

VIII wherein independently for each of said at least one cyclohexenyl nucleoside analog of Formula VIII:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5' or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854). Combinations of these modifications are also provided for herein without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). Such ring systems can undergo various additional substitutions to enhance activity.

Methods for the preparations of modified sugars are well known to those skilled in the art.

In nucleotides having modified sugar moieties, the nucleobase moieties (natural, modified, or a combination thereof) are maintained for hybridization with an appropriate nucleic acid target.

In certain embodiments, antisense compounds comprise one or more nucleotides having modified sugar moieties. In certain embodiments, the modified sugar moiety is 2'-MOE. In certain embodiments, the 2'-MOE modified nucleotides are arranged in a gapmer motif. In certain embodiments, the modified sugar moiety is a cEt (4'-CH($CH_3$)—O-2' BNA). In certain embodiments, the cEt modified nucleosides are arranged throughout the wings of a gapmer motif.

Certain Modified Nucleobases

In certain embodiments, nucleosides of the present invention comprise one or more unmodified nucleobases. In certain embodiments, nucleosides of the present invention comprise one or more modifed nucleobases.

As used herein the terms, "unmodified nucleobase" and "naturally occurring nucleobase" include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (-CC-$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. The term "heterocyclic base moiety" as used herein includes nucleobases and modified nucleobases. Further nucleobases and modified nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

The heterocyclic base moiety of each of the nucleosides can be modified with one or more substituent groups to enhance one or more properties such as affinity for a target strand or affect some other property in an advantageous manner. Modified nucleobases include without limitation, universal bases, hydrophobic bases, promiscuous bases, size-expanded bases, and fluorinated bases as defined herein. Certain of these nucleobases are particularly useful for increasing the binding affinity of the oligomeric compounds as provided herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2 ° C. (*Antisense Research and Applications,* Sanghvi, Y. S., Crooke, S. T. and Lebleu, B., Eds., CRC Press, Boca Raton, 1993, 276-278).

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage.

The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Oligonucleotides having non-phosphorus internucleoside linking groups may be referred to as oligonucleosides. Modified linkages, compared to natural phosphodiester linkages, can be used to alter, typically increase, nuclease resistance of the oligomeric compound. In certain embodiments, internucleoside linkages having a chiral atom can be prepared a racemic mixture, as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids et al. Included in the antisense compounds provided herein are all such possible isomers, as well as their racemic and optically pure forms.

As used herein the phrase "neutral internucleoside linkage" is intended to include internucleoside linkages that are non-ionic. Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research;* Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

Certain Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, terminal groups include, but are not limited to, terminal group nucleosides. In such embodiments, the terminal group nucleosides are differently modified than the terminal nucleoside of the oligonucleotide, thus distinguishing such terminal group nucleosides from the nucleosides of the oligonucleotide.

Certain Motifs

In certain embodiments, the present invention provides oligomeric compounds comprising one or more regions having a particular nucleoside motif. In certain embodiments, the 5'-terminal nucleoside of a modified oligonucleotide of the present invention comprises a compound of Formula II, IIa, IIb, IIc, IId or IIe.

Gapped Motifs

In certain embodiments, the oligomeric compounds of the present invention comprise a gapmer region. In certain such embodiments, the sugar groups of the external regions are the same as one another (referred to herein as a symmetric gapmer). In certain embodiments, the sugar group used in the 5'-external region is different from the sugar group used in the 3'-external region (referred to herein as an asymmetric gapmer). In certain embodiments, the external regions are small (each independently 1, 2, 3, 4 or about 5 monomer subunits) and the monomer subunits comprise non-naturally occurring sugar groups with the internal region comprising f3-D-2'-deoxyribonucleosides. In certain embodiments, the external regions each, independently, comprise from 1 to about 5 monomer subunits having non-naturally occurring sugar groups and the internal region comprises from 6 to 18 unmodified nucleosides. The internal region or the gap generally comprises β-D-2'-deoxyribonucleosides but can comprise non-naturally occurring sugar groups. The heterocyclic base and internucleoside linkage is independently variable at each position of a gapped oligomeric compound. The motif further optionally includes the use of one or more other groups including but not limited to capping groups, conjugate groups and other 5' or 3'-terminal groups.

In certain embodiments, the gapped oligomeric compounds comprise an internal region of β-D-2'-deoxyribonucleosides with one of the external regions comprising modified nucleosides. In certain embodiments, the gapped oligomeric compounds comprise an internal region of β-D-2'-deoxyribonucleosides with both of the external regions comprising modified nucleosides. In certain embodiments, gapped oligomeric compounds are provided herein wherein all of the monomer subunits comprise non-naturally occurring sugar groups.

In certain embodiments, gapped oligomeric compounds are provided comprising one or two modified nucleosides at the 5'-end, two or three modified nucleosides at the 3'-end and an internal region of from 10 to 16 β-D-2'-deoxyribonucleosides. In certain embodiments, gapped oligomeric compounds are provided comprising one modified nucleoside at the 5'-end, two modified nucleosides at the 3'-end and an internal region of from 10 to 16 β-D-2'-deoxyribonucleosides. In certain embodiments, gapped oligomeric compounds are provided comprising one modified nucleosides at the 5'-end, two modified nucleosides at the 3'-end and an internal region of from 10 to 14 β-D-2'-deoxyribonucleosides.

In certain embodiments, gapped oligomeric compounds are provided that are from about 10 to about 21 monomer subunits in length. In certain embodiments, gapped oligomeric compounds are provided that are from about 12 to about 16 monomer subunits in length. In certain embodiments, gapped oligomeric compounds are provided that are from about 12 to about 14 monomer subunits in length.

Certain Alternating Regions

In certain embodiments, oligonucleotides of the present invention comprise one or more regions of alternating modifications. In certain embodiments, oligonucleotides comprise one or more regions of alternating nucleoside modifications. In certain embodiments, oligonucleotides comprise one or more regions of alternating linkage modifications. In certain embodiments, oligonucleotides comprise one or more regions of alternating nucleoside and linkage modifications.

In certain embodiments, oligonucleotides of the present invention comprise one or more regions of alternating 2'-F modified nucleosides and 2'-OMe modified nucleosides. In certain such embodiments, such regions of alternating 2'F modified and 2'OMe modified nucleosides also comprise alternating linkages. In certain such embodiments, the linkages at the 3' end of the 2'-F modified nucleosides are phosphorothioate linkages. In certain such embodiments, the linkages at the 3'end of the 2'OMe nucleosides are phosphodiester linkages. In certain embodiments, such alternating regions are: (2'-F)-(PS)-(2'-OMe)-(PO).

In certain embodiments, oligomeric compounds comprise 2, 3, 4, 5, 6, 7, 8, 9, 10, or 11 such alternating regions. Such regions may be contiguous or may be interupted by differently modified nucleosides or linkages.

In certain embodiments, one or more alternating regions in an alternating motif include more than a single nucleoside of a type. For example, oligomeric compounds of the present invention may include one or more regions of any of the following nucleoside motifs:

AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, BNA, DNA, and MOE.

In certain embodiments, A is DNA. In certain embodiments, B is 4'-CH$_2$O-2'-BNA. In certain embodiments, A is DNA and B is 4'-CH$_2$O-2'-BNA. In certain embodiments A is 4'-CH$_2$O-2'-BNA, B is DNA. In certain embodiments A is 4'-CH$_2$O-2'-BNA and B is DNA. In certain embodiments, A is 2'-F. In certain embodiments, B is 2'-OMe. In certain embodiments, A is 2'-F and B is 2'-OMe. In certain embodiemtns, A is 2'-OMe. In certain embodiments, B is 2'-F. In certain embodiments, A is 2'-OMe and B is 2'-F. In certain embodiments, A is DNA and B is 2'-OMe. In certain embodiments, A is 2'-OMe and B is DNA.

In certain embodiments, oligomeric compounds having such an alternating motif also comprise a 5' terminal nucleoside of formula II, IIa, IIb, IIc, IId or IIe.

Two-Two-Three Motifs

In certain embodiments, oligonucleotides of the present invention comprise a region having a 2-2-3 motif. Such regions comprises the following motif:

5'- (Formula II, IIa, IIb, IIc, IId or IIe)-(E)$_w$-(A)$_2$-(B)$_x$-(A)$_2$-(C)$_y$-(A)$_3$-(D)$_z$ wherein: A is a first type of modifed nucleosde;

B, C, D, and E are nucleosides that are differently modified than A, however, B, C, D, and E may have the same or different modifications as one another;

w and z are from 0 to 15;

x and y are from 1 to 15.

In certain embodiments, A is a 2'-OMe modified nucleoside. In certain embodiments, B, C, D, and E are all 2'-F modified nucleosides. In certain embodiments, A is a 2'-OMe modified nucleoside and B, C, D, and E are all 2'-F modified nucleosides.

In certain embodiments, the linkages of a 2-2-3 motif are all modifed linkages. In certain embodiments, the linkages are all phosphorothioate linkages. In certain embodiemtns, the linkages at the 3'-end of each modification of the first type are phosphodiester.

In certain embodiments, Z is 0. In such embodiments, the region of three nucleosides of the first type are at the 3'-end of the oligonucleotide. In certain embodiments, such region is at the 3'-end of the oligomeric compound, with no additional groups attached to the 3' end of the region of three nucleosides of the first type. In certain embodiments, an oligomeric compound comprising an oligonucleotide where Z is 0, may comprise a terminal group attached to the 3'-terminal nucleoside. Such terminal groups may include additional nucleosides. Such additional nucleosides are typically non-hybridizing nucleosides.

In certain embodiments, Z is 1-3. In certain embodiments, Z is 2. In certain embodiments, the nucleosides of Z are 2'-MOE nucleosides. In certain embodiments, Z represents non-hybridizing nucleosides. To avoid confusion, it is noted that such non-hybridizing nucleosides might also be described as a 3'-terminal group with Z=0.

Combinations of Motifs

It is to be understood, that certain of the above described motifs and modifications may be combined. Since a motif may comprises only a few nucleosides, a particular oligonucleotide may comprise two or more motifs. By way of non-limiting example, in certain embodiments, oligomeric compounds may have nucleoside motifs as described in the table below. In the table below, the term "None" indicates that a particular feature is not present in the oligonucleotide. For example, "None" in the column labeled "5' motif/modification" indicates that the 5' end of the oligonucleotide comprises the first nucleoside of the central motif.

| 5' motif/modification | Central Motif | 3'-motif |
|---|---|---|
| Compound of Formula II, IIa, IIb, IIc, IId or IIe | Alternating | 2 MOE nucleosides |
| Compound of Formula II, IIa, IIb, IIc, IId or IIe | 2-2-3 motif | 2 MOE nucleosides |
| Compound of Formula II, IIa, IIb, IIc, IId or IIe | Uniform | 2 MOE nucleosides |
| Compound of Formula II, IIa, IIb, IIc, IId or IIe | Alternating | 2 MOE nucleosides |
| Compound of Formula II, IIa, IIb, IIc, IId or IIe | Alternating | 2 MOE A's |
| Compound of Formula II, IIa, IIb, IIc, IId or IIe | 2-2-3 motif | 2 MOE A's |
| Compound of Formula II, IIa, IIb, IIc, IId or IIe | Uniform | 2 MOE A's |
| Compound of Formula II, IIa, IIb, IIc, IId or IIe | Alternating | 2 MOE U's |
| Compound of Formula II, IIa, IIb, IIc, IId or IIe | 2-2-3 motif | 2 MOE U's |
| Compound of Formula II, IIa, IIb, IIc, IId or IIe | Uniform | 2 MOE U's |
| Compound of Formula II, IIa, IIb, IIc, IId or IIe | Alternating | 2 MOE nucleosides |
| Compound of Formula II, IIa, IIb, IIc, IId or IIe | 2-2-3 motif | 2 MOE nucleosides |
| Compound of Formula II, IIa, IIb, IIc, IId or IIe | Uniform | 2 MOE nucleosides |

Oligomeric compounds having any of the various nucleoside motifs described herein, may have any linkage motif. For example, the oligomeric compounds, including but not limited to those described in the above table, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS |

As is apparent from the above, non-limiting tables, the lengths of the regions defined by a nucleoside motif and that of a linkage motif need not be the same. For example, the 3'region in the nucleoside motif table above is 2 nucleosides, while the 3'-region of the linkage motif table above is 6-8 nucleosides. Combining the tables results in an oligonucleotide having two 3'-terminal MOE nucleosides and six to eight 3'-terminal phosphorothioate linkages (so some of the linkages in the central region of the nucleoside motif are phosphorothioate as well). To further illustrate, and not to limit in any way, nucleoside motifs and sequence motifs are combined to show five non-limiting examples in the table below. The first column of the table lists nucleosides and linkages by position from N1 (the first nucleoside at the 5'-end) to N20 (the 20$^{th}$ position from the 5'-end). In certain embodiments, oligonucleotides of the present invention are longer than 20 nucleosides (the table is merely exemplary). Certain positions in the table recite the nucleoside or linkage "none" indicating that the oligonucleotide has no nucleoside at that position.

| Pos | A | B | C | D | E |
|---|---|---|---|---|---|
| N1 | Formula II, IIa, IIb, IIc, IId or IIe | Formula II, IIa, IIb, IIc, IId or IIe | Formula II, IIa, IIb, IIc, IId or IIe | Formula II, IIa, IIb, IIc, IId or IIe | Formula II, IIa, IIb, IIc, IId or IIe |
| L1 | PS | PS | PS | PS | PO |
| N2 | 2'-F | 2'-F | 2'-F | 2'-OMe | MOE |
| L2 | PS | PS | PS | PO | PS |
| N3 | 2'-OMe | 2'-F | 2'-F | 2'-F | 2'-F |
| L3 | PO | PS | PS | PS | PS |
| N4 | 2'-F | 2'-F | 2'-F | 2'-OMe | 2'-F |
| L4 | PS | PS | PS | PO | PS |
| N5 | 2'-OMe | 2'-F | 2'-F | 2'-F | 2'-OMe |
| L5 | PO | PS | PS | PS | PO |
| N6 | 2'-F | 2'-OMe | 2'-F | 2'-OMe | 2'-OMe |
| L6 | PS | PO | PS | PO | PO |
| N7 | 2'-OMe | 2'-OMe | 2'-F | 2'-F | 2'-OMe |
| L7 | PO | PO | PS | PS | PO |
| N8 | 2'-F | 2'-F | 2'-F | 2'-OMe | 2'-F |
| L8 | PS | PS | PS | PO | PS |
| N9 | 2'-OMe | 2'-F | 2'-F | 2'-F | 2'-F |
| L9 | PO | PS | PS | PS | PS |
| N10 | 2'-F | 2'-OMe | 2'-F | 2'-OMe | 2'-OMe |
| L10 | PS | PO | PS | PO | PO |
| N11 | 2'-OMe | 2'-OMe | 2'-F | 2'-F | 2'OMe |
| L11 | PO | PO | PS | PS | PO |
| N12 | 2'-F | 2'-F | 2'-F | 2'-F | 2'-F |
| L12 | PS | PS | PS | PO | PS |
| N13 | 2'-OMe | 2'-F | 2'-F | 2'-F | 2'-F |
| L13 | PO | PS | PS | PS | PS |
| N14 | 2'-F | 2'-OMe | 2'-F | 2'-F | 2'-F |
| L14 | PS | PS | PS | PS | PS |
| N15 | 2'-OMe | 2'OMe | 2'-F | 2'-F | 2'-MOE |
| L15 | PS | PS | PS | PS | PS |
| N16 | 2'-F | 2'OMe | 2'-F | 2'-F | 2'-MOE |
| L16 | PS | PS | PS | PS | PS |
| N17 | 2'-OMe | 2'-MOE U | 2'-F | 2'-F | 2'-MOE |
| L17 | PS | PS | PS | PS | None |
| N18 | 2'-F | 2'-MOE U | 2'-F | 2'-OMe | None |
| L18 | PS | None | PS | PS | None |
| N19 | 2'-MOE U | None | 2'-MOE U | 2'-MOE A | None |

-continued

| Pos | A | B | C | D | E |
|-----|---|---|---|---|---|
| L19 | PS | None | PS | PS | None |
| N20 | 2'-MOE U | None | 2'-MOE U | 2'-MOE A | None |

In the above, non-limiting examples:

Column A represent an oligomeric compound consisting of 20 linked nucleosides, wherein the oligomeric compound comprises: a modified 5'-terminal nucleoside of Formula II, IIa, IIb, IIc, IId or IIe; a region of alternating nucleosides; a region of alternating linkages; two 3'-terminal MOE nucleosides, each of which comprises a uracil base; and a region of six phosphorothioate linkages at the 3'-end.

Column B represents an oligomeric compound consisting of 18 linked nucleosides, wherein the oligomeric compound comprises: a modified 5'-terminal nucleoside of Formula II, IIa, IIb, IIc, IId or IIe; a 2-2-3 motif wherein the modified nucleoside of the 2-2-3 motif are 2'O-Me and the remaining nucleosides are all 2'-F; two 3'-terminal MOE nucleosides, each of which comprises a uracil base; and a region of six phosphorothioate linkages at the 3'-end.

Column C represents an oligomeric compound consisting of 20 linked nucleosides, wherein the oligomeric compound comprises: a modified 5'-terminal nucleoside of Formula II, IIa, IIb, IIc, IId or IIe; a region of uniformly modified 2'-F nucleosides; two 3'-terminal MOE nucleosides, each of which comprises a uracil base; and wherein each internucleoside linkage is a phosphorothioate linkage.

Column D represents an oligomeric compound consisting of 20 linked nucleosides, wherein the oligomeric compound comprises: a modified 5'-terminal nucleoside of Formula II, IIa, IIb, IIc, IId or IIe; a region of alternating 2'-OMe/2'-F nucleosides; a region of uniform 2'F nucleosides; a region of alternating phosphorothioate/phosphodiester linkages; two 3'-terminal MOE nucleosides, each of which comprises an adenine base; and a region of six phosphorothioate linkages at the 3'-end.

Column E represents an oligomeric compound consisting of 17 linked nucleosides, wherein the oligomeric compound comprises: a modified 5'-terminal nucleoside of Formula II, IIa, IIb, IIc, IId or IIe; a 2-2-3 motif wherein the modified nucleoside of the 2-2-3 motif are 2'F and the remaining nucleosides are all 2'-OMe; three 3'-terminal MOE nucleosides.

The above examples are provided solely to illustrate how the described motifs may be used in combination and are not intended to limit the invention to the particular combinations or the particular modifications used in illustrating the combinations. Further, specific examples herein, including, but not limited to those in the above table are intended to encompass more generic embodiments. For example, column A in the above table exemplifies a region of alternating 2'-OMe and 2'-F nucleosides. Thus, that same disclosure also exemplifies a region of alternating different 2'-modifications. It also exemplifies a region of alternating 2'-O-alkyl and 2'-halogen nucleosides. It also exemplifies a region of alternating differently modified nucleosides. All of the examples throughout this specification contemplate such generic interpretation.

It is also noted that the lengths of oligomeric compounds, such as those exemplified in the above tables, can be easily manipulated by lengthening or shortening one or more of the described regions, without disrupting the motif.

In certain embodiments, the invention provides oligomeric compounds wherein the 5'-terminal nucleoside (position 1) is a compound of Formula II, IIa, IIb, IIc, IId or IIe and the position 2 nucleoside comprises a 2'-modification. In certain such embodiments, the 2'-modification of the position 2 nucleoside is selected from halogen, alkyl, and substituted alkyl. In certain embodiments, the 2'-modification of the position 2 nucleoside is selected from 2'-F and 2'-alkyl. In certain embodiments, the 2'-modification of the position 2 nucleoside is 2'-F. In certain embodiments, the 2'-substitued of the position 2 nucleoside is an unmodified OH (as in naturally occurring RNA).

In certain embodiments, the position 3 nucleoside is a modified nucleoside. In certain embodiments, the position 3 nucleoside is a bicyclic nucleoside. In certain embodiments, the position 3 nucleoside comprises a sugar surrogate. In certain such embodiments, the sugar surrogate is a tetrahydropyran. In certain embodiments, the sugar of the position 3 nucleoside is a F-HNA.

In certain embodiments, an antisense oligomeric compound comprises an oligonucleotide comprising 10 to 30 linked nucleosides wherein the oligonucleotide comprises: a position 1 modified nucleoside of Formula II, IIa, IIb, IIc, IId or IIe; a position 2 nucleoside comprising a sugar moiety which is differently modified compared to the sugar moiety of the position 1 modified nucleoside; and from 1 to 4 3'-terminal group nucleosides each comprising a 2'-modification; and wherein at least the seven 3'-most internucleoside linkages are phosphorothioate linkages.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Phannacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130.

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779;4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-l-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above.

Thus, for example, an oligomeric compound comprising an oligonucleotide having region of alternating nucleosides may comprise a terminal group.

Antisense Compounds

In certain embodiments, oligomeric compounds of the present invention are antisense compounds. In such embodiments, the oligomeric compound is complementary to a target nucleic acid. In certain embodiments, a target nucleic acid is an RNA. In certain embodiments, a target nucleic acid is a non-coding RNA. In certain embodiments, a target nucleic acid encodes a protein. In certain embodiments, a target nucleic acid is selected from a mRNA, a pre-mRNA, a microRNA, a non-coding RNA, including small non-coding RNA, and a promoter-directed RNA. In certain embodiments, oligomeric compounds are at least partially complementary to more than one target nucleic acid. For example, oligomeric compounds of the present invention may be microRNA mimics, which typically bind to multiple targets.

Antisense mechanisms include any mechanism involving the hybridization of an oligomeric compound with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

Antisense mechanisms also include, without limitation RNAi mechanisms, which utilize the RISC pathway. Such RNAi mechanisms include, without limitation siRNA, ssRNA and microRNA mechanisms. Such mechanism include creation of a microRNA mimic and/or an anti-microRNA.

Antisense mechanisms also include, without limitation, mechanisms that hybridize or mimic non-coding RNA other than microRNA or mRNA. Such non-coding RNA includes, but is not limited to promoter-directed RNA and short and long RNA that effects transcription or translation of one or more nucleic acids.

In certain embodiments, antisense compounds specifically hybridize when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In certain embodiments, oligomeric compounds of the present invention are RNAi compounds. In certain embodiments, oligomeric compounds of the present invention are ssRNA compounds. In certain embodiments, oligomeric compounds of the present invention are paired with a second oligomeric compound to form an siRNA. In certain such embodiments, the second oligomeric compound is also an oligomeric compound of the present invention. In certain embodiments, the second oligomeric compound is any modified or unmodified nucleic acid. In certain embodiments, the oligomeric compound of the present invention is the antisense strand in an siRNA compound. In certain embodiments, the oligomeric compound of the present invention is the sense strand in an siRNA compound.

Single-Stranded Antisense Compounds

In certain embodiments, oligomeric compounds of the present invention are particularly suited for use as single-stranded antisense compounds. In certain such embodiments, such oligomeric compounds are single-stranded RNAi compounds. In certain embodiments, such oligomeric compounds are ssRNA compounds or microRNA mimics. Certain 5'-terminal nucleosides described herein are suited for use in such single-stranded oligomeric compounds. In certain embodiments, such 5'-terminal nucleosides stabilize the 5'-phosphorous moiety. In certain embodiments, 5'-terminal nucleosides of the present invention are resistant to nucleases. In certain embodiments, the motifs of the present invention are particularly suited for use in single-stranded oligomeric compounds.

Use of single-stranded RNAi compounds has been limited. In certain instances, single stranded RNAi compounds are quickly degraded and/or do not load efficiently into RISC. Certain compounds of the present invention possess properties superior to previously described ssRNAi compounds. In certain embodiments, oligomeric compounds of the present invention are superior ssRNAi compounds in vitro. In certain such embodiments, the 5'-terminal phosphorous moiety is stabilized. In certain such embodiments, the 5'-nucleoside is resistant to nuclease cleavage. In certain embodiments, the 5'-terminal end loads efficiently into RISC. In certain embodiments, the motif stabilizes the oligomeric compound. In certain embodiments the 3'-terminal end of the oligomeric compound is stabilized.

Design of single-stranded RNAi compounds for use in cells and/or for use in vivo presents several challenges. For example, the compound must be chemically stable, resistant to nuclease degradation, capable of entering cells, capable of loading into RISC (e.g., binding Ago1 or Ago2), capable of hybridizing with a target nucleic acid, and not toxic to cells or animals. In certain instances, a modification or motif that improves one such feature may worsen another feature, rendering a compound having such modification or motif unsuitable for use as an RNAi compound. For example, certain modifications, particularly if placed at or near the 5'-end of an oligomeric compound, may make the compound more stable and more resistant to nuclease degradation, but may also inhibit or prevent loading into RISC by blocking the interaction with RISC components, such as Ago1 or Ago2. Despite its improved stability properties, such a compound would be unsuitable for use in RNAi. Thus, the challenge is to identify modifications and combinations and placement of modifications that satisfy each parameter at least sufficient to provide a functional single-stranded RNAi compound. In certain embodiments, oligomeric compounds of the present invention combine modifications to provide single-stranded RNAi compounds that are active as single-stranded RNAi compounds.

In certain instances, a single-stranded oligomeric compound comprising a 5'-phosphorous moiety is desired. For example, in certain embodiments, such 5'-phosphorous moiety is necessary or useful for RNAi compounds, particularly, single-stranded RNAi compounds. In such instances, it is further desirable to stabilize the phosphorous moiety against degradation or de-phosphorylation, which may inactivate the compound. Further, it is desirable to stabilize the entire 5'-nucleoside from degradation, which could also inactivate the compound. Thus, in certain embodiments, oligonucleotides in which both the 5'-phosphorous moiety and the 5'-nucleoside have been stabilized are desired. In certain embodiments, the present invention provides modified nucleosides that may be placed at the 5'-end of an oligomeric compound, resulting in stabilized phosphorous and stabilized nucleoside. In certain such embodiments, the phosphorous moiety is resistant to removal in biological systems, relative to unmodified nucleosides and/or the 5'-nucleoside is resistant to cleavage by nucleases. In certain embodiments, such nucleosides are modified at one, at two or at all three of: the 2'-position, the 5'-position, and at the phosphorous moiety. Such modified nucleosides may be incorporated at the 5'-end of an oligomeric compound.

Although certain oligomeric compounds of the present invention have particular use as single-stranded compounds, such compounds may also be paired with a second strand to create a double-stranded oligomeric compound. In such embodiments, the second strand of the double-stranded duplex may or may not also be an oligomeric compound of the present invention.

In certain embodiments, oligomeric compounds of the present invention bind and/or activate one or more nucleases. In certain embodiments, such binding and/or activation ultimately results in antisense activity. In certain embodiments, an oligomeric compound of the invention interacts with a target nucleic acid and with a nuclease, resulting in activation of the nuclease and cleavage of the target nucleic acid. In certain embodiments, an oligomeric compound of the invention interacts with a target nucleic acid and with a nuclease, resulting in activation of the nuclease and inactivation of the target nucleic acid. In certain embodiments, an oligomeric compound of the invention forms a duplex with a target nucleic acid and that duplex activates a nuclease, resulting in cleavage and/or inactivation of one or both of the oligomeric compound and the target nucleic acid. In certain embodiments, an oligomeric compound of the invention binds and/or activates a nuclease and the bound and/or activated nuclease cleaves or inactivates a target nucleic acid. Nucleases include, but are not limited to, ribonucleases (nucleases that specifically cleave ribonucleotides), double-strand nucleases (nucleases that specifically cleave one or both strands of a double-stranded duplex), and double-strand ribonucleases. For example, nucleases include, but are not limited to RNase H, an argonaute protein (including, but not limited to Ago2), and dicer.

In certain embodiments, oligomeric compounds of the present invention interact with an argonaute protein (Ago). In certain embodiments, such oligomeric compounds first enter the RISC pathway by interacting with another member of the pathway (e.g., dicer). In certain embodiments, oligomeric compounds first enter the RISC pathway by interacting with Ago. In certain embodiments, such interaction ultimately results in antisense activity. In certain embodiments, the invention provides methods of activating Ago comprising contacting Ago with an oligomeric compound. In certain embodiments, such oligomeric compounds comprise a modified 5'-phosphate group. In certain embodiments, the invention provides methods of modulating the expression or amount of a target nucleic acid in a cell comprising contacting the cell with an oligomeric compound capable of activating Ago, ultimately resulting in cleavage of the target nucleic acid. In certain embodiments, the cell is in an animal. In certain embodiments, the cell is in vitro. In certain embodiments, the methods are performed in the presence of manganese. In certain embodiments, the manganese is endogenous. In certain embodiment the methods are performed in the absence of magnesium. In certain embodiments, the Ago is endogenous to the cell. In certain such embodiments, the cell is in an animal. In certain embodiments, the Ago is human Ago. In certain embodiments, the Ago is Ago2. In certain embodiments, the Ago is human Ago2.

In certain embodiments, oligomeric compounds of the present invention interact with the enzyme dicer. In certain such embodiments, oligomeric compounds bind to dicer and/or are cleaved by dicer. In certain such embodiments, such interaction with dicer ultimately results in antisense activity. In certain embodiments, the dicer is human dicer. In certain embodiments, oligomeric compounds that interact with dicer are double-stranded oligomeric compounds. In certain embodiments, oligomeric compounds that interact with dicer are single-stranded oligomeric compounds.

In embodiments in which a double-stranded oligomeric compound interacts with dicer, such double-stranded oligomeric compound forms a dicer duplex. In certain embodiments, any oligomeric compound described herein may be suitable as one or both strands of a dicer duplex. In certain embodiments, each strand of the dicer duplex is an oligomeric compound of the present invention. In certain embodiments, one strand of the dicer duplex is an oligomeric compound of the present invention and the other strand is any modified or unmodified oligomeric compound. In certain embodiments, one or both strands of a dicer duplex comprises a nucleoside of Formula II, IIa, IIb, IIc, IId or IIe at the 5' end. In certain embodiments, one strand of a dicer duplex is an antisense oligomeric compound and the other strand is its sense complement.

In certain embodiments, the dicer duplex comprises a 3'-overhang at one or both ends. In certain embodiments, such overhangs are additional nucleosides. In certain embodiments, the dicer duplex comprises a 3' overhang on the sense oligonucleotide and not on the antisense oligonucleotide. In certain embodiments, the dicer duplex comprises a 3' overhang on the antisense oligonucleotide and not on the sense oligonucleotide. In certain embodiments, 3'overhangs of a dicer duplex comprise 1-4 nucleosides. In certain embodiments, such overhangs comprise two nucleosides. In certain embodiments, the nucleosides in the 3'-overhangs comprise purine nucleobases. In certain embodiments, the nucleosides in the 3' overhangs comprise adenine nucleobases. In certain embodiments, the nucleosides in the 3' overhangs comprise pyrimidines. In certain embodiments, dicer duplexes comprising 3'-purine overhangs are more active as antisense compounds than dicer duplexes comprising 3' pyrimidine overhangs, In certain embodiments, oligomeric compounds of a dicer duplex comprise one or more 3' deoxy nucleosides. In certain such embodiments, the 3' deoxy nucleosides are dT nucleosides.

In certain embodiments, the 5' end of each strand of a dicer duplex comprises a phosphate moiety. In certain embodiments the antisense strand of a dicer duplex comprises a phosphate moiety and the sense strand of the dicer duplex does not comprise a phosphate moiety. In certain embodiments the sense strand of a dicer duplex comprises a phosphate moiety and the antisense strand of the dicer duplex does not comprise a phosphate moiety. In certain embodiments, a dicer duplex does not comprise a phosphate moiety at the 3' end. In certain embodiments, a dicer duplex is cleaved by dicer. In such embodiments, dicer duplexes do not comprise 2'-OMe modifications on the nucleosides at the cleavage site. In certain embodiments, such cleavage site nucleosides are RNA.

In certain embodiments, interaction of an oligomeric compound with dicer ultimately results in antisense activity. In certain embodiments, dicer cleaves one or both strands of a double-stranded oligomeric compound and the resulting product enters the RISC pathway, ultimately resulting in antisense activity. In certain embodiments, dicer does not cleave either strand of a double-stranded oligomeric compound, but nevertheless facilitates entry into the RISC pathway and ultimately results in antisense activity. In certain embodiments, dicer cleaves a single-stranded oligomeric compound and the resulting product enters the RISC pathway, ultimately resulting in antisense activity. In certain embodiments, dicer does not cleave the single-stranded oligomeric compound, but nevertheless facilitates entry into the RISC pathway and ultimately results in antisense activity.

In certain embodiments, the invention provides methods of activating dicer comprising contacting dicer with an oligomeric compound. In certain such embodiments, the dicer is in a cell. In certain such embodiments, the cell is in an animal.

Dicer

In certain embodiments, oligomeric compounds of the present invention interact with the enzyme dicer. In certain such embodiments, oligomeric compounds bind to dicer and/or are cleaved by dicer. In certain such embodiments, such interaction with dicer ultimately results in antisense activity. In certain embodiments, the dicer is human dicer. In certain embodiments, oligomeric compounds that interact with dicer are double-stranded oligomeric compounds. In certain embodiments, oligomeric compounds that interact with dicer are single-stranded oligomeric compounds.

In embodiments in which a double-stranded oligomeric compound interacts with dicer, such double-stranded oligomeric compound forms a dicer duplex. In certain embodiments, any oligomeric compound described herein may be suitable as one or both strands of a dicer duplex. In certain embodiments, each strand of the dicer duplex is an oligomeric compound of the present invention. In certain embodiments, one strand of the dicer duplex is an oligomeric compound of the present invention and the other strand is any modified or unmodified oligomeric compound. In certain embodiments, one or both strands of a dicer duplex comprises a nucleoside of Formula II, IIa, IIb, IIc, IId or IIe at the 5'. In certain embodiments, one strand of a dicer duplex is an antisense oligomeric compound and the other strand is its sense complement.

In certain embodiments, the invention provides single-stranded oligomeric compounds that interact with dicer. In certain embodiments, such single-stranded dicer compounds comprise a nucleoside of Formula II, IIa, IIb, IIc, IId or IIe. In certain embodiments, single-stranded dicer compounds do not comprise a phosphorous moiety at the 3'-end. In certain embodiments, such single-stranded dicer compounds may comprise a 3'-overhangs. In certain embodiments, such 3'-overhangs are additional nucleosides. In certain embodiments, such 3'-overhangs comprise 1-4 additional nucleosides that are not complementary to a target nucleic acid and/or are differently modified from the adjacent 3' nucleoside of the oligomeric compound. In certain embodiments, a single-stranded oligomeric compound comprises an antisense oligonucleotide having two 3'-end overhang nucleosides wherein the overhang nucleosides are adenine or modified adenine nucleosides. In certain embodiments, single stranded oligomeric compounds that interact with dicer comprise a nucleoside of Formula II, IIa, IIb, IIc, IId or IIe In certain embodiments, interaction of an oligomeric compound with dicer ultimately results in antisense activity. In certain embodiments, dicer cleaves one or both strands of a double-stranded oligomeric compound and the resulting product enters the RISC pathway, ultimately resulting in antisense activity. In certain embodiments, dicer does not cleave either strand of a double-stranded oligomeric compound, but nevertheless facilitates entry into the RISC pathway and ultimately results in antisense activity. In certain embodiments, dicer cleaves a single-stranded oligomeric compound and the resulting product enters the RISC pathway, ultimately resulting in antisense activity. In certain embodiments, dicer does not cleave the single-stranded oligomeric compound, but nevertheless facilitates entry into the RISC pathway and ultimately results in antisense activity.

In certain embodiments, the invention provides methods of activating dicer comprising contacting dicer with an oligomeric compound. In certain such embodiments, the dicer is in a cell. In certain such embodiments, the cell is in an animal.

Ago

In certain embodiments, oligomeric compounds of the present invention interact with Ago. In certain embodiments, such oligomeric compounds first enter the RISC pathway by interacting with another member of the pathway (e.g., dicer). In certain embodiments, oligomeric compounds first enter the RISC pathway by interacting with Ago. In certain embodiments, such interaction ultimately results in antisense activity. In certain embodiments, the invention provides methods of activating Ago comprising contacting Ago with an oligomeric compound. In certain such embodiments, the Ago is in a cell. In certain such embodiments, the cell is in an animal.

Oligomeric Compound Identity

In certain embodiments, a portion of an oligomeric compound is 100% identical to the nucleobase sequence of a microRNA, but the entire oligomeric compound is not fully identical to the microRNA. In certain such embodiments, the length of an oligomeric compound having a 100% identical portion is greater than the length of the microRNA. For example, a microRNA mimic consisting of 24 linked nucleosides, where the nucleobases at positions 1 through 23 are each identical to corresponding positions of a microRNA that is 23 nucleobases in length, has a 23 nucleoside portion that is 100% identical to the nucleobase sequence of the microRNA and has approximately 96% overall identity to the nucleobase sequence of the microRNA.

In certain embodiments, the nucleobase sequence of oligomeric compound is fully identical to the nucleobase sequence of a portion of a microRNA. For example, a single-stranded microRNA mimic consisting of 22 linked nucleosides, where the nucleobases of positions 1 through 22 are each identical to a corresponding position of a microRNA that is 23 nucleobases in length, is fully identical to a 22 nucleobase portion of the nucleobase sequence of the microRNA. Such a single-stranded microRNA mimic has approximately 96% overall identity to the nucleobase sequence of the entire microRNA, and has 100% identity to a 22 nucleobase portion of the microRNA.

Synthesis of Monomeric and Oligomeric Compounds

The nucleosides provided herein can be prepared by any of the applicable techniques of organic synthesis, as, for example, illustrated in the examples below. Many such techniques are well known in the art. However, many of the known techniques are elaborated in *Compendium of Organic Synthetic Methods,* John Wiley & Sons, New York: Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade Jr., 1980; Vol. 5, Leroy G. Wade Jr., 1984; and Vol. 6, Michael B. Smith; as well as March, J., *Advanced Organic Chemistry,* 3rd Edition, John Wiley & Sons, New York, 1985; *Comprehensive Organic Synthesis. Selectivity, Strategy & Efficiency in Modern Organic Chemistry,* in 9 Volumes, Barry M. Trost, Editor-in-Chief, Pergamon Press, New York, 1993; *Advanced Organic Chemistry, Part B: Reactions and Synthesis,* 4th Edition; Carey and Sundberg, Kluwer Academic/Plenum Publishers, New York, 2001; *Advanced Organic Chemistry, Reactions, Mechanisms, and Structure,* 2nd Edition, March, McGraw Hill, 1977; Greene, T. W., and Wutz, P. G. M., *Protecting Groups in Organic Synthesis,* 4th Edition, John Wiley & Sons, New York, 1991; and Larock, R. C., *Comprehensive Organic Transformations,* 2nd Edition, John Wiley & Sons, New York, 1999.

The compounds described herein contain one or more asymmetric centers and thus give rise to enantiomers, diastereomers, and other stereoisomeric forms that may be defined, in terms of absolute stereochemistry, as (R)- or (S)-, $\alpha$ or $\beta$, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions,* John Wiley & Sons, 1981. When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to limit a particular configuration unless the text so states.

In certain embodiments, the preparation of oligomeric compounds as disclosed herein is performed according to literature procedures for DNA: Protocols for Oligonucleotides and Analogs, Agrawal, Ed., Humana Press, 1993, and/ or RNA: Scaringe, *Methods,* 2001, 23, 206-217; Gait et al., *Applications of Chemically synthesized RNA in RNA:Protein Interactions,* Smith, Ed., 1998, 1-36; Gallo et al., *Tetrahedron* , 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Synthesis of Oligomeric Compounds

Oligomeric compounds are routinely prepared using solid support methods as opposed to solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in Oligonucleotides and Analogues, a Practical Approach, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl(TBDMS), 5'O-DMT-2'-O-[1(2-fluorophenyl)-4-methoxypiperidin-4-yl] (FPMP), 2'-O-[(triisopropylsilyl)oxy]methyl (2'-O—CH$_2$—O—Si(iPr)$_3$ (TOM) and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dhannacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilyl)oxy]methyl; DOD/ACE: (5'-O-bis(trimethylsiloxy)cyclo-dodecyloxysilyl ether-2'-O-bis(2-acetoxyethoxy)methyl; and FPMP: 5'-O-DMT-2'-O-[1(2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

Compositions and Methods for Formulating Pharmaceutical Compositions

Oligomeric compounds may be admixed with pharmaceutically acceptable active and/or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Oligomeric compounds, including antisense compounds, can be utilized in pharmaceutical compositions by combining such oligomeric compounds with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in certain embodiments, employed in the methods described herein is a pharmaceutical composition comprising an antisense compound and a pharmaceutically acceptable diluent. In certain embodiments, the pharmaceutically acceptable diluent is PBS.

Pharmaceutical compositions comprising oligomeric compounds encompass any pharmaceutically acceptable salts, esters, or salts of such esters. In certain embodiments, pharmaceutical compositions comprising oligomeric compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active oligomeric compound.

Lipid-based vectors have been used in nucleic acid therapies in a variety of methods. In one method, the nucleic acid is introduced into preformed liposomes or lipoplexes made of mixtures of cationic lipids and neutral lipids. In another method, DNA complexes with mono- or poly-cationic lipids are formed without the presence of a neutral lipid.

In certain methods, preparations are made that include a polyamine compound or a lipid moiety complexed with a nucleic acid. Such preparations are described in PCT publication WO/2008/042973; and in Akinc et al:, Nature Biotechnology 26, 561-569 (May 1, 2008), which are herein incorporated by reference in their entirety.

Certain Methods/Uses

In certain embodiments, the present invention provides compounds and methods for reducing the amount or activity of a target nucleic acid. In certain embodiments, the invention provides antisense compounds and methods. In certain embodiments, the invention provides antisense compounds and methods based on activation of RNase H. In certain embodiments, the invention provides RNAi compounds and methods.

In certain instances it is desirable to use an antisense compound that functions at least in part through RISC. In certain such instances unmodified RNA, whether single-stranded or double stranded is not suitable. Single-stranded RNA is relatively unstable and double-stranded RNA does not easily enter cells. The challenge has been to identify modifications and motifs that provide desirable properties, such as improved stability, without interfering with (and possibly even improving upon) the antisense activity of RNA through RNAi.

In certain embodiments, the present invention provides oligonucleotides having motifs (nucleoside motifs and/or linkage motifs) that result in improved properties. Certain such motifs result in single-stranded oligonucleotides with improved stability and/or cellular uptake properties while retaining antisense activity. For example, oligonucleotides having an alternating nucleoside motif and seven phosphorothioate linkages at to 3'-terminal end have improved stability and activity. Similar compounds that comprise phosphorothioate linkages at each linkage have further improved stability, but are not active as RNAi compounds, presumably because the additional phosphorothioate linkages interfere with the interaction of the oligonucleotide with the RISC pathway components (e.g., with Ago). In certain embodiments, the oligonucleotides having motifs herein result in single-stranded RNAi compounds having desirable properties. In certain embodiments, such oligonucleotides may be paired with a second strand to form a double-stranded RNAi compound. In such embodiments, the second strand of such double-stranded RNAi compounds may comprise a motif of the present invention, may comprise another motif of modifications or may be unmodified.

It has been shown that in certain circumstances for single-stranded RNA comprising a 5'-phosphate group has RNAi activity if but has much less RNAi activity if it lacks such 5'-phosphate group. The present inventors have recognized that in certain circumstances unmodified 5'-phophate groups may be unstable (either chemically or enzymatically). Accordingly, in certain circumstances, it is desirable to modify the oligonucleotide to stabilize the 5'-phosphate. In certain embodiments, this is achieved by modifying the phosphate group. In certain embodiments, this is achieved by modifying the sugar of the 5'-terminal nucleoside. In certain embodiments, this is achieved by modifying the phosphate group and the sugar. In certain embodiments, the sugar is modified at the 5'-position, the 2'-position, or both the 5'-position and the 2'-position. As with motifs, above, in embodiments in which RNAi activity is desired, a phosphate stabilizing modification must not interfere with the ability of the oligonucleotide to interact with RISC pathway components (e.g., with Ago).

In certain embodiments, the invention provides oligonucleotides comprising a phosphate-stabilizing modification and a motif described herein. In certain embodiments, such oligonucleotides are useful as single-stranded RNAi compounds having desirable properties. In certain embodiments, such oligonucleotides may be paired with a second strand to form a double-stranded RNAi compound. In such embodiments, the second strand may comprise a motif of the present invention, may comprise another motif of modifications or may be unmodified RNA.

The target for such antisense compounds comprising a motif and/or 5'-phosphate stabilizing modification of the present invention can be any naturally occurring nucleic acid. In certain embodiments, the target is selected from: pre-mRNA, mRNA, non-coding RNA, small non-coding RNA, pd-RNA, and microRNA. In embodiments, in which a target nucleic acid is a pre-RNA or a mRNA, the target may be the same as that of a naturally occurring micro-RNA (i.e., the oligonucleotide may be a microRNA mimic). In such embodiments, there may be more than one target mRNA.

In certain embodiments, the invention provides compounds and methods for antisense activity in a cell. In certain embodiments, the cell is in an animal. In certain embodiments, the animal is a human. In certain embodiments, the invention provides methods of administering a compound of the present invention to an animal to modulate the amount or activity or function of one or more target nucleic acid.

In certain embodiments oligonucleotides comprise one or more motifs of the present invention, but do not comprise a phosphate stabilizing modification. In certain embodiments, such oligonucleotides are useful for in vitro applications. In certain embodiments, such oligonucleotides are useful for in vivo applications where RISC activity is not required. For example, in certain embodiments, such oligonucleotides alter splicing of pre-mRNA.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

EXAMPLES

General $^1$H and $^{13}$C NMR spectra were recorded on a 300 MHz and 75 MHz Bruker spectrometer, respectively.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. Nos. 5,610,289 or 5,625,050.

Phosphoramidite internucleoside linkages can be prepared as described in U.S. Pat. No. 5,256,775 or U.S. Pat. No. 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378, 825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Patent 5,223,618.

Example 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M NH$_4$OAc with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

Example 4

Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, NJ). Non-standard nucleosides are synthesized as per standard or patented methods and can be functionalized as base protected beta-cyanoethyldiisopropyl phosphoramidites.

Oligomeric compounds can be cleaved from support and deprotected with concentrated NH$_4$OH at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Analysis of Oligomeric Compounds using Uhe 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 μg/mL per 100 nM oligomeric compound(s). This transfection mixture is incubated at room temperature for approximately 0.5 hours. For cells grown in 96-well plates, wells are washed once with 100 μL OPTI-MEM™-1 and then treated with 130 μL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™.

Other suitable transfection methods known in the art include, but are not limited to, electroporation.

Example 7

Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5× PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8

Analysis of Oligonucleotide Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 9

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the a target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 10

RNA Isolation

Poly(A)+mRNA Isolation

Poly(A)+mRNA is isolated according to Miura et al., (Clin. Chem., 1996, 42, 1758-1764). Other methods for poly (A)+mRNA isolation are routine in the art. Briefly, for cells grown on 96-well plates, growth medium is removed from the cells and each well is washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 μL of lysate is transferred to Oligo d(T) coated 96-well plates (AGCT Inc., Irvine Calif.). Plates are incubated for 60 minutes at room temperature, washed 3 times with 200 μL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 μL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 μL cold PBS. 150 μL Buffer RLT is added to each well and the plate vigorously agitated for 20 seconds. 150 μL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 μL of Buffer RW1 is added to each well of the RNEASY 96™ plate and incubated for 15 minutes and the vacuum is again applied for 1 minute. An additional 500 μL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

Forward primer: AATGGCTAAGTGAAGATGACAAT-CAT (SEQ ID NO: 2)

Reverse primer: TGCACATATCATTACACCAGTTCGT (SEQ ID NO: 3) And the PCR probe:

FAM-TTGCAGCAATTCACTGTAAAGCTG-GAAAGG-TAMRA (SEQ ID NO: 4), where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

Preparation of Compound 5

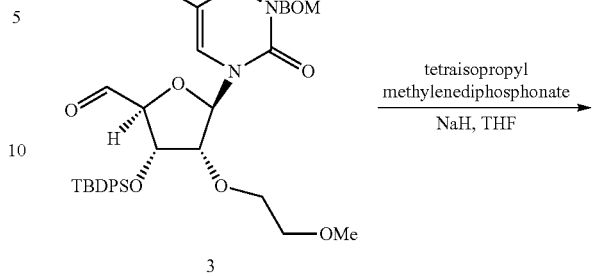

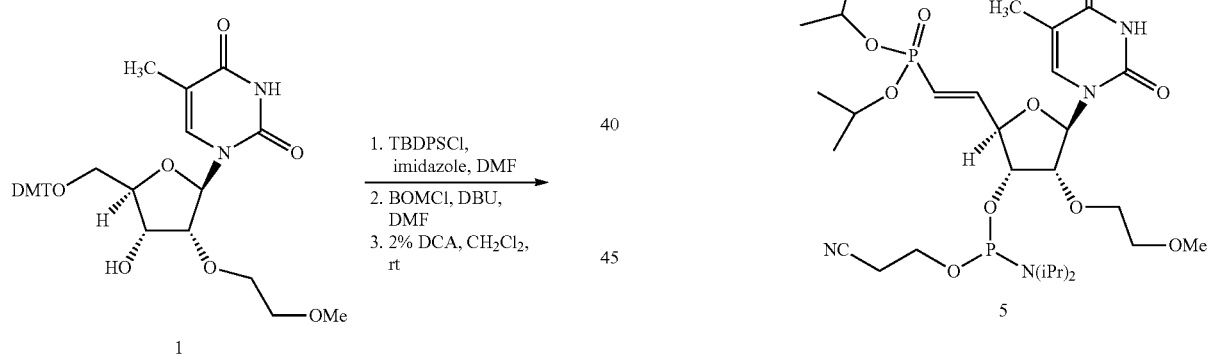

Compound 1 is prepared according to the procedures published in U.S. Pat. No. 5,969,116.

Example 14

Preparation of Compound 9

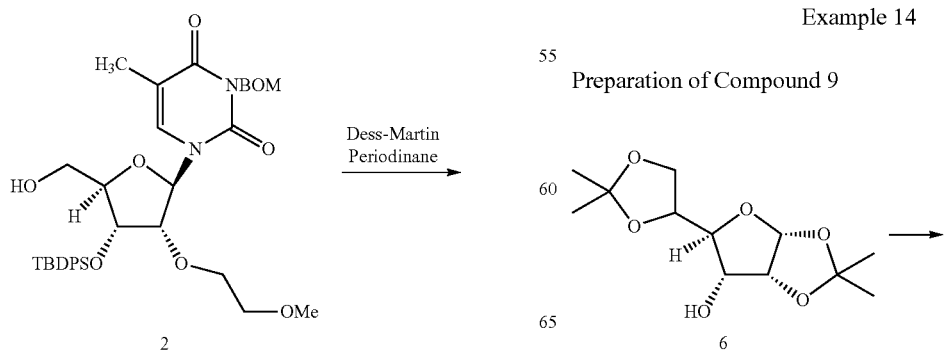

97 -continued

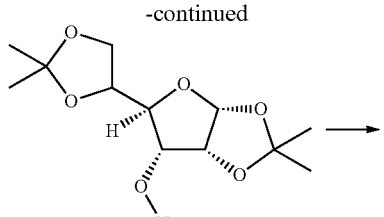

7

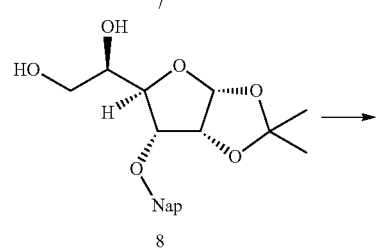

8

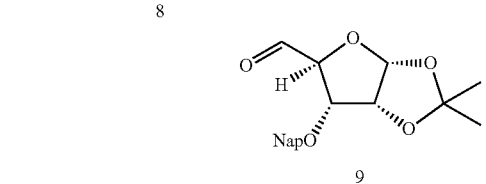

9 a) Preparation of Compound 7

Commercially available 1,2;5,6-di-O-isopropylidene-a-D-allofuranose, Compound 6, (135 g, 519.0 mmol) and 2-(bromomethyl)-naphthalene (126 g, 570.0 mmol) were dissolved in DMF (500 mL) in a three-necked flask (500 mL) and the reaction was cooled in an ice bath. Sodium hydride (60% w/w, 29 g, 727.0 mmol) was carefully added (6 g portions every 10 minutes) to the reaction and the stirring was continued for another 60 minutes after the addition was complete. At this time TLC analysis showed no more sugar (Compound 6). The reaction was carefully poured onto crushed ice (ca. 500 g) and the resulting slurry was stirred vigorously until all the ice melted. The resulting off-white solid was collected by filtration and suspended in water. The suspension was stirred vigorously using a mechanical stirrer for 30 minutes after which the solid was collected by filtration and suspended in hexanes. The suspension was stirred vigorously for 30 minutes after which the solid was collected by filtration and air dried for 4-6 hours and then dried under high vacuum over $P_2O_5$ for 16 hours to provide Compound 7 (206.0 g, 99%) as an off-white solid. $^1$H NMR (300 MHz, CDCl$_3$) δ: 7.85 (m, 4H), 7.48 (m, 3H), 5.74 (s, 1H), 4.92 (d, 1H, J=11.7), 4.75 (d, 1H, J=11.6), 4.58 (m, 1H), 4.36 (m, 1H), 4.15 (m, 1H), 4.03-3.86 (m, 3H), 1.61 (s, 3H), 1.36 (s, 9H).

b) Preparation of Compound 8

Compound 7 (200.0 g, 0.5 moles) was added in small portions to a solution of acetic acid (2.2 L) and water (740 mL). The reaction was stirred at room temperature for 16 h after which, TLC analysis (30% EtOAc/hexanes) indicated complete consumption of Compound 7. The reaction was then concentrated under reduced pressure until most of the acetic acid was removed. The remaining solution was poured into a stirred mixture of EtOAc (1 L) and water (1 L). Solid KOH was then added to the above mixture until the aqueous layer was strongly basic (pH>12). The organic layer was then separated, washed with saturated sodium bicarbonate solution and brine then dried (Na$_2$SO$_4$), filtered and concentrated under reduced pressure to provide Compound 8 as a yellow foam, which was used without any further purification.

c) Preparation of Compound 9

A solution of NaIO$_4$ (107.0 g) in water (3 L) was added over 40 minutes to a stirred (mechanical stirrer) solution of Compound 8 in dioxane (1.5 L). After 60 minutes the reaction mixture was poured into EtOAc (1.5 L) and the organic layer was separated, washed with water (1 L) and brine (1 L) then dried (Na$_2$SO$_4$) and concentrated to provide Compound 9 as a yellow oil, which was used without any further purification.

Example 15

Preparation of Compound 14

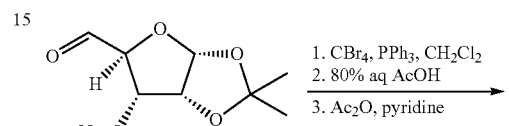

9

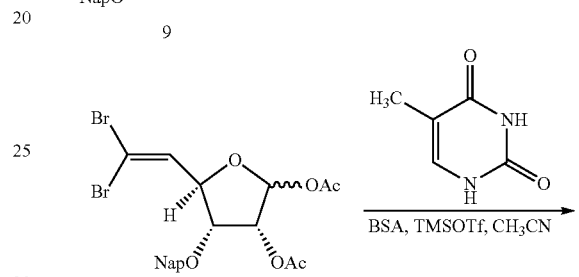

10

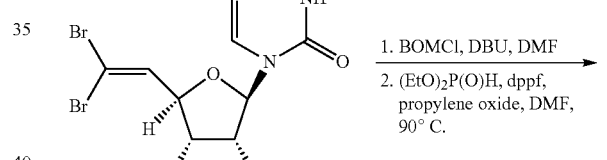

11

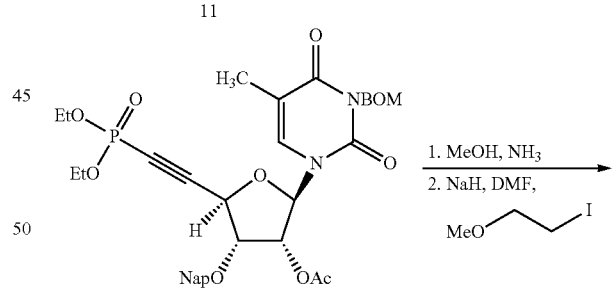

12

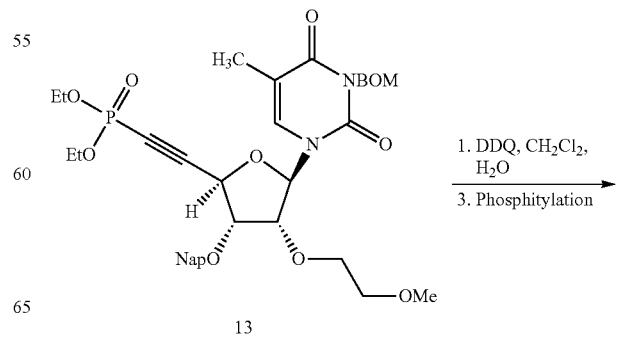

13

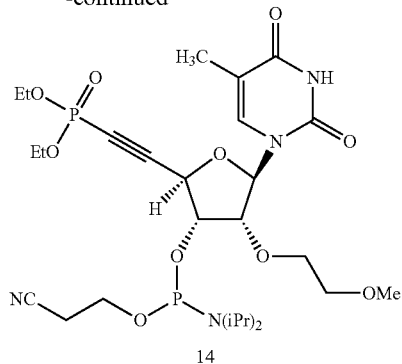

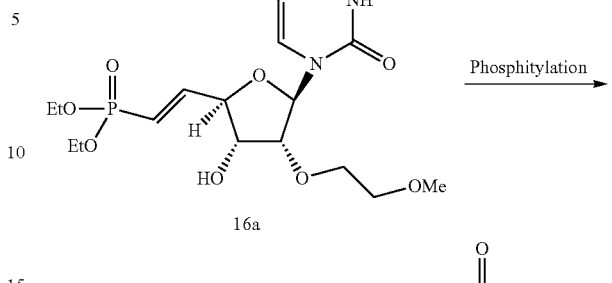

Compound 9 is prepared as per the procedures illustrated in Example 14.

Example 16

Preparation of Compound 17

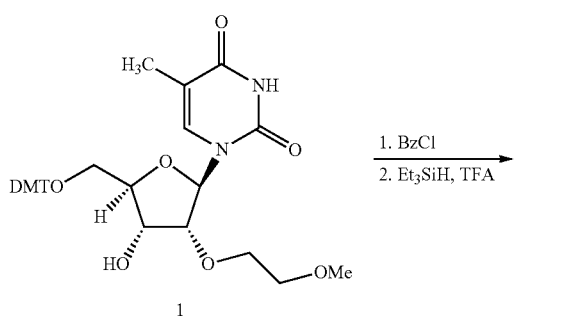

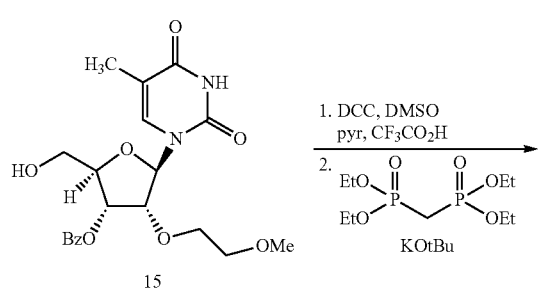

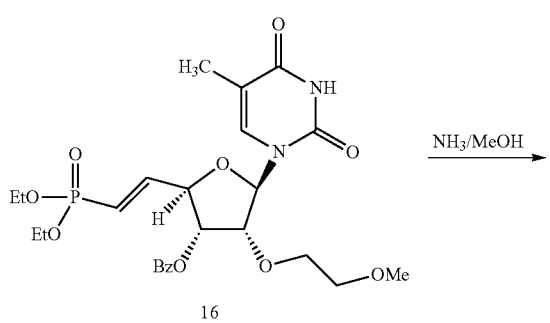

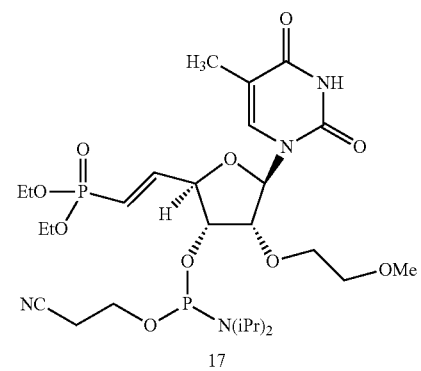

a) Preparation of Compound 15

Compound 1 was prepared according to the procedures published in U.S. Pat. No. 5,969,116. Benzoyl chloride (5.6 mL, 48.5 mmol) was added to solution of nucleoside Compound 1 (25 g, 40.5 mmol) in pyridine (100 mL). After stirring at room temperature for 3 hours, additional benzoyl chloride (2.5 mL) was added to the reaction. After an additional 60 minutes, the reaction was quenched with water and then partitioned between ethyl acetate and water. The organic layer was further washed with water, brine, dried (sodium sulfate) and concentrated to provide the crude benzoyl protected nucleoside which was used without any further protection.

Trifluoroacetic acid (5 mL) was added to a solution of the crude nucleoside from above and triethylsilane (12 mL) in dichloromethane. After 2 hours, additional trifluoroacetic acid (5 mL) and triethylsilane (5 mL) were added to the reaction and the stirring was continued for an additional 4 hours during which time the reaction turned light yellow from an initial bright orange. The solvent was removed on a rotary evaporator and the residue was dissolved in ethyl acetate and the organic layer was carefully washed with water, sodium bicarbonate, brine, dried (sodium sulfate) and concentrated. The resulting white solid was suspended in hexanes and collected by filtration and further washed with additional hexanes to provide nucleoside Compound 15 (14.9 g, 87% over 2 steps).

b) Preparation of Compound 16

Dicyclohexylcarbodimide (1.5 g, 7.2 mmol) was added to a solution of Compound 15 (2.0 g, 4.8 mmol) and pyridinium trifluoroacetate (0.92 g, 4.8 mmol) in dimethylsulfoxide (48 mL) and the reaction mixture was allowed to stir at room temperature for 6 hours. In a separate flask, a solution of potassium tert-butoxide (10 mL of a 1M solution in THF) was added to a solution of tetraethylmethylenediphosphonate (2.4 mL, 9.6 mmol) in THF (20 mL). After stirring for 10 minutes at room temperature, this flask was cooled in an ice bath and the DMSO solution was added via a cannula. After stirring at room temperature for 2 hours, the reaction was diluted with ethyl acetate and the organic layer was washed with water, brine, dried (sodium sulfate) and concentrated. Purification by column chromatography (silica gel, eluting with 20 to 40% acetone in dichloromethane) provided the vinyl nucleoside Compound 16 (1.25 g, 47%).

c) Preparation of Compound 16a

A solution of vinyl nucleoside Compound 16 (110 mg, 0.2 mmol) and 7N ammonia in methanol (2 mL) were aged at room temperature for 6 hours and the solvent was removed on a rotary evaporator. Purification of the residue by chromatography (silica gel, eluting with 70 to 90% acetone in dichloromethane) provided Compound 16a (84 mg, 95%).

d) Preparation of Compound 17

(2-Cyanoethoxy)-tetraisopropylphosphordiamidite (0.084 mL, 0.28 mmol) was added to a solution of Compound 16a (84 mg, 0.19 mmol), tetrazole (12 mg, 0.15 mmol) and N-methylimidazole (1 drop) in dimethylformamide (1 mL). After stirring at room temperature for 3 hours, the reaction was diluted with ethyl acetate and the organic layer was washed with brine (2×), dried (sodium sulfate) and concentrated. Purification by column chromatography (silica gel, eluting with 2 to 4% methanol in dichloromethane) provided amidite Compound 17 (113 mg, 90%).

Example 17

Preparation of Compounds 19 and 19a

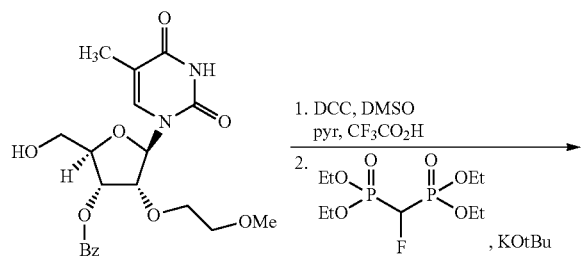

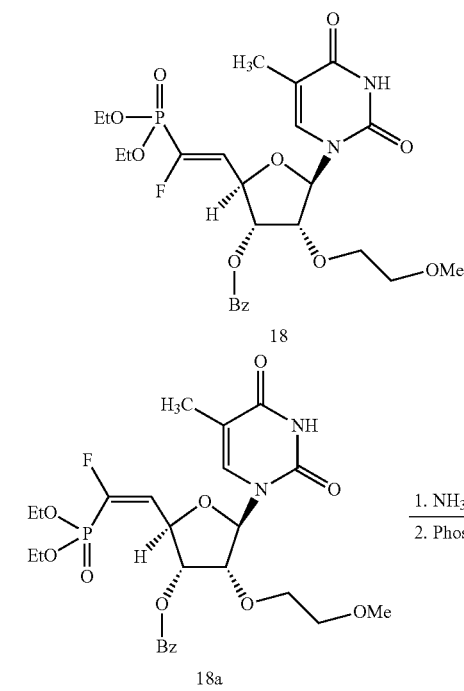

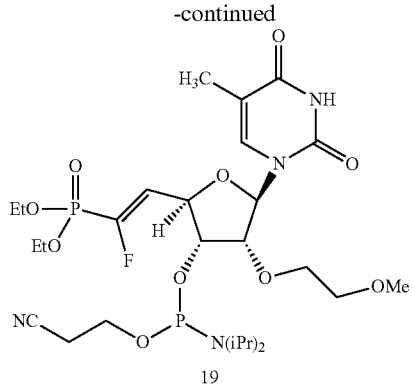

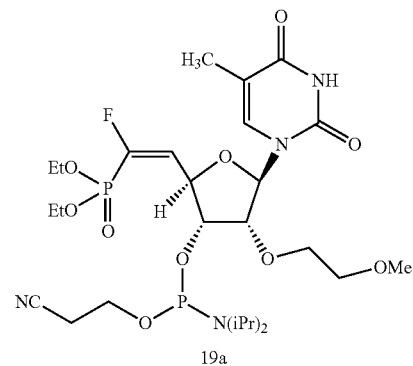

Compound 15 was prepared as per the procedures illustrated in Example 16. Compounds 18 and 18a were separated by chromatography. The structures of Compounds 19 and 19a were confirmed by spectral analysis.

Example 18

Preparation of Compound 20

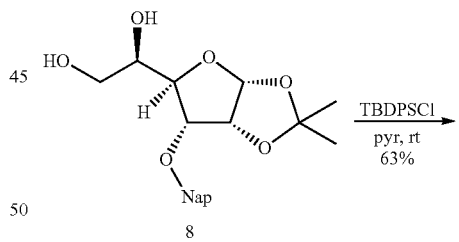

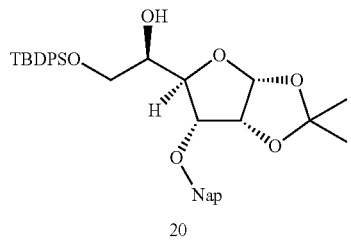

Compound 8 was prepared as per the procedures illustrated in Example 14.

Example 19
Preparation of Compound 24
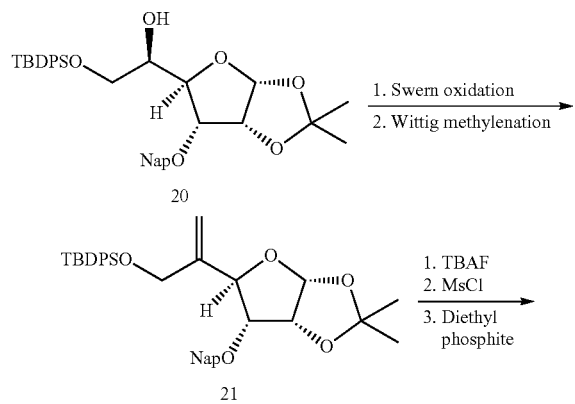
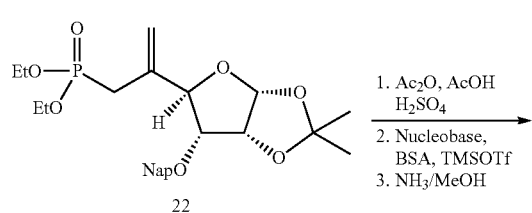
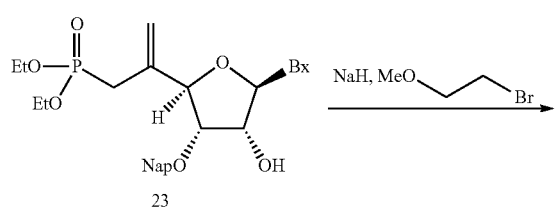
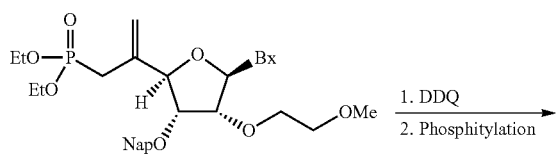
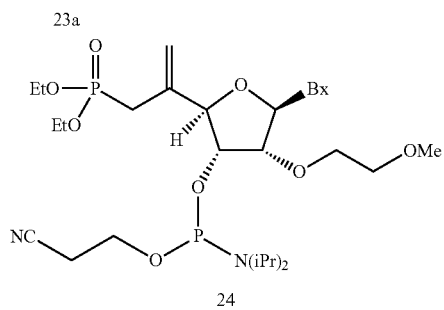
Compound 20 is prepared as per the procedures illustrated in Example 18.
Example 20
Preparation of Compound 27
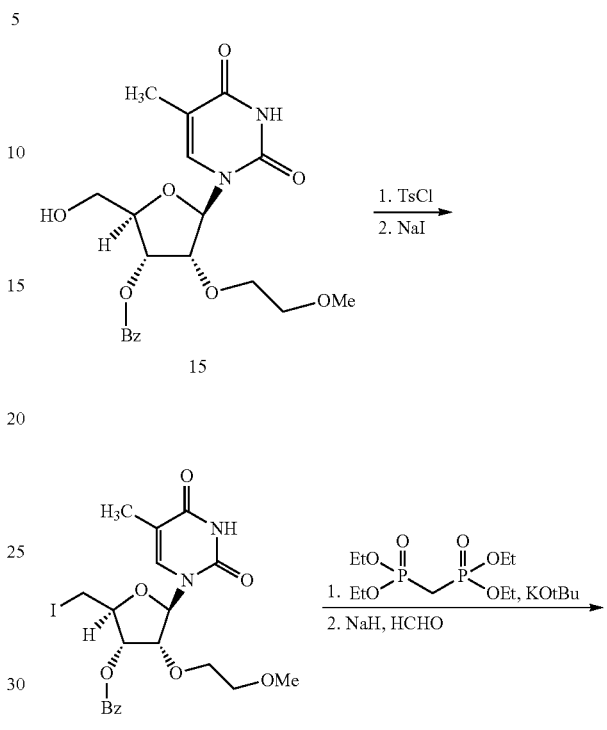
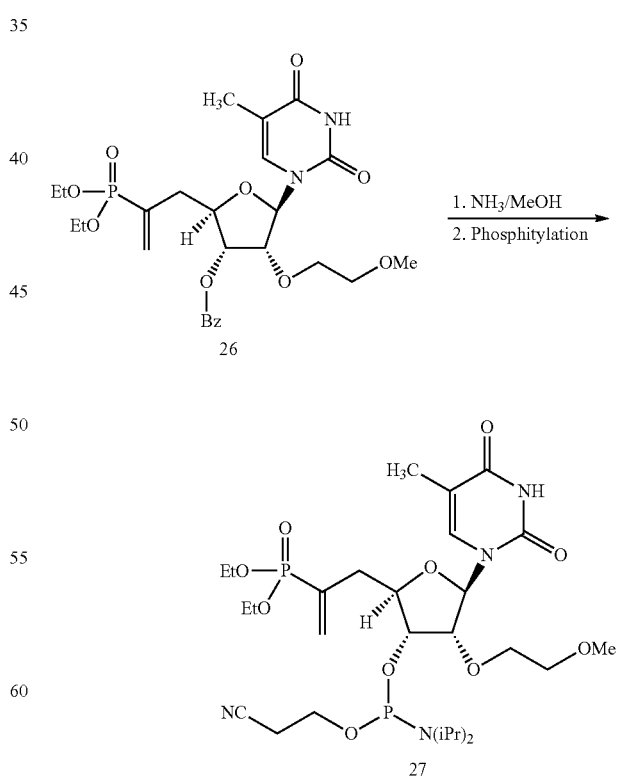
Compound 15 is prepared as per the procedures illustrated in Example 16.

Example 21
Preparation of Compound 30
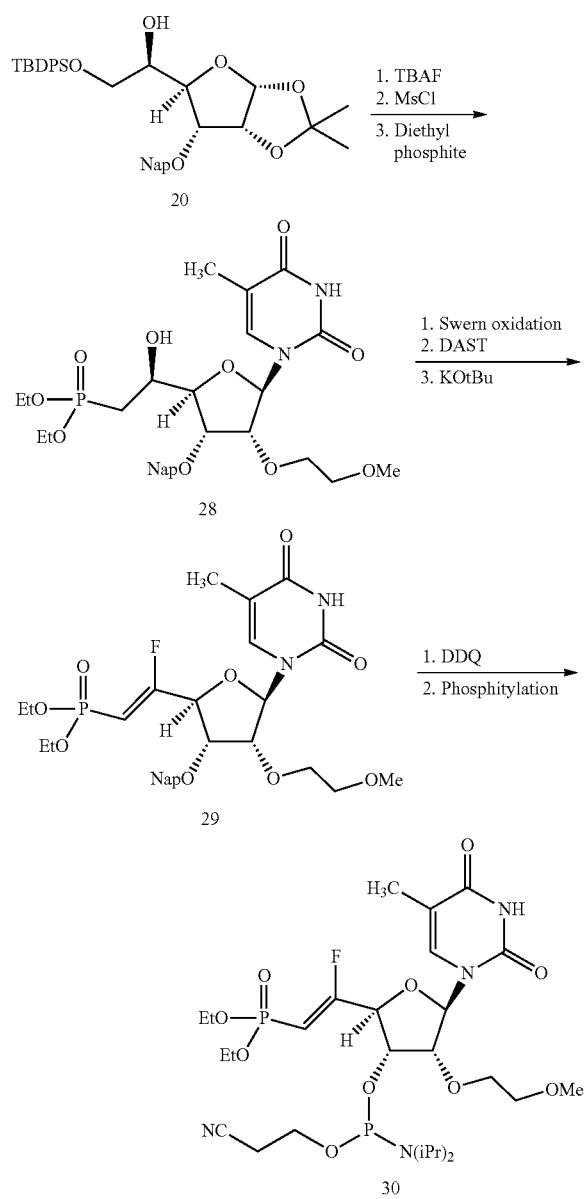
Example 22
Preparation of Compound 32
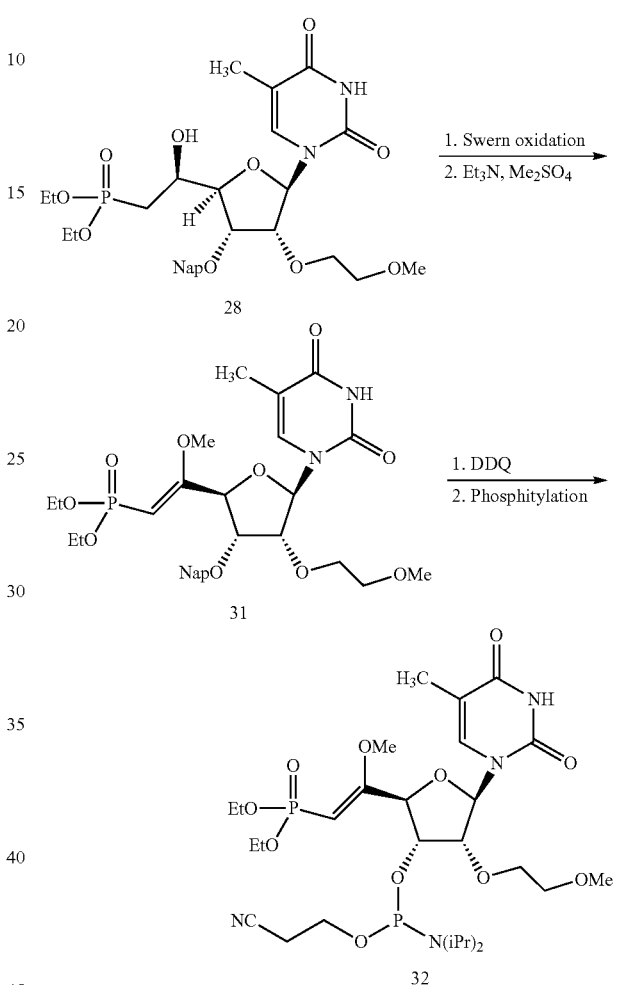
Compound 20 is prepared as per the procedures illustrated in Example 18.
Compound 28 is prepared as per the procedures illustrated in Example 21.
Example 23
Preparation of Compounds 36, 37 and 38
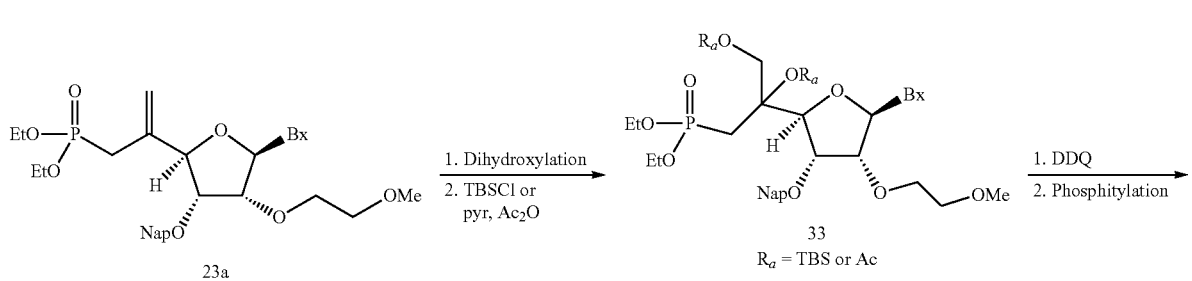

-continued
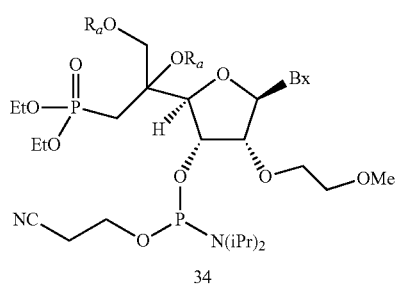
34
1. Oligo synthesis and incorporate at 5' end
2. TMSBr, pyridine
3. aq. NH₃
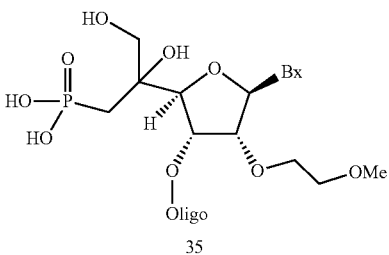
35
NaIO₄ →
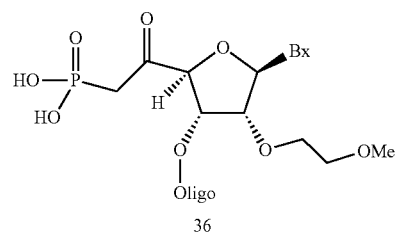
36
Lawesson's reagent ↙   ↘ R_bNH₂, acid
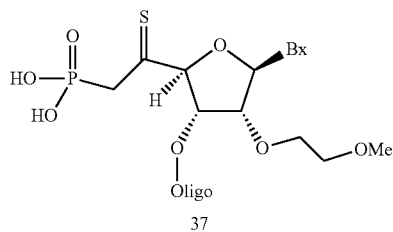
37
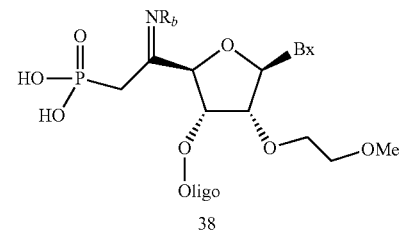
38
R_b = H, alkyl, sub-alkyl or hydroxyl
Compound 23a is prepared as per the procedures illustrated in Example 19.
Example 24
Preparation of Compounds 42, 43 and 44
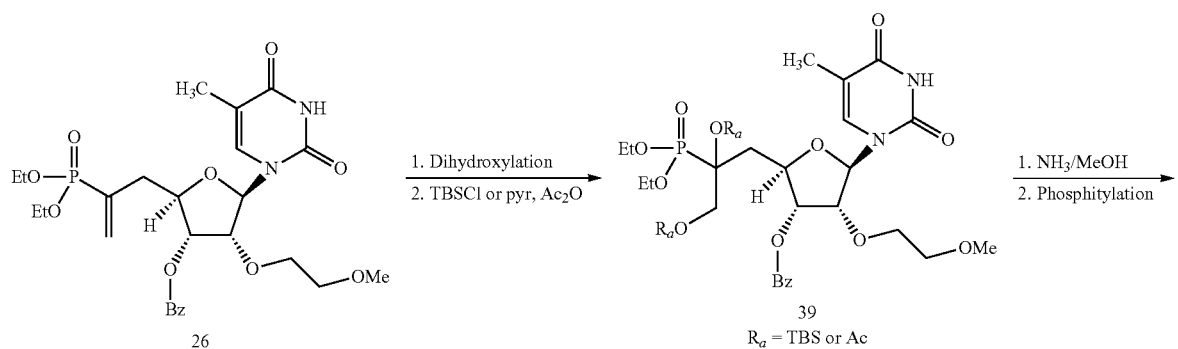

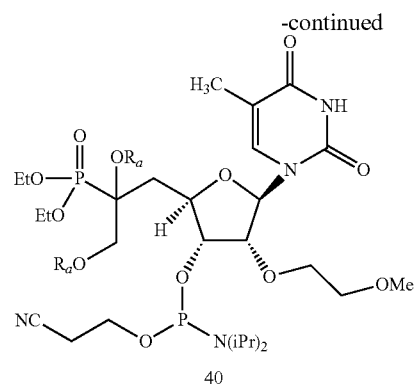
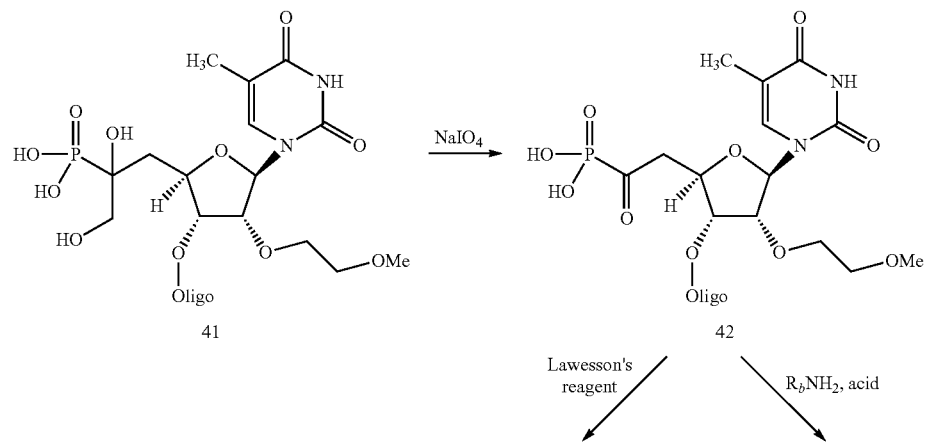
Compound 26 is prepared as per the procedures illustrated in Example 20.
Example 25
Alternative methods for the preparation of Compounds 14 and 47

111
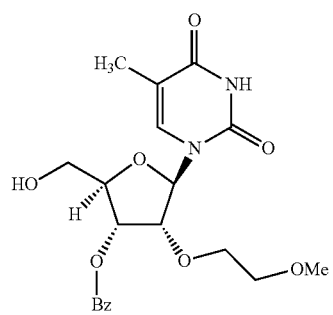
15
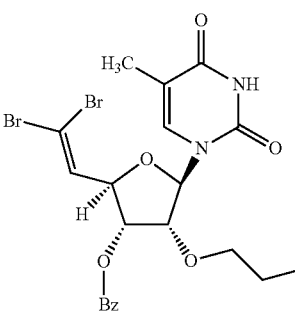
45
1. Swern oxidation
2. CBr₄, PPh₃
1. NH₃, MeOH
2. Pd(OAc)₂, dppf propylene oxide, Diethylphosphite
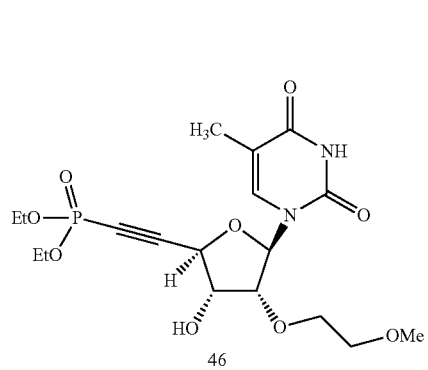
46
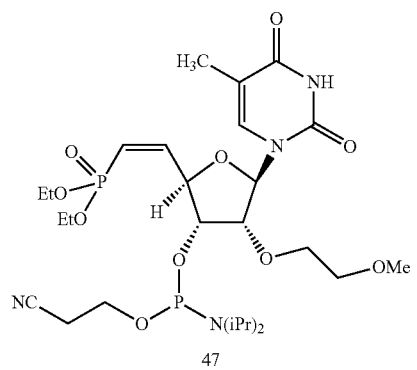
47
1. Lindlar cat, H₂
2. Phosphitylation
Phosphitylation
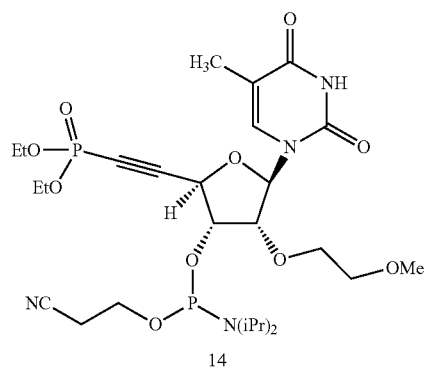
14
Compound 15 was prepared as per the procedures illustrated in Example 16.

Example 26
Preparation of Compound 50
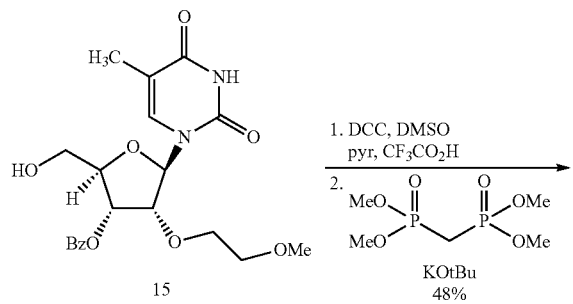
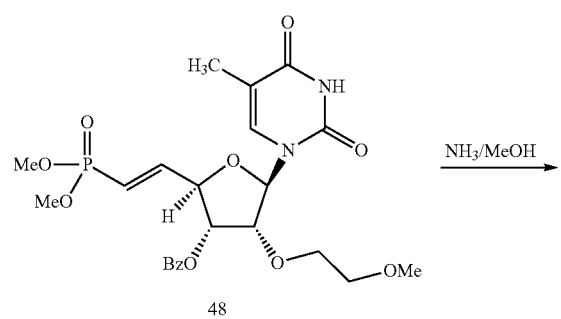
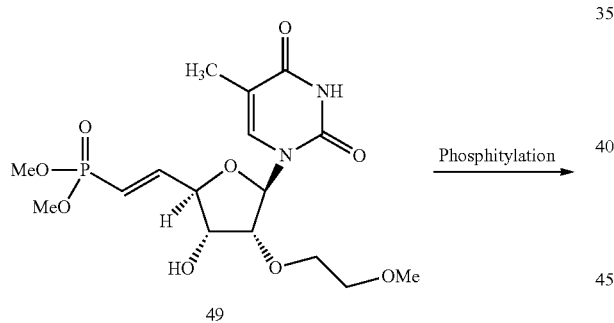
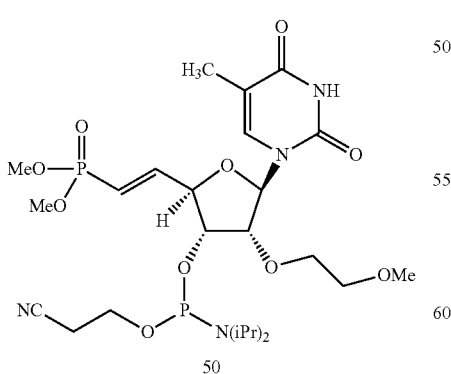
Compound 15 was prepared as per the procedures illustrated in Example 16. The spectral analysis of Compound 50 was consistent with the structure.
Example 27
Preparation of Compound 62
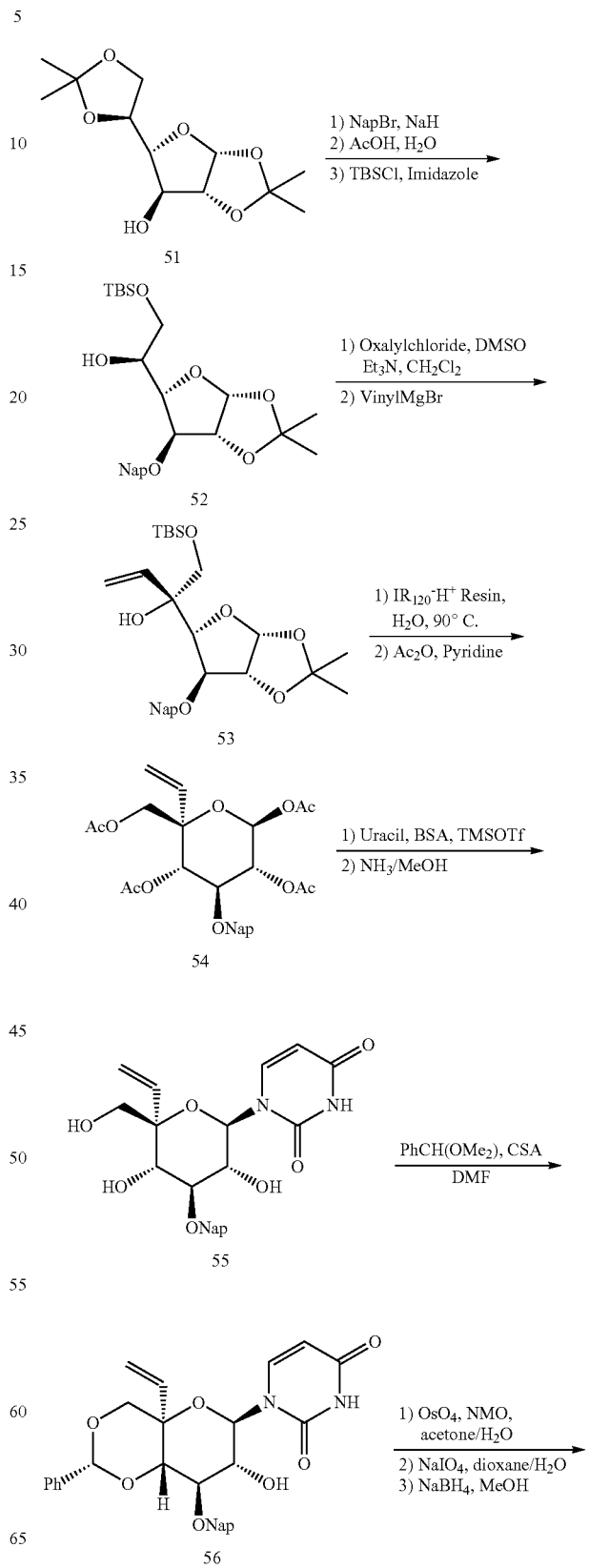

-continued

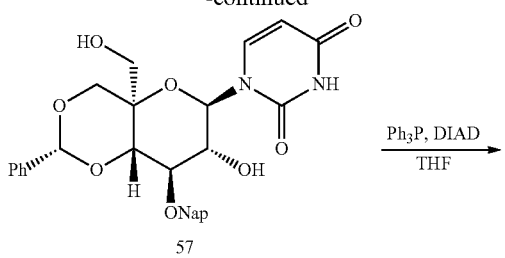
57

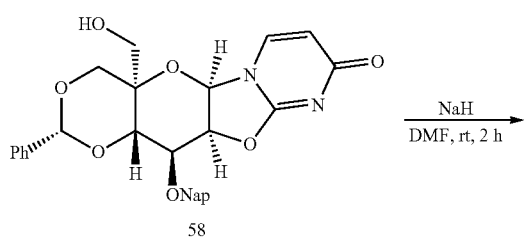
58

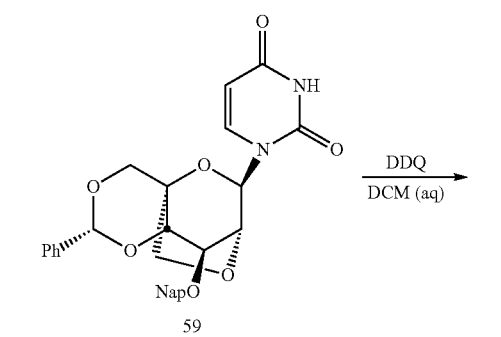
59

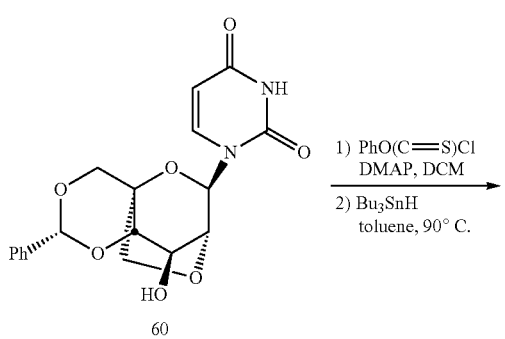
60

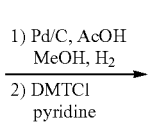
61

-continued

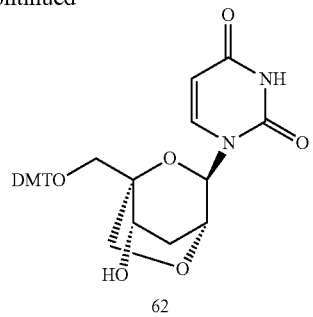
62 a) Preparation of Compound 52 (Alkylation of Diacetone Glucose)

The starting material, Compound 51 is commercially available and can also be prepared according to the procedure of Moffatt et al, *J. Org. Chem.,* 1979, 44, 1301.

NaH (60% in mineral oil, 49.2 g, 1.6 equivalents) was added to a 2 L round bottom flask flushed with nitrogen, and the NaH was washed with hexanes (2×1.0 L) to remove the mineral oil. After decanting the hexanes, DMF (700 mL) was added and the mixture was cooled in an ice bath. Diacetone glucose, Compound 51 (200 g, 0.77 moles) was then added over a period of 30 minutes. The ice-bath was removed and the mixture was stirred for 1 hour at room temperature. The reaction was then cooled in an ice-bath for second time, and 1-bromomethylnapthylene (187 g, 1.1 equiv) in DMF (100 mL) was added drop-wise over a 30-minute period. Upon complete addition, the ice-bath was stirred over night while the ice was allowed to melt, thereby allowing the reaction to proceed to room temperature. After 16 h, the reaction was complete, as determined by TLC ($R_f$=0.45, 20% EtOAc/hexanes and visualized by charring after treatment with anisaldehyde spray reagent). The mixture was then poured onto cold water (1.5 L) that was placed in an ice bath. The aqueous layer was extracted with EtOAc (250 mL×2) and then washed successively with saturated NaHCO$_3$ (1 L), brine (1 L) and the organic layer was evaporated under reduced pressure to give a dark brown oil. This oil was dissolved in minimal DCM and passed through a plug of silica gel eluting with 100% Hexanes (3.0 L) to remove minor upper impurities, then 20% EtOAc/Hexanes to collect the major spot. Concentration of the solvent provided the alkylated product (269 g, 87%) as a brown oil which was used without further purification.

Selective Cleavage of the Isopropylidine

The crude oil from above (69 g, 0.67 moles), was dissolved in acetic acid (2.2 L) and water (900 mL). The reaction was allowed to proceed for 16 h at room temperature. The reaction was follow by TLC (20% EtOAc/Hexanes). After completion of the reaction, most of the acetic acid was evaporated under reduced pressure and then the remaining solution was poured into a stirred mixture of EtOAc (1 L)/NaHCO$_3$ (1 L, aq. sat.) in small portions followed by NaHCO$_3$ (s) until gas evolution ceased. The organic layer was washed with water (1 L×2), brine (1 L), dried Na$_2$SO$_4$, filtered and removed under reduced pressure to give a crude yellow oil. The oil was then dissolved in minimal DCM and passed through a plug of silica gel eluting with 20% EtOAc/ Hexanes (3.0 L) to remove the upper spot impurities, and then eluted with 80% EtOAc/Hexanes to give the major compound. Evaporation of the solvent gave the crude product (201 g, 82%) as a light yellow oil. TLC ($R_f$=0.22, 20% EtOAc/hexanes).

Selective Silylation of the Primary Hydroxy Group

The crude compound (105 g, 0.293 moles) was dissolved in anhydrous DMF (1 L) followed by the addition of imidazole (39.9 g, 0.58 moles). The resulting yellow solution was cooled to 0° C. in ice-bath while stirring under nitrogen. tert-Butyldimethylsilyl chloride (TBDMSCl, 48.5 ml, 0.322 moles) dissolved in a minimal amount of DMF was added drop-wise over a 40-minute period. The ice-bath, initially at 0° C. upon complete addition, was allowed to come to room temperature and stirring continued for an additional 16 h. The reaction was complete at this time, as determined by TLC ($R_f$=0.56, 20% EtOAc/hexanes). The reaction was then quenched by addition of MeOH (50 mL). Water (1 L) and EtOAc (500 mL) were then added and the organic was washed with, saturated $NaHCO_3$ (1 L) and brine (1 L) and then dried ($Na_2SO_4$), filtered and the solvent removed under reduced pressure to give Compound 52 (139.0 g) as a yellow oil.

$^1$H NMR (300 MHz, $CDCl_3$+2% $D_2O$): δ 7.7 and 7.4 (m, 7H, Nap), 5.86 (d, 1H, J=3.6 Hz), 4.7 (m, 2H), 4.54 (d, 1H, J=5.7 Hz), 4.08 (s, 2H), 3.9-4.0 (m, 1H), 3.7-3.8 (m, 2H), 1.39 (s, 1H, $CH_3$), 1.24 (s, 1H, $CH_3$), 0.82 (s, 9H, tBu), 0.02 (s, 6H, $SiMe_2$).

$^{13}$C NMR (75 MHz, $CDCl_3$+2% $D_2O$): δ 135.1, 133.3, 133.1, 128.3, 128.0, 127.7, 126.6, 126.2, 126.0, 125.7, 111.7, 105.2, 82.6, 81.9, 79.6, 72.6, 68.6, 64.5, 26.7, 26.3, 25.9, 18.3, -5.4. LCMS (Method $CN_1$), retention time=1.8 min, m/z=497.1 (M+Na), >98% purity.

b) Preparation of Compound 53

Oxalyl chloride (12.2 mL, 145 mmoles) and $CH_2Cl_2$ (280 mL) were added to a 2 L round bottom flask fitted with two addition funnels. One addition funnel contained DMSO (20.5 mL, 289 mmoles) in $CH_2Cl_2$ (30 mL), while the other funnel contained Compound 52 (45.75 g, 96.4 mmoles) dissolved in $CH_2Cl_2$ (380 mL). The round bottom was then cooled to −78° C. under nitrogen, and the DMSO solution was added dropwise over 15 minutes. After stirring an additional 50 minutes, the solution of Compound 52 was added dropwise over 15 min. After stirring an additional 30 minutes, $Et_3N$ (60 mL, 434 mmoles) was added over 10 minutes and the reaction was allowed to proceed at room temperature for 30 minutes. The reaction was then quenched with $NH_4Cl$ (sat, 150 mL), and the organic layer was washed successively with 10% citric acid (1 L), sodium bicarbonate (sat, 1 L), and brine (1 L). The organic layer was then dried over $Na_2SO_4$, concentrated and filtered thru silica gel (20% EtOAc/hexanes) to give the crude ketone (42.4 g, 93%) which was used directly in the next step without further purification. TLC, ($R_f$=0.55, 20% EtOAc/hexanes). LCMS (Method CNA retention time=2.1 min, m/z=473.1 (M+H), 495.1 (M+Na), 967.3 (2M+Na).

The crude ketone (39 g, 82.5mmoles) in THF (240 mL) was added to a 1 L round bottom flask equipped with an addition funnel containing 1.0 M vinyl magnesium bromide in THF (125 mL). The flask was cooled in an ice bath and the Grignard reagent was then added dropwise over 10 minutes. The reaction was then allowed to proceed at room temperature for 1.5 h, and quenched with $NH_4Cl$ (sat, 150 mL). $Et_2O$ (400 mL) was added and the organic layer was washed with brine (1 L). The organic layer was then passed through a plug of silica gel (eluting with $Et_2O$ as necessary) and then concentrated to give a quantitative yield of Compound 53, which was about 90% pure, and used directly in the next step. TLC, ($R_f$=0.55, 20% EtOAc/hexanes).

$^1$H NMR (300 MHz, $CDCl_3$): δ 7.79-7.90 and 7.47-7.56 (m, 7H, Nap), 6.11 (dd, 1H, J=16.2, 9.6 Hz, =CH—), 6.08 (d, 1H, J=3.9 Hz, H-1), 5.49 (dd, 1H, J=17.4, 1.5 Hz, =$CH_2$); 5.22 (dd, 1H, J=12.3, 1.5 Hz, =$CH_2$), 4.91 and 4.72 (ABq, 2H, $CH_2$), 4.71 (d, 1H, J=4.2 Hz, H-2), 4.38 (d, 1H, J=3.0 Hz, H-4), 4.24 (d, 1H, J=2.7 Hz, H-3), 3.92 (s, 1H, OH), 3.63 (d, 1H, J=9.6 Hz, 6a), 3.47 (d, 1H, J=9.6 Hz, 6b), 1.53 (s, 3H, $CH_3$), 1.38 (s, 3H, $CH_3$), 0.86 (s, 9H, C($CH_3$)$_3$), −0.0 (s, 3H, SiMe), −0.08 (s, 3H, SiMe). $^1$H NMR matched closely with the OBn derivative reported in *Tetrahedron Lett.*, 1993, 1653.

LCMS (Method DR1), m/z=501.1 (M+H), 523.2 (M+Na).

c) Preparation of Compound 54 (Hydrolysis of TBS and Isopropylidine)

To the mostly pure Compound 53 (41.3 g, 82.5 mmoles) and Amberlite (IR-120 H$^+$ Strongly Acidic ion-exchange resin, 80 g), was added 1,4-dioxane (275 mL) and $H_2O$ (230 mL). This was heated at 90° C. for 36 h, and then filtered hot through celite and evaporated to dryness. The resultant crude solid was then dried for 12 h at 50° C. over $P_2O_5$.

Acetylation of the Hydrolyzed Material

The crude white solid from above was treated with pyridine (290 mL) and $Ac_2O$ (78 mL, 10 equiv) was then added dropwise followed by DMAP (120 mg). The reaction proceeded at room temperature for 16 h and then the solvent was evaporated and co-evaporated with toluene (3x100mL). The major product was purified by silica gel chromatography (25% EtOAc/hexanes to 35%EtOAc/hexanes) to give the crude tetraacetate, Compound 54 (31.4g , 74%) as a clear white foam. TLC ($R_f$=0.27, 40% EtOAc/hexanes).

$^1$H-NMR (300 MHz, $CDCl_3$): δ 7.83-7.79, 7.68, 7.5-7.4, 7.35 and 7.32 (m, 7H, Nap), 5.95-5.87 (m, 3H, CH=CH and H1), 5.63 (dd, 1H, J=8.7, 3.3 Hz, =CH), 5.46 (d, 1H, J=9.9 Hz, H4), 5.25 (dd, 1H, J=9.3, 8.4 Hz, H2), 4.76 (s, 2H, $CH_2$Nap), 4.14 and 3.71 (d, J=12.4 Hz, H6), 3.79 (dd, 1H, J=9.8, 9.8 Hz, H3), 2.10 (s, 6H, Ac×2), 1.95 (s, 3H, Ac), 1.90 (s, 3H, Ac). $^{13}$C NMR (75 MHz, $CDCl_3$+2% $D_2O$): δ 170.7, 169.5, 169.1, 169.0, 135.2, 133.2, 133.0, 129.8, 128.3, 127.9, 127.7, 126.3 (2C), 126.1, 125.5, 122.03, 88.9, 78.5, 78.1, 74.6, 72.6, 69.5, 65.2, 20.9 (3C), 20.8.

LCMS (Method CN1), retention time=1.47 min, m/z=537.1 (M+Na), purity=99%.

Note: Compound 54 was prepared from Compound 51 by a slightly modified version of the procedures reported in *Tetrahedron Lett.*, 1993, 1653 and *Tetrahedron*, 2004, 6813.

d) Preparation of Compound 55 (Vorbrüggen Coupling and Deacetylation)

N,O-Bis(trimethylsilyl)acetamide (BSA, 54.7 mL, 224 mmol) was added to a stirred suspension of uracil (10.2 g, 90.7 mmol) and Compound 54 (31.1 g, 60.4 mmoles) in dry acetonitrile (300 mL). After stirring at rt for 30 min a clear solution was observed, and the reaction was cooled to 0° C. under nitrogen. Trimethylsilyfluoromethanesulfonate (TMSOTf, 21.9 mL, 121 mmol) was added and after the reaction was stirred at rt for 15 min, it was transferred to a preheated oil bath at 80° C. After stirring for 4 h at 80° C., the reaction was cooled to rt and MeOH (20 mL), EtOAc (250 mL) and $H_2O$ (400 mL) were added. The organic phase was then sequentially washed with sat. $NaHCO_3$, brine, dried ($Na_2SO_4$) and concentrated to provide the crude triacetate. TLC ($R_f$=0.60, 80% EtOAc/hexanes). LCMS (Method m/z=567.1 (M+H).

The crude nucleoside was treated with 7N MeOH/$NH_3$ (300 mL) at 50° C. overnight and then evaporated to dryness. The major product was purified by silica gel chromatography (2% MeOH/$CH_2Cl_2$ to 6% MeOH/$CH_2Cl_2$) to give the triol Compound 55 (17.75 g, 67%) as a white solid. TLC ($R_f$=0.25, 8% MeOH/$CH_2Cl_2$).

$^1$H NMR (300 MHz, DMSO-$d_6$/2% $D_2O$): δ 7.9-7.8 (m, 5H, Nap and H6), 7.62, 7.59, and 7.53-7.46 (m, 3H, Nap), 6.07 (dd, 1H, J=11.9, 17.3 Hz, C=CH), 5.68 (d, 1H, J=3.0 Hz, H5), 5.66 (s, 1H, H1'), 5.45-5.39 (m, 2H, C=CH$_2$), 4.99 (s, 2H, CH$_2$ONap), 3.93 (d, 1H, J=9.6 Hz, H4'), 3.67 (dd, 1H, J=8.9, 8.9 Hz, H2'), 3.43 (dd, 1H, J=9.6, 12.0 Hz, H3'), 3.16 and 3.42 (d, 2H, J=8.9 Hz, 6'-CH$_2$).

$^{13}$C NMR (75 MHz, DMSO-d$_6$/2% D$_2$O): δ 162.8 (C4), 150.6 (C2), 141.4 (C6), 136.8 (quat), 132.6 (quat), 132.5 (=CH—), 132.0 (quat), 127.3, 127.2, 127.1, 125.8, 125.7, 125.3,* 117.9 (=CH$_2$), 101.6 (C5), 82.3 (C3'), 81.3 (C5'), 77.8 (C1'), 73.5 (CH$_2$ONap), 71.1 (C2'), 68.4 (C4'), 64.8 (6'-CH$_2$). Note: *Between 127.3 and 125.3 lies one additional carbon that overlaps one of the others.

LCMS (Method G1), retention time=2.09 min, m/z=463.1 (M+Na), purity >99%.

e) Preparation of Compound 56 (Benzylidine Formation)

To a stirred mixture of triol Compound 55 (16.1 g, 36.5 mmoles) in dry DMF (180 mL) was added camphorsulphonic acid (CSA, 850 mg) followed by benzaldehyde dimethylacetal (BDMA, 22 mL, 146 mmoles). This was stirred at 50° C., and after two hours additional CSA (600 mg) and BDMA (6 mL) were added. After an additional 2 h, the reaction mixture was cooled to it and partitioned between EtOAc (300 mL) and a NaHCO$_3$ (sat)/H$_2$O (500 mL, 3:2). The organic layer was then washed with brine twice, and the aqueous layers were back-extracted with additional portions of EtOAc. The combined organic layers were dried over Na$_2$SO$_4$, and evaporated to give the crude benzylidine. The crude product was purified by silica gel chromatography (2% MeOH/CH$_2$Cl$_2$ to 5% MeOH/CH$_2$Cl$_2$) to give the benzylidine Compound 56 (18.6 g, 96%) as a white solid. The final compound contained some DMF as determined by $^1$H NMR and did not interfere the subsequent step. TLC (R$_f$=0.45, 8% MeOH/CH$_2$Cl$_2$).

$^1$H NMR (300 MHz, DMSO-d$_6$/2% D$_2$O): δ 7.9-7.8 (m, 5H, Nap and H6), 7.71-7.78 and 7.51-7.41 (m, 8H, Nap, Ph), 6.32 (dd, 3H, J=11.1, 18.2 Hz, C=CH), 5.84 (d, 1H, J=9.3 Hz, H1'), 5.77 (s, 1H, benzylidine CH), 5.72 (d, 1H, J=7.8 Hz, H5), 5.61-5.56 (m, 2H, C=CH$_2$), 4.96 (s, 2H, CH$_2$ONap), 4.06 (d, 1H, J=10.5 Hz, H4'), 4.0-3.7 (m, 4H, H2', H3', and 6'-CH$_2$). $^{13}$C NMR (75 MHz, DMSO-d$_6$/2% D$_2$O): δ 162.8 (C4), 150.4 (C2), 140.8 (C6), 136.9 (quat), 136.0 (quat), 134.5 (=CH—), 132.2 (quat), 131.9 (quat), 128.5, 127.7, 127.1, 127.0, 125.7, 125.5, 125.3, 125.2, 125.1*, 118.0 (=CH$_2$), 101.8 (benzylidine CH), 101.2 (C5), 80.8 (CH), 78.6 (C1'), 77.9 (CH), 75.5 (6'-CH$_2$), 72.9 (CH$_2$ONap), 71.5 (CH), 70.6 (quat). Note: *Between 128.5 and 125.1 lies one additional carbon that overlaps one of the others.

LCMS (Method G1), retention time=3.70 min, m/z=529.1 (M+H), 551.1 (M+Na), purity >99%.

f) Preparation of Compound 57 (Dihydroxylation, Periodate Cleavage and Reduction to the Alcohol)

To as stirred solution of Compound 56 (45 g, 85 mmoles) in 95% acetone (aq, 350 mL) was added N-methylmorpholine oxide (48 g, 409 mmoles) and 2.5% OsO$_4$ in isopropanol (70 mg OsO$_4$), and the reaction was allowed to stir at room temperature for 4 days. At that time, the reaction was filtered thru celite and silica gel, and eluted thoroughly with acetone. The resultant crude product was purified by column chromatography (2.5% to 5% methanol/DCM) to give the diol (19.74 g), which was immediately treated with THF (175 mL), H$_2$O (175 mL) and NaIO$_4$ (15 g, 70 mmoles). After 1 h, water and EtOAc were added and the organic was washed with saturated NaHCO$_3$ and brine and then dried (Na$_2$SO$_4$), filtered and the solvent removed under reduced pressure to give the crude aldehyde. This compound was immediately treated with 4 equivalents of NaBH$_4$ in methanol at 0° C. for 1 h, and then water and EtOAc were added and the organic was washed with, 10% citric acid (aq) and brine and then dried (Na$_2$SO$_4$), filtered and the solvent removed under reduced pressure to give the crude alcohol. The reaction was purified by silica gel chromatography, eluting with methanol/DCM to give Compound 57 (40% overall yield). $^1$H NMR and LCMS was consistent with structure.

g) Preparation of Compound 58 (Anhydro Formation)

To a stirred 0° C. mixture of Compound 57 (1,28 g, 2.4 mmoles) and triphenyl phosphine (2.2 g, 8.4 mmoles) in dry THF (20 mL) was added DIAD (1.6 mL, 8.4 mmoles) dropwise. After stirring at room temp for 18 hours, water and DCM were added and the organic was washed with brine and then dried (Na$_2$SO$_4$), filtered and the solvent removed under reduced pressure to give the crude bicyclic product. This was purified by silica gel chromatography (2% methanol/DCM to 10% methanol/DCM) to give the pure Compound 58 (1.11 g, 90%). $^1$H NMR and LCMS was consistent with structure.

h) Preparation of Compound 59

Compound 58 (1.1 g, 2.15 mmoles) was dissolved in DMF (15 mL) and treated with NaH (60% in mineral oil, 6.4 mmoles) for 15 minutes. At that time, NH$_4$Cl and EtOAc were added and the organic was washed with, water and brine and then dried (Na$_2$SO$_4$), filtered and the solvent removed under reduced pressure to give the crude compound. This was purified by silica gel chromatography (3% methanol/DCM) to give the pure Compound 59 (866 mg, 79%). $^1$H NMR and LCMS was consistent with structure.

i) Preparation of Compound 60 (Removal of Nap)

Compound 59 (800 mg, 1.6 mmoles) was dissolved in DCM (15 mL) and treated with water (1.5 mL) and DDQ (529 mg, 2.3 mmoles). After stirring for 16 hours, water and DCM were added and the organic was washed with, saturated NaHCO$_3$ and brine and then dried (Na$_2$SO$_4$), filtered and the solvent removed under reduced pressure to give the crude alcohol. The organics were back-extracted several times with DCM. The crude compound was co-evaporated with methanol/DCM (10 mL) and silica gel (1 g). After drying, this was applied directly to a silica gel column, and purified by silica gel chromatography (2% to 6% methanol/DCM) to give Compound 60 (409 mg, 70%). $^1$H NMR and LCMS was consistent with structure.

j) Preparation of Compound 61 (Barton-Macombie Deoxygenation)

A stirred mixture of Compound 60 (388 mg, 1.04 mmoles) and DMAP (343 mg, 2.8 mmoles) in CH$_3$CN (14 mL) at 0° C. was added phenylchlorothioformate (196 μL, 1.45 mmoles). After stirring for 4 hours, the reaction mixture was evaporated to dryness. Toluene (13 mL), Bu$_4$SnH (1.65 mL, 6.24 mmoles) and AlBN (15 mg) were heated at 90° C. for 4 h. The reaction was then evaporated to dryness, and purified by silica gel chromatography (1.5% to 3% methanol/DCM) to give Compound 61 (254 mg, 68%). $^1$H NMR and LCMS was consistent with structure.

k) Preparation of Compound 62 (Removal of the Benzylidine and DMT Protection)

A stirred mixture of Compound 61 (230 mg, 0.64 mmoles) was hydrogenated over 10% Pd/C (20 mg) at 40 psi for 10 hours. The reaction was filtered and evaporated and co-evaporated with toluene. After drying under reduced pressure for 16 hours, pyridine (3 mL) and DMTCl (187 mg, 0.55 mmoles) was added. The reaction was allowed to stir at room temperature for 4 hours, and water and EtOAc were added and the organic was washed with, saturated NaHCO$_3$ and brine and then dried (Na$_2$SO$_4$), filtered and the solvent removed under reduced pressure. The resultant foam was purified by silica gel chromatography (10% to 40% acetone/CH$_2$Cl$_2$) to give Compound 62 (171 mg, 47%). $^1$H NMR and LCMS was consistent with structure.

Example 28

Preparation of Compound 65

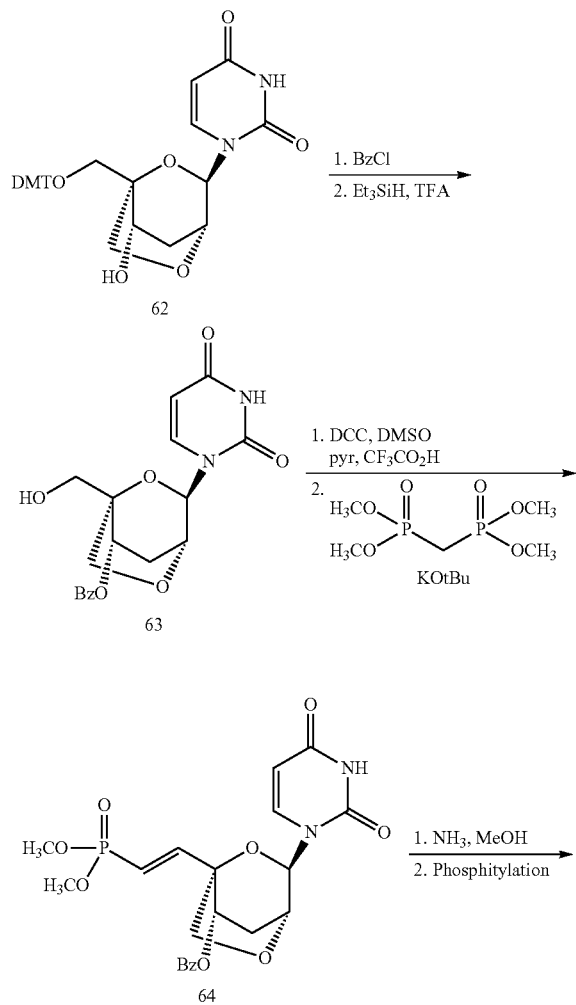

Compound 62 is prepared as per the procedures illustrated in Example 27.

Example 29

Preparation of Compound 69

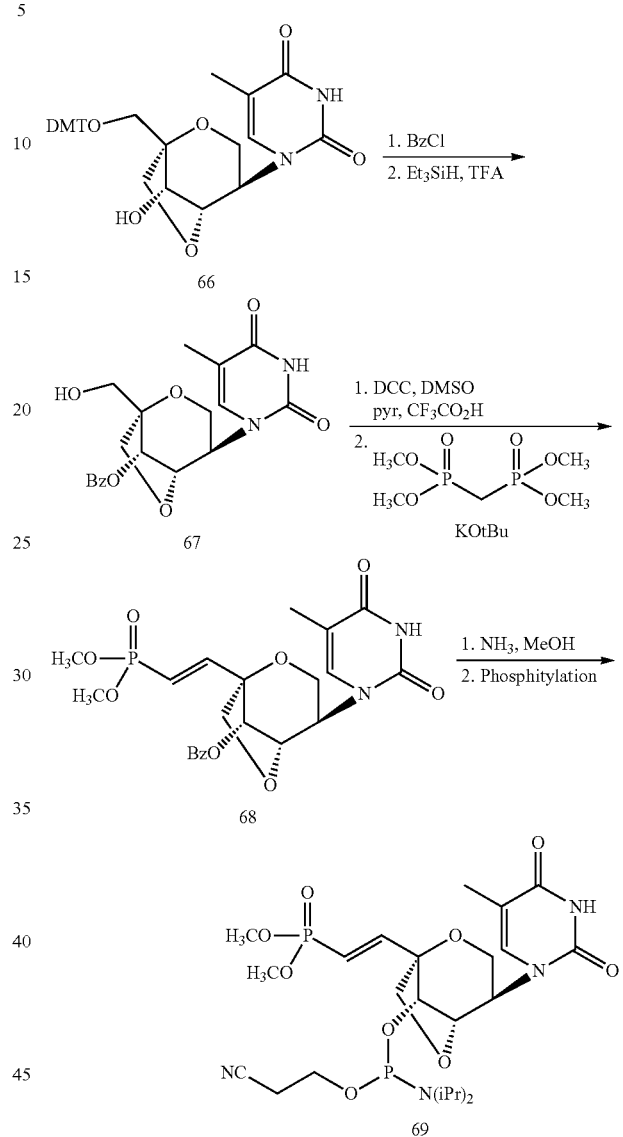

Compound 66 is prepared similar to published procedures (see International Application Number: PCT/US2009/033373, Published on Aug. 13, 2009 as WO 2009/100320).

Example 30

Preparation of Compound 73

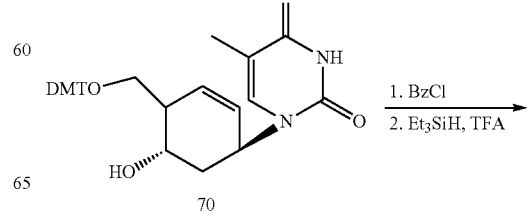

-continued
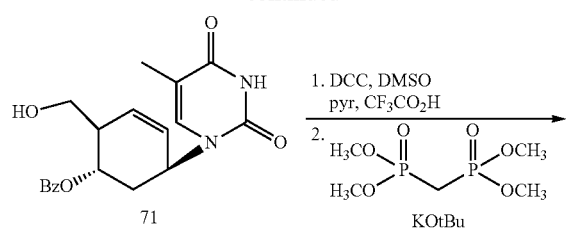
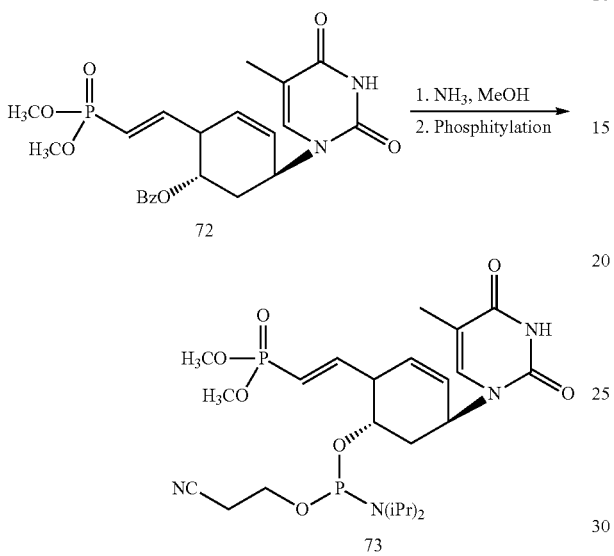
Compound 70 is prepared similar to published procedures (see Wang et al., *J. Am. Chem. Soc.*, 2000, 122 8595-8602).
Example 31
Preparation of Compound 77
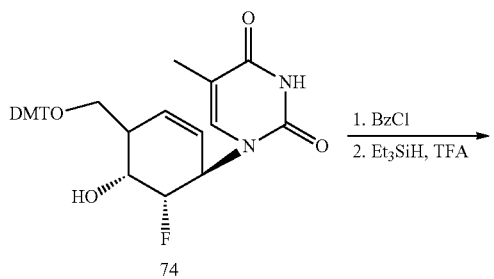
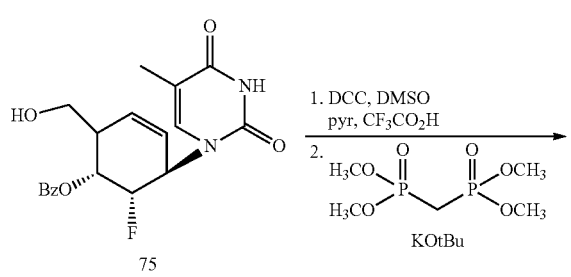
-continued
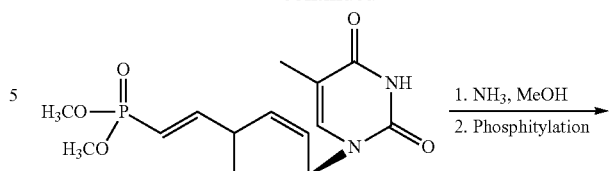
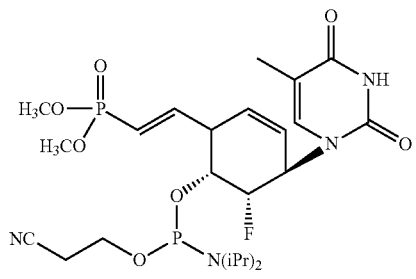
Compound 74 is prepared similar to published procedures (see International Application Number: PCT/US2009/058011, Published on Apr. 1, 2110, as WO 2010/036696).
Example 32
Preparation of Compound 81
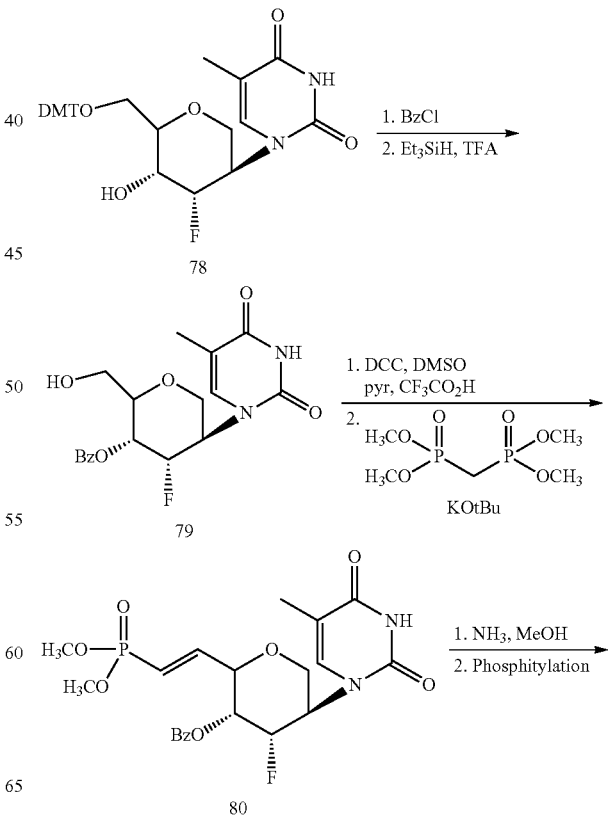

125
-continued
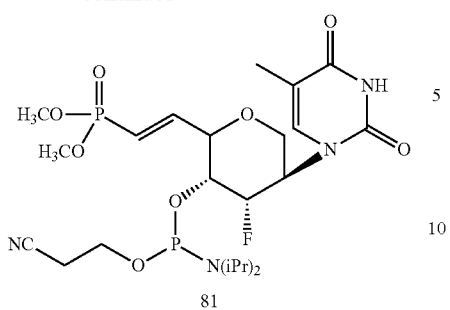
81
Compound 78 is prepared similar to published procedures (see International Application Number: PCT/US2008/073379, Published on Feb. 19, 2009, as WO 2009/023855).
Example 33
Preparation of Compound 85
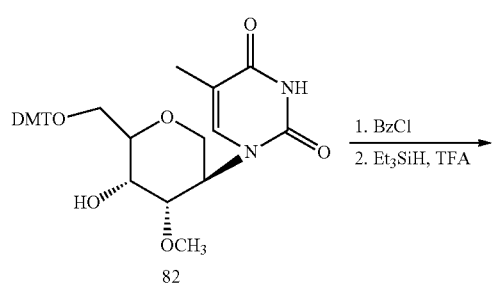
82
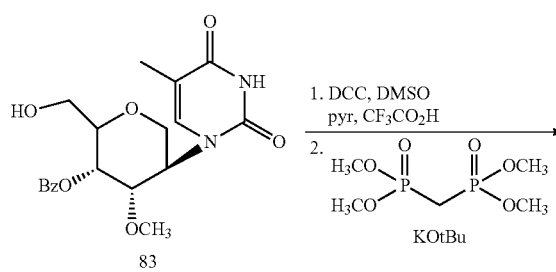
83
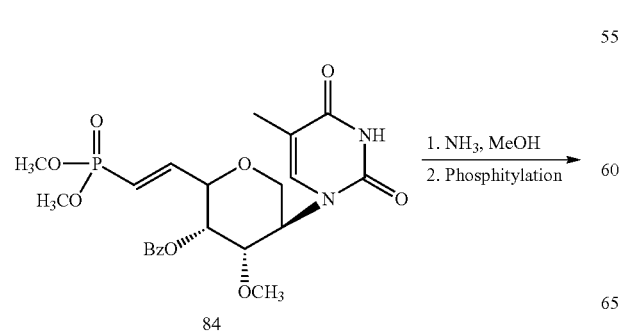
84
126
-continued
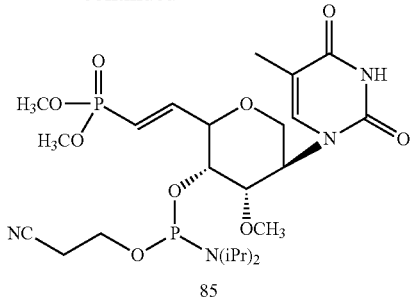
85
Compound 82 is prepared similar to published procedures (see Published US Application Number: US 2004/0033967).
Example 34
Preparation of Compound 89
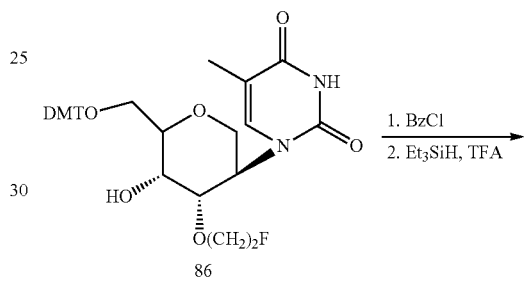
86
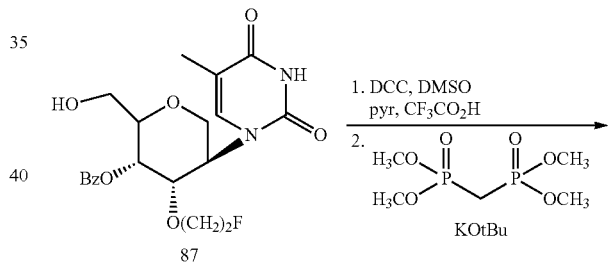
87
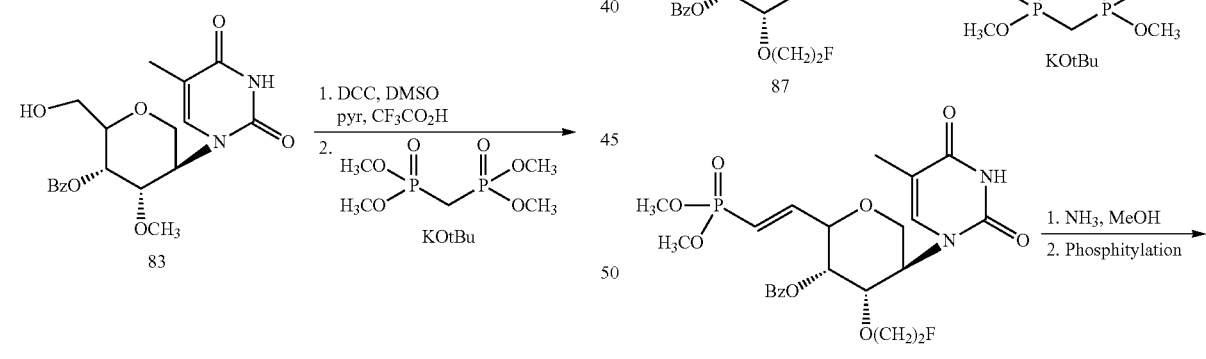
88
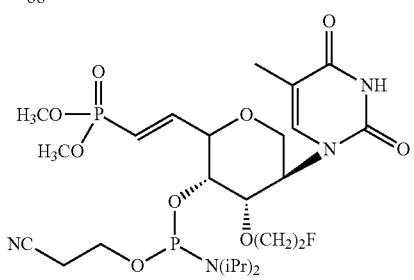
89

Compound 86 is prepared similar to published procedures (see International Application Number: PCT/US2010/022759, Published on Aug. 12, 2010 as WO 2010/090969).

Example 35

Preparation of Compound 93

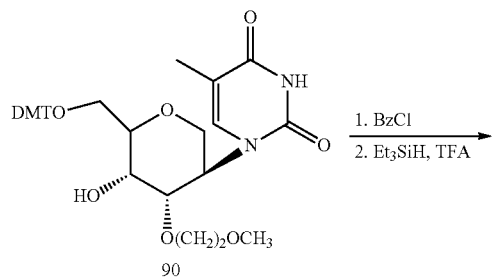
90

1. BzCl
2. Et₃SiH, TFA

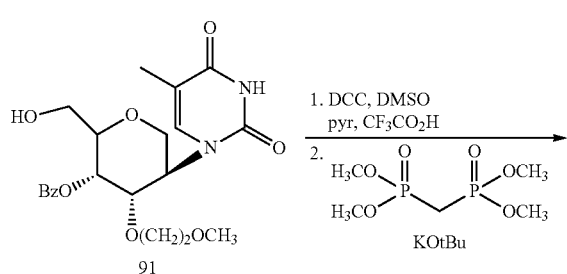
91

1. DCC, DMSO pyr, CF₃CO₂H
2. H₃CO-P(O)(OCH₃)-CH₂-P(O)(OCH₃)-OCH₃, KOtBu

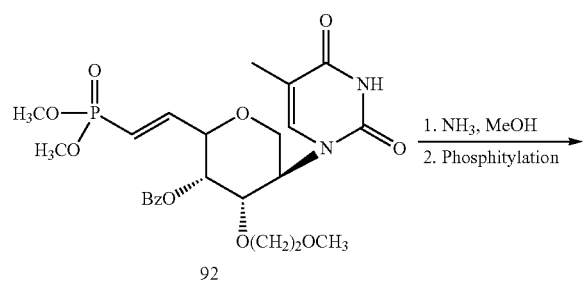
92

1. NH₃, MeOH
2. Phosphitylation

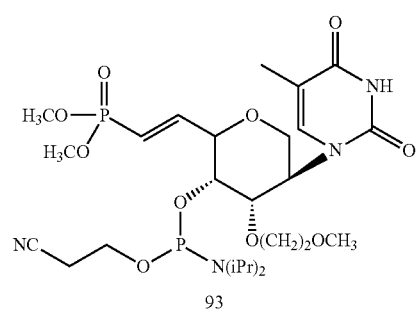
93

Compound 90 is prepared similar to published procedures (see International Application Number: PCT/US2010/022759, Published on Aug. 12, 2010 as WO 2010/090969).

Example 35a

Alternative Methods for the Preparation of Compound 50

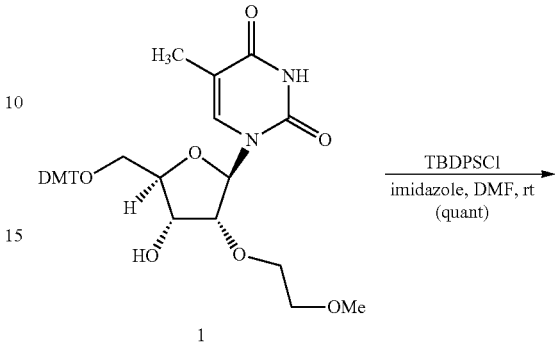
1

TBDPSCl
imidazole, DMF, rt
(quant)

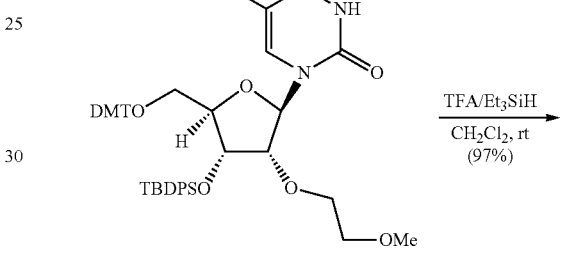
100

TFA/Et₃SiH
CH₂Cl₂, rt
(97%)

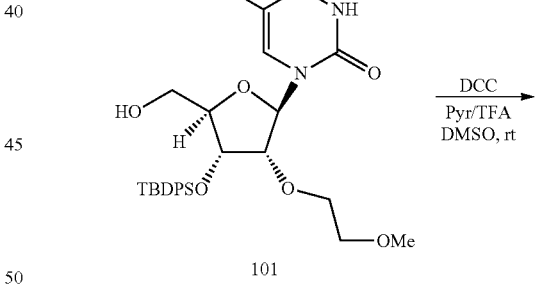
101

DCC
Pyr/TFA
DMSO, rt

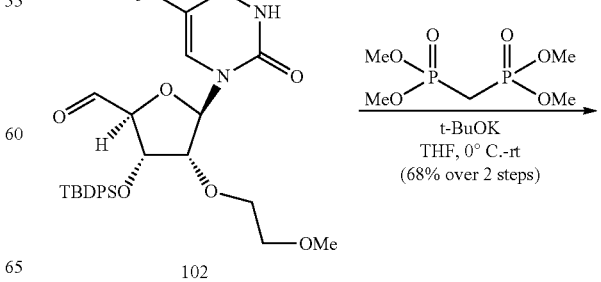
102

MeO-P(O)(OMe)-CH₂-P(O)(OMe)-OMe
t-BuOK
THF, 0° C.-rt
(68% over 2 steps)

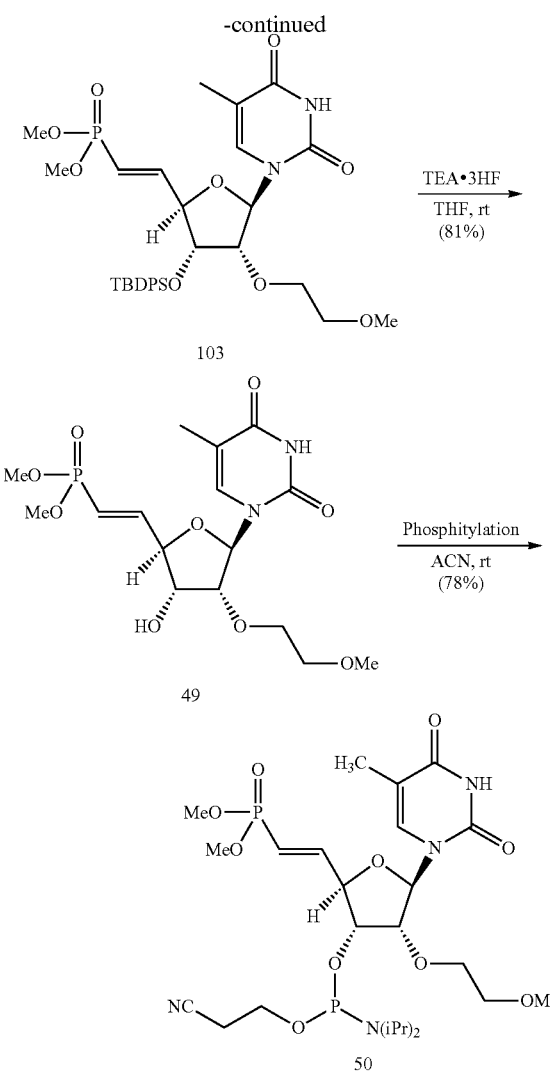

Compound 1 was prepared according to the procedures published in U.S. Pat. No. 5,969,116. Spectral analysis for Compound 50 was consistent with the structure.

Example 36

Oligomeric Compounds

Following synthetic procedures well known in the art, some of which are illustrated herein, oligomeric compounds are prepared having at least one 5' modified nucleoside of Formula II, IIa, IIb, IIc, IId or IIe, using one or more of the phosphoramidite compounds illustrated in the preceding examples (Example 13, Compound 5; Examples 15 and 25, Compound 14; Example 16, Compound 17; Example 17, Compounds 19 and 19a; Example 19, Compound 24; Example 20, Compound 27; Example 21, Compound 30; Example 22, Compound 32; Example 23, Compounds 36-38; Example 24, Compounds 42-44; Example 25, Compound 47; Examples 26 and 35a, Compound 50; Example 28, Compound 65; Example 29, Compound 69; Example30, Compound 73; Example 31, Compound 77; Example 32, Compound 81; Example 33, Compound 85; Example 34, Compound 89 and Example 35, Compound 93).

The (E)-vinyldimethylphosphonate phosphoramidite Compound 17 was incorporated into an oligomeric compound using either standard automated oligonucleotide synthesis techniques.

| SEQ ID NO./ ISIS NO. | Composition (5' to 3') |
|---|---|
| 05/505739 | PV-T$_{es}$U$_{fs}$G$_{m}$U$_{fs}$C$_{m}$U$_{fs}$C$_{m}$U$_{fs}$C$_{m}$U$_{fs}$G$_{m}$G$_{fs}$U$_{m}$C$_{fs}$C$_{m}$U$_{fs}$U$_{ms}$A$_{fs}$C$_{ms}$U$_{fs}$U$_{ms}$A$_{es}$A$_{e}$ |

A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, (PO(OH)$_2$(CH=CH—). Nucleosides followed by a subscript f, m or e are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside.

Example 37

General Method for the Preparation of Oligomeric Compounds Containing Modified Nucleosides as Provided Herein at the 5'-terminus Via Solid Phase Techniques (Preparation of 505739)

Unless otherwise stated, all reagents and solutions used for the synthesis of oligomeric compounds were purchased from commercial sources. Standard phosphoramidites and solid support were used for incorporation of A, U, G, $^{me}$C and C residues. A 0.1 M solution of 2'-F and 2'-O-Me phosphoramidites in anhydrous acetonitrile (CH$_3$CN) along with 2'-O-MOE-5'-deoxy-5'-methylenediethylphosphonate and 2'-O-MOE-deoxy-5'-vinyldimethylphosphonate 3'-phosphoramidites in 30% dichloromethane (CH$_2$Cl$_2$) in anhydrous CH$_3$CN were used for the synthesis. The oligomeric compounds were synthesized on VIMAD UnyLinker™ solid support and the appropriate amounts of solid support were packed in the column for synthesis. Dichloroacetic acid (6%) in toluene was used as detritylating reagent. 4,5-Dicyanoimidazole in the presence of N-methylimidazole or 1H-tetrazole in CH$_3$CN was used as activator during the coupling step. The synthesis of oligomeric compounds was performed either on an AKTAOligopilot synthesizer (GE Healthcare Bioscience) or an ABI394 synthesizer (Applied Biosystems) on a 2-200 μmol scale using the procedures set forth below.

A solid support preloaded with the Unylinker™ was loaded into a synthesis column after closing the column bottom outlet and CH$_3$CN was added to form a slurry. The swelled support-bound Unylinker™ was treated with a detritylating reagent containing 6% dichloroacetic acid in toluene to provide the free hydroxyl groups. During the coupling step, four to fourteen equivalents of phosphoramidite solutions were delivered with coupling for 10 minutes. All of the other steps followed standard protocols. Phosphorothioate linkages were introduced by sulfurization with a 0.05 M solution of DDTT (3-((dimethylamino-methylidene)amino)-3H-1,2,4-dithiazole-3-thione) in 1:1 pyridine/CH$_3$CN for a contact time of 3 minutes. Phosphite triester internucleoside linkages were oxidized to phosphate diester internucleoside linkages using a solution of tert-butyl hydroperoxide/CH$_3$CN/water (10:87:3) over 12 minutes.

After the desired sequence was assembled, the solid support bound oligomeric compound was washed with $CH_2Cl_2$ and dried under high vacuum. After 4 hrs, the dried solid support was suspended in a solution of iodotrimethylsilane (TMSI) and pyridine in $CH_2Cl_2$ to remove the 5'-phosphonate protecting group (ethyl ether or methyl ether). The deprotection solution was prepared by dissolving 0.75 mL TMSI and 0.53 mL pyridine in 28.2 mL $CH_2Cl_2$ (used 0.5 mL/μmol of solid support). After 30 min at room temperature, the reaction was quenched with 1M 2-mercaptoethanol in 1:1 TEA/$CH_3CN$ (used 0.5 mL/μmol of solid support). The supernatant was decanted and the solid-support was washed with additional 2-mercaptoethanol solution. After 45 minutes at room temperature the wash step with additional 2-mercaptoethanol solution was repeated. The supernatant was decanted and the solid-support bound oligomeric compound was suspended in ammonia (28-30 wt %) in 1 M 2-mercaptoethanol (used 0.75 mL/μmol of solid support) and heated at 55° C. for 2 hrs to cleave the oligomeric compound from the solid support.

The cleaved solution was allowed to cool to ambient temperature (20° C.) for 24 hrs. The unbound oligomeric compound was then filtered and the support was rinsed and filtered with water:ethanol (1:1) followed by water. The filtrate was combined and concentrated to dryness. The residue obtained was purified by HPCL on a reverse phase column (Waters X-Bridge C-18 5μm, 19×250 mm, A=5 mM tributylammonium acetate in 5% aqueous $CH_3CN$, B =$CH_3CN$, 0 to 90% B in 80 min, flow 7 mL min$^{-1}$, λ=260 nm). Fractions containing full-length oligomeric compound were pooled together (assessed by LC/MS analysis >95%) and the tributylammonium counter ion was exchanged to sodium by HPLC on a strong anion exchange column (GE Healthcare Bioscience, Source 30Q, 30 μm, 2.54×8 cm, A=100 mM ammonium acetate in 30% aqueous $CH_3CN$, B=1.5 M NaBr in A, 0-40% of B in 60 min, flow 14 mL min$^{-1}$). The residue was desalted by HPLC on a reverse phase column to yield the oligomeric compound in an isolated yield of 15-20% based on solid-support loading. The unbound oligomeric compound was characterized by ion-pair-HPLC-MS analysis with Agilent 1100 MSD system.

| SEQ ID NO./ ISIS NO. | Composition (5' to 3') |
|---|---|
| 05/505739 | Pv-$T_{es}U_{fs}G_mU_{fs}C_mU_{fs}C_mU_{fs}G_mG_{fs}U_mC_{fs}C_mU_{fs}U_{ms}A_{fs}C_{ms}U_{fs}U_{ms}A_{es}A_e$ |

A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, $(PO(OH)_2(CH=CH—)$. Nucleosides followed by a subscript f, m or e are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside.

Example 38

Preparation of Modified Oligomeric Compounds Comprising a Modified 5'-nucleoside (5'-deoxy-5'-methylenediethylphosphonate and 5'-deoxy-5'-vinyldimethylphosphonate)

Oligomeric compounds were prepared on either a 2 or 200 μmol scale following procedures illustrated in Example 37. Both ÄKTAOligopilot synthesizer (GE Healthcare Bioscience) and ABI394 synthesizer (Applied Biosystems) were used for particular runs. The unbound oligomeric compounds were cleaved from the solid support and analyzed by ion-pair-HPLC-MS.

| SEQ ID NO./ ISIS NO. | Composition (5' to 3') |
|---|---|
| 05/508027 | Pv-$T_{es}U_{fs}G_mU_{fs}C_mU_{fs}C_mU_{fs}G_mG_{fs}U_mC_{fs}C_mU_{fs}U_{ms}A_{fs}C_{ms}U_{fs}U_{ms}A_{es}A_e$ |
| 05/505739 | Pv-$T_{es}U_{fs}G_mU_{fs}C_mU_{fs}C_mU_{fs}G_mG_{fs}U_mC_{fs}C_mU_{fs}U_{ms}A_{fs}C_{ms}U_{fs}U_{ms}A_{es}A_e$ |
| 06/508016 | Py-$T_{es}U_{fs}A_mU_{fs}C_mU_{fs}A_mU_{fs}A_mA_{fs}U_mG_{fs}A_mU_{fs}C_{ms}A_{fs}G_{ms}G_{fs}U_{ms}A_{es}A_e$ |
| 06/522247 | Pv-$T_{es}U_{fs}A_mU_{fs}C_mU_{fs}A_mU_{fs}A_mA_{fs}U_mG_{fs}A_mU_{fs}C_{ms}A_{fs}G_{ms}G_{fs}U_{ms}A_{es}A_e$ |
| 07/508015 | Py-$T_{es}G_{fs}A_mA_{fs}C_mA_{fs}U_mU_{fs}G_mG_{fs}A_mA_{fs}U_mA_{fs}G_{ms}U_{fs}U_{ms}U_{fs}C_{ms}A_{es}A_e$ |
| 07/522246 | Pv-$T_{es}G_{fs}A_mA_{fs}C_mA_{fs}U_mU_{fs}G_mG_{fs}A_mA_{fs}U_mA_{fs}G_{ms}U_{fs}U_{ms}U_{fs}C_{ms}A_{es}A_e$ |

A subscript "s" between two nucleosides indicates a phosphorothioate internucleoside linkage (going 5' to 3'). The absence of a subscript "s" between two nucleosides indicates a phosphodiester internucleoside linkage. A "Py" at the 5'-end indicates a 5'-methylenediethylphosphonate group, $(PO(OCH_2CH_3)_2(CH_2CH_2—)$. A "Pv" at the 5'-end indicates a 5'-(E)-vinylphosphonate group, $(PO(OH)_2(CH=CH—)$. Nucleosides followed by a subscript f, m or e are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside.

Example 39

General Method for the Preparation of C16- and Cholesterol-Conjugated Oligomeric Compounds 95 and 96

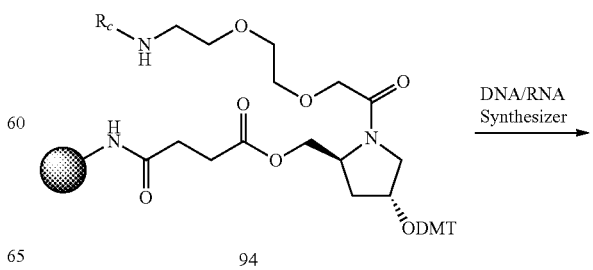

94

133

-continued

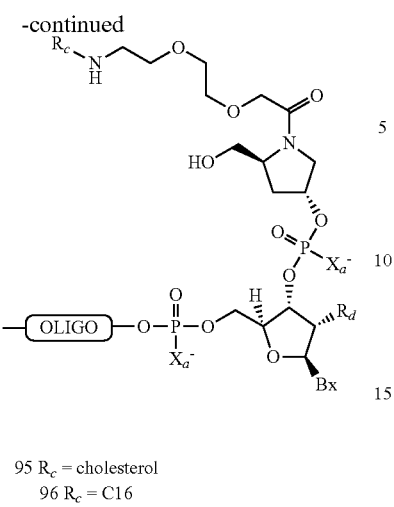

95 $R_c$ = cholesterol
96 $R_c$ = C16

$B_x$ = heterocyclic base moiety
$R_d$ = sugar substituent group
$X_a$ = O or S

= solid support

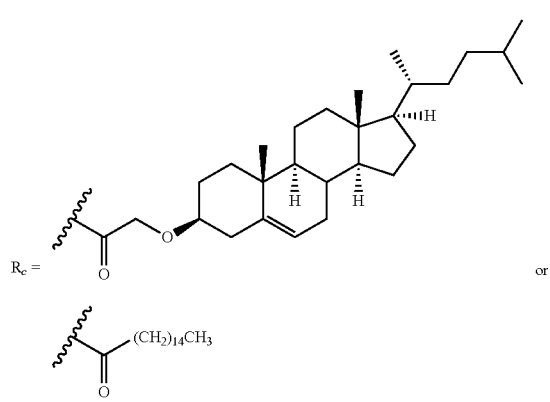

$R_c$ =    or

134

Compound 94 and conjugated oligomeric Compounds 95 and 96 are prepared according to published procedures (see Swayze et al., WO 2006/031461) and procedures illustrated in Example 37.

Example 40

Preparation of C16- and Cholesterol-Conjugated Oligomeric Compounds

The C 16 and cholesterol conjugated oligomeric compounds shown below were prepared as per the procedures illustrated in Examples 38 and 39.

| SEQ ID NO./ ISIS NO. | Composition (5' to 3') |
|---|---|
| 06/526608 | Pv-$T_{es}U_{fs}A_mU_{fs}C_mU_{fs}A_mU_{fs}A_mA_{fs}U_mG_{fs}A_mU_{fs}C_mA_{fs}G_mG_{fs}$ $U_{ms}A_{es}A_e$-C16 |
| 06/527155 | Pv-$T_{es}U_{fs}A_mU_{fs}C_mU_{fs}A_mU_{fs}A_mA_{fs}U_mG_{fs}A_mU_{fs}C_mA_{fs}G_{ms}$ $G_{fs}U_{ms}A_{es}A_e$-Cholesterol |

A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group (PO(OH)$_2$ (CH=CH—). Nucleosides followed by a subscript f, m or e are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. The C16 alkyl chain and cholesterol conjugated through a pyrrolidine linker are shown below.

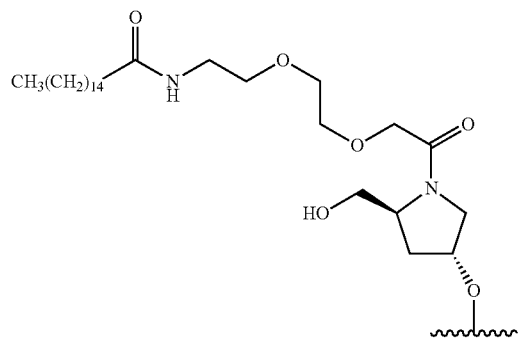

C16

-continued
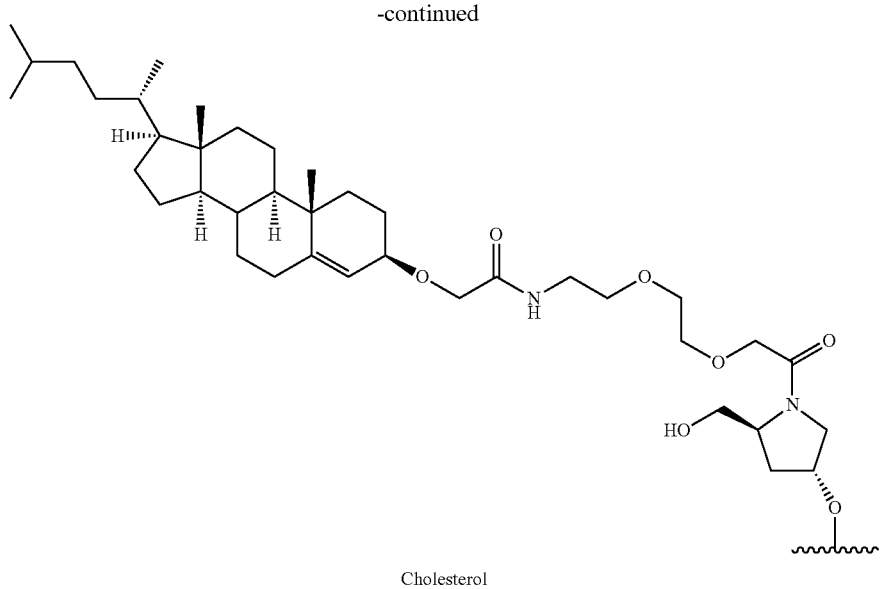
Cholesterol
The conjugated oligomeric compounds were cleaved from the solid support and analyzed by ion-pair-HPLC-MS.
| Calculated/<br>ISIS NO. | Calculated<br>Mass (Da) | Observed<br>Mass (Da) |
|---|---|---|
| 06/526608 | 7879.2 | 7877.6 |
| 06/527155 | 8067.5 | 8066.5 |
Example 41
General Method for the Preparation of C10-Conjugated Oligomeric Compound 99
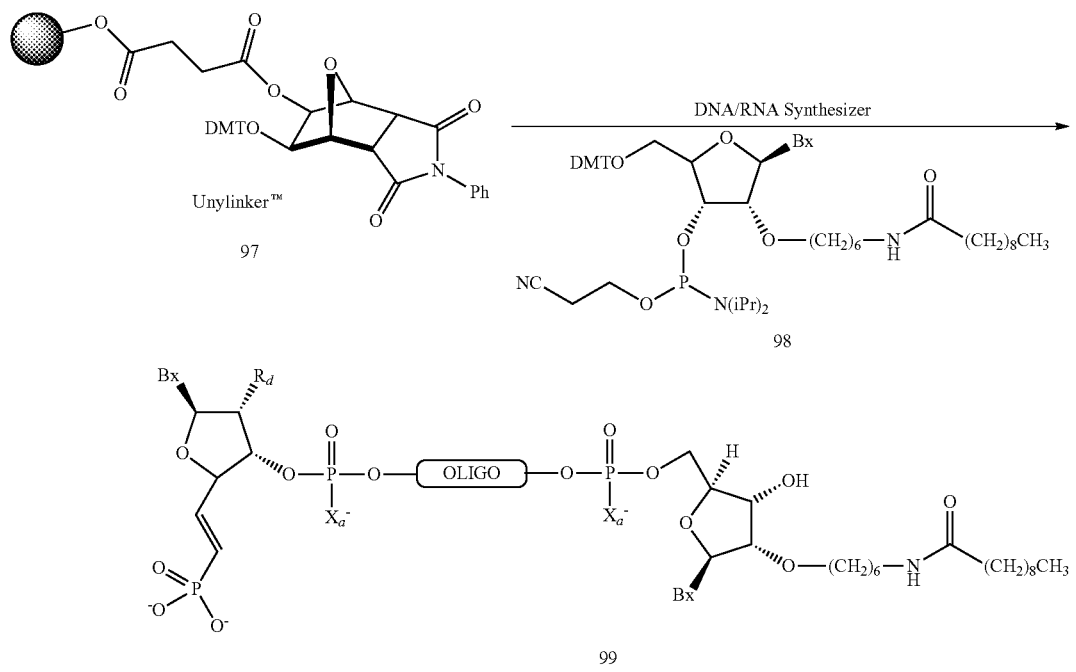

-continued $B_x$ = heterocyclic base moiety
$R_d$ = sugar substituent group
$X_a$ = O or S

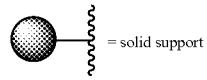 = solid support

The Unylinker 97 is commercially available. Conjugated oligomeric Compound 99 is prepared similar to published procedures (see Swayze et al., WO 2006/031461) and procedures illustrated in Examples 38 and 39.

Example 42

Preparation of C10-Conjugated Oligomeric Compounds

The C10-conjugated oligomeric compounds shown below are prepared as per the procedures illustrated in Example 41 with C10 conjugate attached to either at the 3' or at any internal positions of the oligomeric compound.

| SEQ ID NO./ ISIS NO. | Composition (5' to 3') |
|---|---|
| 08/530333 | Pv-$T_{es}U_{fs}G_mU_{fs}C_mU_{fs}C_mU_{fs}G_mG_{fs}U_mC_{fs}C_mU_{fs}U_{ms}A_{fs}C_{ms}U_{fs}T_{C10s}A_{es}A_e$ |
| 09/530334 | Pv-$T_{es}U_{fs}G_mU_{fs}C_mU_{fs}C_mU_{fs}G_mG_{fs}U_mC_{fs}C_mU_{fs}T_{C10s}A_{fs}C_{ms}U_{fs}U_{ms}A_{es}A_e$ |
| 10/530335 | Pv-$T_{es}U_{fs}G_mU_{fs}C_mU_{fs}C_mU_{fs}G_mG_{fs}T_{C10}C_{fs}C_mU_{fs}U_{ms}A_{fs}C_{ms}U_{fs}U_{ms}A_{es}A_e$ |
| 11/530336 | Pv-$T_{es}U_{fs}G_mU_{fs}C_mT_{C10s}C_mU_{fs}G_mG_{fs}U_mC_{fs}C_mU_{fs}U_{ms}A_{fs}C_{ms}U_{fs}U_{ms}A_{es}A_e$ |
| 12/530337 | Pv-$T_{es}U_{fs}G_mU_{fs}C_mU_{fs}C_mU_{fs}G_mG_{fs}U_mC_{fs}C_mU_{fs}U_{ms}A_{fs}C_{ms}U_{fs}U_{ms}A_{es}T_{C10}$ |

A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, $(PO(OH)_2(CH=CH—)$. Nucleosides followed by a subscript f, m or e are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. Nucleosides with a subscript "C10" are shown below.

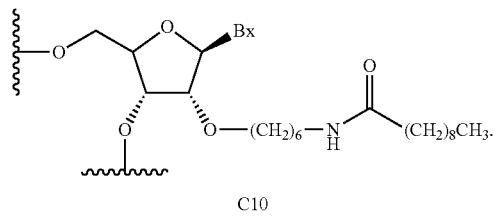

C10

Example 43

Modified ssRNAs Targeting PTEN—In Vitro Study

A series of modified single strand RNAs (ssRNAs) were prepared and tested for their ability to reduce PTEN mRNA expression levels in HeLa cells and hepatocytes. HeLa cells and hepatocytes were treated with the modified single stranded oligomeric compounds shown below using transfection methods such as LIPOFECTAMINE™ 2000 (Lipo) or electroporation (Electro) as described herein. The $IC_{50}$'s were calculated using the linear regression equation generated by plotting the normalized mRNA levels to the log of the concentrations used. The modified ssRNAs with an asterisk (*) were tested in a separate assay and their $IC_{50}$'s are presented below.

| SEQ ID NO./ ISIS NO. | Composition (5' to 3') |
|---|---|
| 05/518560* | Px-$T_{es}U_{fs}G_mU_{fs}C_mU_{fs}C_mU_{fs}G_mG_{fs}U_mC_{fs}C_mU_{fs}U_mA_{fs}C_{ms}U_{fs}U_{ms}A_{es}A_e$ |
| 05/515658* | Pz-$T_{es}U_{fs}G_mU_{fs}C_mU_{fs}C_mU_{fs}G_mG_{fs}U_mC_{fs}C_mU_{fs}U_{ms}A_{fs}C_{ms}U_{fs}U_{ms}A_{es}A_e$ |
| 05/515660* | Pyy-$T_{es}U_{fs}G_mU_{fs}C_mU_{fs}C_mU_{fs}G_mG_{fs}U_mC_{fs}C_mU_{fs}U_{ms}A_{fs}C_{ms}U_{fs}U_{ms}A_{es}A_e$ |
| 05/447581 | P-$T_RU_{fs}G_mU_{fs}C_mU_{fs}C_mU_{fs}G_mG_{fs}U_mC_{fs}C_mU_{fs}U_{ms}A_{fs}C_{ms}U_{fs}U_{ms}A_{es}A_e$ |
| 05/508027 | Py-$T_{es}U_{fs}G_mU_{fs}C_mU_{fs}C_mU_{fs}G_mG_{fs}U_mC_{fs}C_mU_{fs}U_{ms}A_{fs}C_{ms}U_{fs}U_{ms}A_{es}A_e$ |
| 05/505739 | Pv-$T_{es}U_{fs}G_mU_{fs}C_mU_{fs}C_mU_{fs}G_mG_{fs}U_mC_{fs}C_mU_{fs}U_{ms}A_{fs}C_{ms}U_{fs}U_{ms}A_{es}A_e$ |
| 06/508016 | Py-$T_{es}U_{fs}A_mU_{fs}C_mU_{fs}A_mU_{fs}A_mA_{fs}U_mG_{fs}A_mU_{fs}C_{ms}A_{fs}G_{ms}G_{fs}U_{ms}A_{es}A_e$ |
| 06/522247 | Pv-$T_{es}U_{fs}A_mU_{fs}C_mU_{fs}A_mU_{fs}A_mA_{fs}U_mG_{fs}A_mU_{fs}C_{ms}A_{fs}G_{ms}G_{fs}U_{ms}A_{es}A_e$ |
| 07/508015 | Py-$T_{es}G_{fs}A_mA_{fs}C_mA_{fs}U_mU_{fs}G_mG_{fs}A_mA_{fs}U_mA_{fs}G_{ms}U_{fs}U_{ms}U_{fs}C_{ms}A_{es}A_e$ |
| 07/522246 | Pv-$T_{es}G_{fs}A_mA_{fs}C_mA_{fs}U_mU_{fs}G_mG_{fs}A_mA_{fs}U_mA_{fs}G_{ms}U_{fs}U_{ms}U_{fs}C_{ms}A_{es}A_e$ |
| 13/116847 | $^{me}C_{es}T_{es}G_{es}^{me}C_{es}T_{es}A_{ds}G_{ds}^{me}C_{ds}^{me}C_{ds}T_{ds}^{me}C_{ds}T_{ds}G_{ds}G_{ds}A_{ds}T_{es}T_{es}T_{es}G_{es}A_e$ |

A subscript "s" between two nucleosides indicates a phosphorothioate internucleoside linkage (going 5' to 3'). The absence of a subscript "s" between two nucleosides indicates a phosphodiester internucleoside linkage. A "Px" at the 5'-end indicates a 5'-(E)-(F-vinyl)phosphonate group, $(PO(OH)_2(CF=CH—)$. A "Pz" at the 5'-end indicates a 5'-(Z)—(F-vinyl)phosphonate group, $(PO(OH)_2(CF=CH—)$. A "Pyy" at the 5'-end indicates a 5'-(F-methylene)phosphonate group, $(PO(OH)_2(CHFCH_2—)$. A "P" at the 5'-end indicates a 5'-phosphate group. A "Py" at the 5'-end indicates a 5'-methylenephosphonate group, $(PO(OH)_2(CH_2CH_2—)$. A "Pv" at the 5'-end indicates a 5'-(E)-vinylphosphonate group, $(PO(OH)_2(CH=CH—)$. $^{me}C$ indicates a 5-methyl cytosine nucleoside. Nucleosides followed by a subscript "d" are β-D-2'-deoxyribonucleosides. Nucleosides followed by a subscript f, m or e are sugar modified nucleosides. A subscript "f" indicates a 2'-fluoro modified nucleoside, a subscript "m"

indicates a 2'-O-methyl modified nucleoside and a subscript "e" indicates a 2'-O-methoxyethyl (MOE) modified nucleoside. Nucleosides with subscript "R" are shown below.

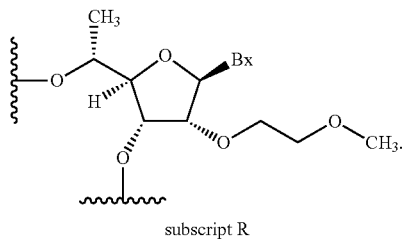

subscript R

| SEQ ID NO./ ISIS NO. | Chemistry | IC$_{50}$ (nM) | | |
|---|---|---|---|---|
| | | HeLa/Lipo | Hepato/ Lipo | Hepato/ Electro |
| 05/518560* | 5'-(E)-PO(OH)$_2$CF═CH— | 7.5 | — | — |
| 05/515658* | 5'-(Z)-PO(OH)$_2$CF═CH— | 40.2 | — | — |
| 05/515660* | 5'-PO(OH)$_2$(CHFCH$_2$)— | 7.6 | — | — |
| 05/447581 | 5'-(R)—Me | 1.1 ± 0.3 | 0.6 ± 0.3 | 2.5 ± 0.7 |
| 05/508027 | 5'-PO(OH)$_2$(CH$_2$CH$_2$)— | 20 | 35 | — |
| 05/505739 | 5'-(E)-PO(OH)$_2$CH═CH— | 2.3 ± 1 | 8 | — |
| 06/508016 | 5'-PO(OH)$_2$(CH$_2$CH$_2$)— | 2.3 ± 0.7 | 0.8 | 3 |
| 06/522247 | 5'-(E)-PO(OH)$_2$CH═CH— | 1.5 ± 0.7 | 0.4 | 2 |
| 07/508015 | 5'-PO(OH)$_2$(CH$_2$CH$_2$)— | 4.5 ± 2.0 | 4.5 | 10 |
| 07/522246 | 5'-(E)-PO(OH)$_2$CH═CH— | 1.7 ± 0.5 | 1.5 | 2 |
| 13/116847 | 5-10-5 MOE Gapmer | 1.9 ± 0.2 | 0.5 ± 0.1 | 0.53 ± 0.2 |

Example 44

Modified ssRNAs Comprising Modifications at the 3' Terminus Targeting PTEN—In Vitro Study A series of modified single strand RNAs (ssRNAs) comprising modifications at the 3' terminus were prepared and tested for their ability to reduce PTEN mRNA expression levels in HeLa cells. HeLa cells were treated with the modified single stranded oligomeric compounds shown below using LIPOFECTAMINE™ 2000 as a transfection reagent as described herein. The IC$_{50}$'s were calculated using the linear regression equation generated by plotting the normalized mRNA levels to the log of the concentrations used and are presented below.

| SEQ ID NO./ ISIS NO. | Composition (5' to 3') |
|---|---|
| 06/522247 | Pv-T$_{es}$U$_{fs}$A$_m$U$_{fs}$C$_m$U$_{fs}$A$_m$U$_{fs}$A$_m$A$_{fs}$U$_m$G$_{fs}$A$_m$U$_{fs}$C$_{ms}$A$_{fs}$G$_{ms}$G$_{fs}$ U$_{ms}$A$_{es}$A$_e$ |
| 06/538541 | Pv-T$_{es}$U$_{fs}$A$_m$U$_{fs}$C$_m$U$_{fs}$A$_m$U$_{fs}$A$_m$A$_{fs}$U$_m$G$_{fs}$A$_m$U$_{fs}$C$_{fs}$A$_{fs}$G$_{fs}$G$_{fs}$ U$_{fs}$A$_{es}$A$_e$ |
| 14/538539 | Pv-T$_{es}$U$_{fs}$A$_m$U$_{fs}$C$_m$U$_{fs}$A$_m$U$_{fs}$A$_m$A$_{fs}$U$_m$G$_{fs}$A$_m$T$_{ds}$C$_{ds}$A$_{ds}$G$_{ds}$G$_{ds}$ T$_{ds}$A$_{es}$A$_e$ |
| 15/538542 | Pv-T$_{es}$U$_{fs}$A$_m$U$_{fs}$C$_m$U$_{fs}$A$_m$U$_{fs}$A$_m$A$_{fs}$U$_m$G$_{fs}$A$_m$U$_{fs}$C$_{ds}$A$_{fs}$G$_{ds}$G$_{fs}$ T$_{ds}$A$_{es}$A$_e$ |

A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, $(PO(OH)_2(CH{=}CH$—). Nucleosides followed by a subscript "d" are β-D-2'-deoxyribonucleosides. Nucleosides followed by a subscript f, m or e are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside.

| SEQ ID NO./ ISIS NO. | Chemistry at 3' terminus | $IC_{50}$ (nM) |
|---|---|---|
| 06/522247 | Alt 2'-F/2'-OMe | 1.5 |
| 06/538541 | 6 2'-F | 1.8 |
| 14/538539 | 6 DNA | >50 |
| 15/538542 | 3 DNA | 3 |

Example 45

Modified ssRNAs comprising Ct Least One FHNA Targeting PTEN—In Vitro Study

A series of modified single strand RNAs (ssRNAs) comprising at least one FHNA were prepared and tested for their ability to reduce PTEN mRNA expression levels in HeLa cells. HeLa cells were treated with the modified single stranded oligomeric compounds shown below using LIPOFECTAMINE™ 2000 as a transfection reagent as described herein. The $IC_{50}$'s were calculated using the linear regression equation generated by plotting the normalized mRNA levels to the log of the concentrations used and are presented below. The modified ssRNAs with an asterisk (*) were tested in a separate assay and their $IC_{50}$'s are presented below.

| SEQ ID NO./ ISIS NO. | Composition (5' to 3') |
|---|---|
| 06/522247 | Pv-$T_{es}U_{fs}A_{m}U_{fs}C_{m}U_{fs}A_{m}U_{fs}A_{m}A_{fs}U_{m}G_{fs}A_{m}U_{fs}C_{ms}A_{fs}G_{ms}G_{fs}U_{ms}A_{es}A_{e}$ |
| 06/537789 | Pv-$T_{es}U_{fs}A_{m}U_{fs}C_{m}U_{fs}A_{h}U_{fs}A_{h}A_{fs}U_{m}G_{fs}A_{h}U_{fs}C_{ms}A_{fs}G_{hs}G_{fs}U_{ms}A_{hs}A_{h}$ |
| 16/545470 | Pv-$T_{es}U_{fs}A_{m}U_{fs}C_{m}T_{hs}A_{m}U_{fs}A_{m}A_{hs}U_{m}G_{fs}A_{m}T_{hs}C_{ms}A_{fs}G_{ms}G_{hs}U_{ms}A_{hs}A_{h}$ |
| 17/537790 | Pv-$T_{es}U_{fs}A_{m}U_{fs}C_{m}U_{fs}A_{m}U_{fs}A_{g}A_{fs}T_{h}G_{fs}A_{h}U_{fs}{}^{me}C_{hs}A_{fs}G_{hs}G_{fs}T_{hs}A_{hs}A_{h}$ |
| 17/537791* | Pv-$T_{es}U_{fs}A_{m}U_{fs}{}^{me}C_{h}U_{fs}A_{h}U_{fs}A_{h}A_{fs}T_{h}G_{fs}A_{h}U_{fs}{}^{me}C_{hs}A_{fs}G_{hs}G_{fs}T_{hs}A_{hs}A_{h}$ |
| 17/538740* | Pv-$T_{es}U_{fs}A_{h}U_{fs}{}^{me}C_{h}U_{fs}A_{h}U_{fs}A_{h}A_{fs}T_{h}G_{fs}A_{h}U_{fs}{}^{me}C_{hs}A_{fs}G_{hs}G_{fs}T_{hs}A_{hs}A_{h}$ |

A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, $(PO(OH)_2(CH=CH—)$. Nucleosides followed by a subscript f, m, e or h are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. Nucleosides with subscripts "h" are FHNA and are shown below.

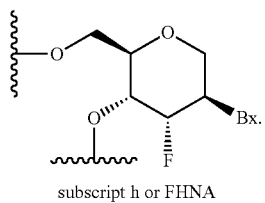

subscript h or FHNA

| SEQ ID NO./ ISIS NO. | Chemistry | $IC_{50}$ (nM) |
|---|---|---|
| 06/522247 | Alt 2'-F/2'-OMe | 5 |
| 06/537789 | 4 FHNA | 6 |
| 16/545470 | 4 FHNA | 6 |
| 17/537790 | 6 FHNA | >50 |
| 17/537791* | 8 FHNA | >50 |
| 17/538740* | 10 FHNA | >50. |

Example 46

Modified ssRNAs targeting FVII, eIF4E and Target X—In Vitro Study

A series of modified single strand RNAs (ssRNAs) were prepared and tested for their ability to reduce FVII, eIF4E and Target X mRNA expression levels in hepatocytes or HeLa cells. Hepatocytes or HeLa cells were treated with the modified single stranded oligomeric compounds shown below using LIPOFECTAMINE™ 2000 as a transfection reagent as described herein. The $IC_{50}$'s were calculated using the linear regression equation generated by plotting the normalized mRNA levels to the log of the concentrations used. The assay was performed independently for each target reduction and the $IC_{50}$'s for the modified ssRNAs are presented below. The sequences X1, X2 and X3 are targeted to Target X.

A subscript "s" between two nucleosides indicates a phosphorothioate internucleoside linkage (going 5' to 3'). The absence of a subscript "s" between two nucleosides indicates a phosphodiester internucleoside linkage. An "N" is a U, T, C, $^{me}C$, G or A nucleoside. A "Pv" at the 5'-end indicates a 5'-(E)-vinylphosphonate group, $(PO(OH)_2(CH=CH—)$. $^{me}C$ indicates a 5-methyl cytosine nucleoside. Nucleosides followed by a subscript "d" are β-D-2'-deoxyribonucleosides. Nucleosides followed by a subscript "r" are ribonucleosides. Nucleosides followed by a subscript f, m, e or k are sugar modified nucleosides. A subscript "f" indicates a 2'-fluoro modified nucleoside, a subscript "m" indicates a 2'-O-methyl modified nucleoside, a subscript "e" indicates a 2'-O-methoxyethyl (MOE) modified nucleoside. Nucleosides with subscripts "k" are (S)-cEt and are shown below.

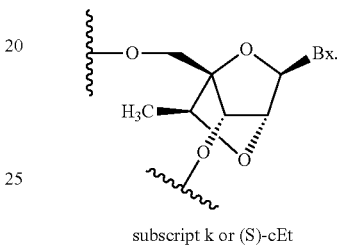

subscript k or (S)-cEt

| SEQ ID NO./ ISIS NO. | Chemistry | Target | $IC_{50}$ (nM) Hepatocytes | HeLa cells |
|---|---|---|---|---|
| 18/529100 | 5'-(E)-PO(OH)$_2$CH=CH— | FVII | 2 | — |
| 19/457867 | 5-10-5 MOE Gapmer | FVII | 3 | — |
| 20/457851 | 2-10-2 (S)-cEt Gapmer | FVII | 4 | — |
| 21/529107 | 2'-F or 2'-OH | FVII | >200 | — |
| 22/533828 | 5'-(E)-PO(OH)$_2$CH=CH | eIF4E | — | 8 |
| 23/183750 | 5-10-5 MOE Gapmer | eIF4E | — | 3 |
| X1/529943 | 5'-(E)-PO(OH)$_2$CH=CH— | X | 2 | — |
| X2/533855 | 5'-(E)-PO(OH)$_2$CH=CH— | X | 7 | — |
| X3/147764 | 5-10-5 MOE Gapmer | X | 5 | — |

| SEQ ID NO./ ISIS NO. | Composition (5' to 3') |
|---|---|
| 18/529100 | PV-T$_{es}$U$_{fs}$A$_m$A$_{fs}$G$_m$A$_{fs}$C$_m$U$_{fs}$U$_m$G$_{fs}$A$_m$G$_{fs}$A$_m$U$_{fs}$G$_{ms}$A$_{fs}$U$_{ms}$C$_{fs}$C$_{ms}$A$_{es}$A$_e$ |
| 19/457867 | G$_{es}$A$_{es}$$^{me}$C$_{es}$$^{me}$C$_{es}$$^{me}$C$_{es}$T$_{ds}$G$_{ds}$G$_{ds}$T$_{ds}$G$_{ds}$T$_{ds}$A$_{ds}$$^{me}$C$_{ds}$A$_{ds}$$^{me}$C$_{es}$$^{me}$C$_{es}$$^{me}$C$_{es}$A$_{es}$A$_e$ |
| 20/457851 | $^{me}$C$_{ks}$$^{me}$C$_{ks}$T$_{ds}$G$_{ds}$G$_{ds}$T$_{ds}$G$_{ds}$T$_{ds}$A$_{ds}$$^{me}$C$_{ds}$A$_{ds}$$^{me}$C$_{ds}$$^{me}$C$_{ks}$$^{me}$C$_k$ |
| 21/529107 | G,U,A,A,G,A,C,U,U,G,A,G,A,U,G,A,U,C,C,T$_{ds}$T$_d$ |
| 22/533828 | PV-T$_{es}$C$_{fs}$U$_m$U$_{fs}$A$_m$U$_{fs}$C$_m$A$_{fs}$C$_m$C$_{fs}$U$_m$U$_{fs}$U$_m$A$_{fs}$G$_{ms}$C$_{fs}$U$_{ms}$C$_{fs}$U$_{ms}$A$_{es}$A$_e$ |
| 23/183750 | T$_{es}$G$_{es}$T$_{es}$$^{me}$C$_{es}$A$_{es}$T$_{ds}$A$_{ds}$T$_{ds}$T$_{ds}$$^{me}$C$_{ds}$$^{me}$C$_{ds}$T$_{ds}$G$_{ds}$G$_{ds}$A$_{ds}$T$_{es}$$^{me}$C$_{es}$$^{me}$C$_{es}$T$_{es}$T$_e$ |
| X1/XXXXXX | Pv-N$_{es}$N$_{fs}$N$_m$N$_{fs}$N$_m$N$_{fs}$N$_m$N$_{fs}$N$_m$N$_{fs}$N$_m$N$_{fs}$N$_m$N$_{fs}$N$_{ms}$N$_{fs}$N$_{ms}$N$_{fs}$N$_{ms}$N$_{es}$N$_e$ |
| X2/XXXXXX | Pv-N$_{es}$N$_{fs}$N$_m$N$_{fs}$N$_m$N$_{fs}$N$_m$N$_{fs}$N$_m$N$_{fs}$N$_m$N$_{fs}$N$_m$N$_{fs}$N$_{ms}$N$_{fs}$N$_{ms}$N$_{fs}$N$_{ms}$N$_{es}$N$_e$ |
| X3/XXXXXX | N$_{es}$N$_{es}$N$_{es}$N$_{es}$N$_{es}$N$_{ds}$N$_{ds}$N$_{ds}$N$_{ds}$N$_{ds}$N$_{ds}$N$_{ds}$N$_{ds}$N$_{ds}$N$_{ds}$N$_{es}$N$_{es}$N$_{es}$N$_{es}$N$_e$ |

Example 47

Evaluation of the Stability of Modified ssRNAs—In Vivo Study

The stability of modified ssRNAs can be evaluated in vivo using the procedures as described herein. Liver tissues were harvested and collected on ice from BALB/C mice treated with modified ssRNAs. 100-200 mg samples were minced and homogenized in 400 μL homogenization buffer (20 mM Tris, pH 8, 20 mM EDTA, 0.1 M NaCl, 0.5% NP-40). A standard curve ranging from 1 μg-75 μg was prepared for each ssRNA in 500 μL aliquots of control liver homogenate (400 μg/mL) with 10 μg internal standard (SEQ ID NO: 24, Isis NO: 355868, a 27-mer, 2'-O-methoxyethyl-modified phosphorothioate oligonucleotide). Tissue homogenates were then extracted using phenol/chloroform and solid support phase extraction techniques as described below with 300 μL $NH_4OH$ and 800 μL phenol/chloroform/isoamyl alcohol used in the phenol/chloroform extraction.

Phenol/Chloroform Extraction

Stability of ssRNAs was evaluated at time points 0, 5, 10, 20, 30, 40 and 60 minutes, except for SEQ ID NO: 25, Isis NO: 408877 which was evaluated at time points 0, 15, 30, 60, 120 and 240 mins; and SEQ ID NO: 25, Isis NO: 409044, at time points 0, 0.5, 1, 2, 4, 8, and 18 hours. An internal standard (SEQ ID NO: 24, Isis NO: 355868, a 27-mer, 2'-O-methoxyethyl-modified phosphorothioate oligonucleotide) with final concentration of 2.5 μM was added to each sample prior to extraction. Samples were extracted with 70 μL of $NH_4OH$ and 240 μL of phenol/chloroform/isoamyl alcohol (25:24:1). The supernatant was removed after centrifugation at 14000 rpm for 2 min. The remaining extractant was vortexed with an additional 500 μL of water and the aqueous layer was removed and combined with the supernatant after centrifugation at 14000 rpm for 2 minutes.

Solid Phase Extraction

Triethylammonium acetate solution at 1M (500 μL) was added to the supernatant. The aqueous layer of the mixture was loaded onto the pre-conditioned Biotage™ Phenyl Solid Phase Extraction Plate (SPE plate) after centrifugation at 9000 rpm for 20 minutes. The SPE plate was washed several times with water. The sample was then eluted with 1.5 mL of 1% TEA in 90% MeOH and filtered through the Protein Precipitation Plate (Phenomenex™). The eluent was evaporated to dryness and diluted to 200 μL with 50% quenching buffer (8 M urea, 50 mM EDTA) and water before sample injection.

LC-MS

An Agilent 1100 Series LC/MSD system was connected in-line to a mass spectrometer. Mass spectrometer was operated in the electrospray negative ionization mode. The nebulizer nitrogen gas was set at 325 psi and the drying nitrogen gas was set at 12 L/min. The drying temperature was 325° C. Samples (25 μL/well) were introduced via an auto sampler and reversed-phase chromatography was carried out with an) (Bridge OST C18 2.5 μm 2.1 mm×50 mm HPLC column using a flow rate of 300 μL/min at 55° C. The ion pair buffers consisted of A: 5mM tributylammonium acetate (TBAA) in 20% acetonitrile and B: 5 mM TBAA in 90% acetonitrile and the loading buffer was 25 mM TBAA in 25% Acetonitrile. Separation was performed on a 30% to 70% B in 9 min and then 80% B in 11 min gradient.

Quantitative analysis of oligonucleotide and internal standard by extracted ion chromatograms of the most abundant ions was performed using MSD ChemStation software.

Example 48

Modified ssRNAs Targeting PTEN—Multiple Dose In Vivo Study

Six week old BALB/C mice (Jackson Laboratory, Bar Harbor, Me.) were injected subcutaneously twice a day for two days at dosage 25 mg/kg (100 mg total) or twice a day for five days at dosage 30 mg/kg (300 mg total) with the modified single stranded oligomeric compounds targeted to PTEN from Example 43 shown below or with saline control. A 5-10-5 gapped oligomer having 2'-O-MOE modified nucleosides in wings (116847) was also included for comparison. The mice were sacrificed 48 hrs following last administration. Liver tissues were homogenized and mRNA levels were quantitated using real-time PCR as described herein for comparison to untreated control levels (% UTC). The results are listed as the average % of PTEN mRNA expression for each treatment group relative to saline-injected control. Additional analysis that were performed in such in vivo studies included plasma chemistries, liver and kidney weights, along with liver, kidney and spleen tissues from animals treated with the modified ssRNAs. Liver transaminase levels, alanine aminotranferase (ALT) and aspartate aminotransferase (AST), in serum were also measured relative to saline injected mice and the results are presented below.

| SEQ ID NO./ ISIS NO. | Chemistry | dosage (mg/kg total) | % UTC | ALT | AST |
|---|---|---|---|---|---|
| saline | | 0 | 100 | 22.8 | 53 |
| 05/505739 | 5'-(E)-PO(OH)$_2$CH=CH— | 300 | 75.4 | 20.8 | 71.5 |
| 06/522247 | 5'-(E)-PO(OH)$_2$CH=CH— | 300 | 35.8 | 19 | 97 |
| 06/508016 | 5'-PO(OH)$_2$(CH$_2$CH$_2$)— | 300 | 63.5 | 20.8 | 60.8 |
| 07/508015 | 5'-PO(OH)$_2$(CH$_2$CH$_2$)— | 300 | 82.3 | 30.5 | 111 |
| 07/522246 | 5'-(E)-PO(OH)$_2$CH=CH— | 300 | 44.5 | 32.3 | 98 |
| 06/522247 | 5'-(E)-PO(OH)$_2$CH=CH— | 100 | 63.9 | 21.3 | 102.5 |
| 07/522246 | 5'-(E)-PO(OH)$_2$CH=CH— | 100 | 81.2 | 23.3 | 87.3 |
| 13/116847 | 5-10-5 MOE Gapmer | 100 | 15.3 | 27 | 88.3 |

ALT and AST levels and kidney and liver weights were within normal limits for the animals treated with modified single stranded oligomeric compounds relative to saline-treated control. Histopathology report also showed no abnormality from liver, kidney and spleen for the animals treated with the oligomeric compounds.

Example 49

Stability of Modified ssRNAs Targeting PTEN: Multiple Dose In Vivo Study

The modified ssRNAs in Example 48 were evaluated for in vivo stability using the procedures as described in Example 47. Six week old BALB/C mice (Jackson Laboratory, Bar Harbor, Me.) were injected subcutaneously twice a day for two days at dosage 25 mg/kg (100 mg total) or twice a day for five days at dosage 30 mg/kg (300 mg total) with the modified ssRNAs targeted to PTEN shown below. A 5-10-5 gapped oligomer having 2'-O-MOE modified nucleosides in wings (116847) was also included for comparison. The mice were sacrificed 48 hrs following last administration.

Quantitative analysis of the oligonucleotides standard were performed by extracted ion chromatograms in the most abundant charge state (−4) using Chemstation software. The liver concentration (μg/g) of full length modified ssRNAs comprising a 5'-terminal phosphonate group was measured by LC/MS and the results are provided below.

| SEQ ID NO./ ISIS NO. | Chemistry | dosage (mg/kg total) | Liver conc. (µg/g) of full length ssRNA |
|---|---|---|---|
| 05/505739 | 5'-(E)-PO(OH)$_2$CH=CH— | 300 | 187 |
| 06/522247 | 5'-(E)-PO(OH)$_2$CH=CH— | 300 | 223 |
| 06/508016 | 5'-(E)-PO(OH)$_2$CH$_2$CH$_2$— | 300 | 187 |
| 07/508015 | 5'-(E)-PO(OH)$_2$CH$_2$CH$_2$— | 300 | 211 |
| 07/522246 | 5'-(E)-PO(OH)$_2$CH=CH— | 300 | 389 |
| 06/522247 | 5'-(E)-PO(OH)$_2$CH=CH— | 100 | 145 |
| 07/522246 | 5'-(E)-PO(OH)$_2$CH=CH— | 100 | 74 |
| 13/116847 | 5-10-5 MOE Gapmer | 100 | 190 |

Example 50

Modified ssRNAs targeting TTEN—In Vivo Dose Response Study

Six week old BALB/C mice (Jackson Laboratory, Bar Harbor, ME) were injected subcutaneously twice a day for one, two, four or six days at dosage 25 mg/kg with the modified single stranded oligomeric compound (522247) targeted to PTEN. A 5-10-5 gapped oligomer having 2'-O-MOE modified nucleosides in wings (116847) was also included for comparison. The mice were sacrificed 48 hrs following last administration. Liver tissues were homogenized and mRNA levels were quantitated using real-time PCR and normalized to RIBOGREEN™ as described herein for comparison to untreated control levels (% UTC). The results are listed as the average % of PTEN mRNA expression for each treatment group relative to saline-injected control.

| SEQ ID NO./ ISIS NO. | Chemistry | Day(s) | dosage (mg/kg total) | % UTC | ALT |
|---|---|---|---|---|---|
| saline | | 0 | 0 | 100 | 29.3 |
| 06/522247 | 5'-(E)-PO(OH)$_2$CH=CH— | 1 | 50 | 64.6 | 30.5 |
| 06/522247 | 5'-(E)-PO(OH)$_2$CH=CH— | 2 | 100 | 51.1 | 25.8 |
| 06/522247 | 5'-(E)-PO(OH)$_2$CH=CH— | 4 | 200 | 39.6 | 25.5 |
| 06/522247 | 5'-(E)-PO(OH)$_2$CH=CH— | 6 | 300 | 36.8 | 30.2 |
| 13/116847 | 5-10-5 MOE Gapmer | 2 | 100 | 13.82 | 35.5 |

ALT levels, liver, kidney, spleen and body weights were within the normal limits in animals treated with the modified single stranded oligomeric compound relative to saline-treated control.

Example 51

Modified ssRNAs targeting TVII—In Vivo Dose Response and Stability Studies

Six week old BALB/C mice (Jackson Laboratory, Bar Harbor, Me.) were injected subcutaneously with the modified single stranded oligomeric compounds targeted to FVII twice a day for one, two or four days at dosage 25 mg/kg (529100) or 5 mg/kg (457869). The mice were sacrificed 48 hrs following last administration. Liver tissues were homogenized and mRNA levels were quantitated using real-time PCR and normalized to Cyclophilin as described herein for comparison to untreated control levels (% UTC). The results are listed as the average % of PTEN mRNA expression for each treatment group relative to saline-injected control.

The modified ssRNAs were also evaluated for in vivo stability using the procedures as described in Example 47. Quantitative analysis of the oligonucleotides standard were performed by extracted ion chromatograms in the most abundant charge state (−4) using Chemstation software. The liver concentration (µg/g) of full length modified ssRNAs comprising a 5'-terminal phosphonate group was measured by LC/MS and the results are provided below.

| SEQ ID NO./ ISIS NO. | Composition (5' to 3') |
|---|---|
| 18/529100 | Pv-T$_{es}$U$_{fs}$A$_m$A$_{fs}$G$_m$A$_{fs}$C$_m$U$_{fs}$U$_m$G$_{fs}$A$_m$G$_{fs}$A$_m$U$_{fs}$G$_{ms}$A$_{fs}$U$_{ms}$C$_{fs}$C$_{ms}$A$_{es}$A$_e$ |
| 26/457869 | G$_{es}$T$_{es}$A$_{es}$$^{me}$C$_{es}$G$_{es}$$^{me}$C$_{ds}$T$_{ds}$T$_{ds}$G$_{ds}$G$_{ds}$T$_{ds}$$^{me}$C$_{ds}$$^{me}$C$_{ds}$$^{me}$C$_{ds}$T$_{ds}$A$_{es}$$^{me}$C$_{es}$A$_{es}$T$_{es}$G$_e$ |

A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, (PO(OH)$_2$(CH=CH—). $^{me}$C indicates a 5-methyl cytosine nucleoside. Nucleosides followed by a subscript "d" are β-D-2'-deoxyribonucleosides. Nucleosides followed by a subscript f, m or e are sugar modified nucleosides. A subscript "f' indicates a 2'-fluoro modified nucleoside, a subscript "m" indicates a 2'-O-methyl modified nucleoside and a subscript "e" indicates a 2'-O-methoxyethyl (MOE) modified nucleoside.

| SEQ ID NO./ ISIS NO. | Chemistry | dosage (mg/kg total) | % UTC | Liver conc. (µg/g) of full length ssRNA |
|---|---|---|---|---|
| saline | | 0 | 100 | — |
| 18/529100 | 5'-(E)-PO(OH)$_2$CH=CH— | 50 | 96.4 | 61 |
| 18/529100 | 5'-(E)-PO(OH)$_2$CH=CH— | 100 | 82.9 | 117 |
| 18/529100 | 5'-(E)-PO(OH)$_2$CH=CH— | 300 | 64.93 | 318 |
| 26/457869 | 5-10-5 MOE Gapmer | 10 | 59.5 | 39 |
| 26/457869 | 5-10-5 MOE Gapmer | 20 | 28 | 88 |
| 26/457869 | 5-10-5 MOE Gapmer | 40 | 7.0 | 145. |

Example 52

Modified ssRNAs Targeted to Target X—In Vivo Multiple Dose and Stability Studies Six week old BALB/C mice (Jackson Laboratory, Bar Harbor, Me.) were injected subcutaneously twice a day for six days at dosage 25 mg/kg (300 mg total) or twice a day for two days at dosage 25 mg/kg (100 mg total) with the modified single stranded oligomeric compounds targeted to Target X from Example 46 or with saline control. The mice were sacrificed 48 hrs following last administration. Liver tissues were homogenized and mRNA levels were quantitated using real-time PCR and normalized to Cyclophilin as described herein for comparison to untreated control levels (% UTC). The results are listed as the average % of Target X mRNA expression for each treatment group relative to saline-injected control.

The modified ssRNAs were also evaluated for in vivo stability using the procedures as described in Example 47. Quantitative analysis of the oligonucleotides standard were performed by extracted ion chromatograms in the most abundant charge state (−4) using Chemstation software. The liver concentration (μg/g) of full length modified ssRNAs comprising the 5′-terminal phosphonate group was measured by LC/MS and the results are provided below.

| SEQ ID NO./ ISIS NO. | Chemistry | dosage (mg/kg) | % UTC | Liver conc. (μg/g) |
|---|---|---|---|---|
| saline | | 0 | 100 | — |
| X1/XXXXXX | 5′-(E)-PO(OH)$_2$CH=CH— | 300 | 34.1 | 451 |
| X3/XXXXXX | 5-10-5 MOE | 100 | 11.3 | 94. |

---

What is claimed is:

1. A compound having Formula Ic:

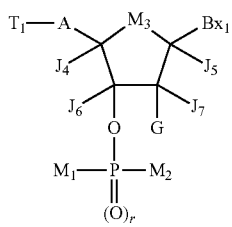

Ic wherein:

$T_1$ is phosphorus moiety having the formula:

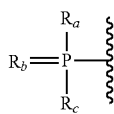

$R_a$ and $R_c$ are each, independently, protected hydroxyl, protected thiol, $C_1$-$C_6$ alkyl, substituted $C_1$-$C_6$ alkyl, substituted $C_1$-$C_6$ alkoxy, protected amino or substituted amino;

$R_b$ is O or S;

$M_1$ is H, OH or $OR_1$;

$M_2$ is OH, $OR_1$ or $N(R_1)(R_2)$;

each $R_1$ and $R_2$ is, independently, $C_1$-$C_6$ alkyl or substituted $C_1$-$C_6$ alkyl;

r is 0 or 1;

A has one of the formulas:

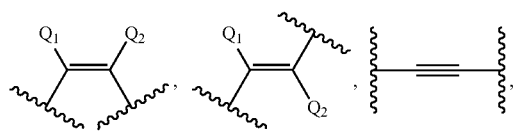

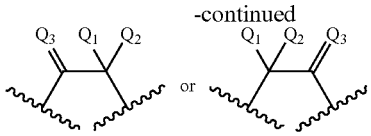

$Q_1$ and $Q_2$ are each, independently, H, halogen, $C_1$-$C_6$ alkyl or substituted $C_1$-$C_6$ alkyl;

$M_3$ is O;

$Bx_1$ is a heterocyclic base moiety;

$J_4$, $J_5$, $J_6$ and $J_7$ are each, independently, H;

G is H, OH, halogen or O-$[C(R_8)(R_9)]_n$-$[(C{=}O)_m$-$X_1]_j$-Z;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, ${=}NJ_1$, $SJ_1$, $N_3$, CN, $OC({=}X_2)J_1$, $OC({=}X_2)$ -$N(J_1)(J_2)$ and $C({=}X_2)N(J_1)(J_2)$;

$X_2$ is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

2. The compound of claim 1 wherein A has the formula:

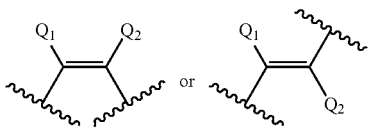

wherein:

Q1 and Q2 are each, independently, H, halogen, $C_1$-$C_6$ alkyl, substituted $C_1$-$C_6$ alkyl, $C_1$-$C_6$ alkoxy or substituted $C_1$-$C_6$ alkoxy.

3. The compound of claim 2 wherein $Q_1$ and $Q_2$ are each H.

4. The compound of claim 1 wherein G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$-CH=$CH_2$, $O(CH_2)_2$-$OCH_3$, $O(CH_2)_2$-$SCH_3$, $O(CH_2)_2$-$OCF_3$, $O(CH_2)_3$-$N(R_{10})(R_{11})$, $O(CH_2)_2$-$ON(R_{10})(R_{11})$, $O(CH_2)_2$-$O(CH_2)_2$-$N(R_{10})(R_{11})$, $OCH_2C(=O)$-$N(R_{10})(R_{11})$, $OCH_2C(=O)$-$N(R_{12})$-$(CH_2)_2$-$N(R_{10})(R_{11})$ or $O(CH_2)_2$-$N(R_{12})$-$C(=NR_{13})[N(R_{10})(R_{11})]$ wherein $R_{10}$, $R_{11}$, $R_{12}$ and $R_{13}$ are each, independently, H or $C_1$-$C_6$ alkyl.

5. The compound of claim 4 wherein said heterocyclic base moiety is a pyrimidine, substituted pyrimidine, purine or substituted purine.

6. The compound of claim 5 wherein said heterocyclic base moiety is uracil, thymine, cytosine, 5-methylcytosine, adenine or guanine.

7. An oligomeric compound comprising a 5'-terminal compound having Formula IIc:

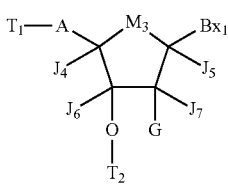

IIc wherein:
$T_1$ is an optionally protected phosphorus moiety having the formula:

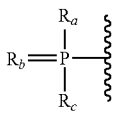

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino;

$R_b$ is O or S;

$T_2$ is an internucleoside linking group linking the compound of Formula IIc to the oligomeric compound;

A has one of the formulas:

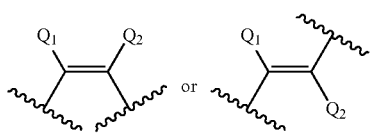

$Q_1$ and $Q_2$ are each, independently, H, halogen, $C_1$-$C_6$ alkyl or substituted $C_1$-$C_6$ alkyl;

$M_3$ is O;

$Bx_1$ is a heterocyclic base moiety;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O-$[C(R_8)(R_9)]_n$-$[(C=O)_m$-$X_1]_j$-Z;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, =$NJ_1$, $SJ_1$, $N_3$, CN, $OC(=X_2)J_1$, $OC(=X_2)$ -$N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

8. The oligomeric compound of claim 7 wherein A has the formula:

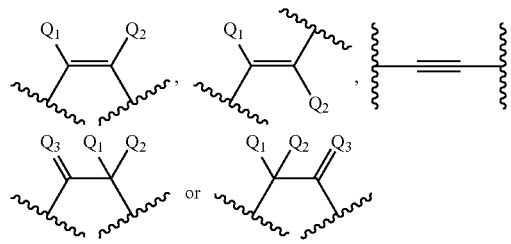

wherein:
$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy.

9. The oligomeric compound of claim 8 wherein $Q_1$ and $Q_2$ are each H.

10. The oligomeric compound of claim 7 wherein $R_b$ is O and $R_a$ and $R_c$ are each, independently, $OCH_3$, $OCH_2CH_3$ or $OCH(CH_3)_2$.

11. The oligomeric compound of claim 7 wherein G is halogen, $OCH_3$, $OCH_2F$, $OCHF_2$, $OCF_3$, $OCH_2CH_3$, $O(CH_2)_2$ F, $OCH_2CHF_2$, $OCH_2CF_3$, $OCH_2$-CH=$CH_2$, $O(CH_2)_2$-$OCH_3$, $O(CH_2)_2$-$SCH_3$, $O(CH_2)_2$-$OCF_3$, $O(CH_2)_3$-$N(R_{10})(R_{11})$, $O(CH_2)_2$-$ON(R_{10})(R_{11})$, $O(CH_2)_2$-$O(CH_2)_2$-$N(R_{10})(R_{11})$, $OCH_2C(=O)$-$N(R_{10})(R_{11})$, $OCH_2C(=O)$-$N(R_{12})$-$(CH_2)_2$-$N(R_{10})(R_{11})$ or $O(CH_2)_2$-$N(R_{12})$-$C(=NR_{13})[N(R_{10})(R_{11})]$ wherein $R_{10}$, $R_{11}$, $R_{12}$ and $R_{13}$ are each, independently, H or $C_1$-$C_6$ alkyl.

12. The oligomeric compound of claim 7 wherein said heterocyclic base moiety is a pyrimidine, substituted pyrimidine, purine or substituted purine.

13. The oligomeric compound of claim 12 wherein said heterocyclic base moiety is uracil, thymine, cytosine, 5-methylcytosine, adenine or guanine.

14. The oligomeric compound of claim 7 wherein said 5'-terminal compound has Formula IIe:

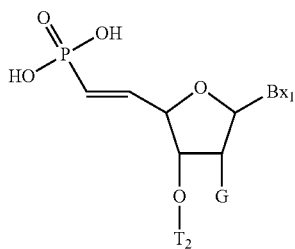

wherein:

Bx$_1$ is uracil, thymine, cytosine, 5-methyl cytosine, adenine or guanine;

T$_2$ is a phosphorothioate internucleoside linking group linking the compound of Formula IIe to the oligomeric compound; and G is halogen, OCH$_3$, OCF$_3$, OCH$_2$CH$_3$, OCH$_2$CF$_3$, OCH$_2$-CH=CH$_2$, O(CH$_2$)$_2$-OCH$_3$, O(CH$_2$)$_2$-O(CH$_2$)$_2$-N(CH$_3$)$_2$, OCH$_2$C(=O)-N(H)CH$_3$, OCH$_2$C(=O)-N(H)-(CH$_2$)$_2$-N(CH$_3$)$_2$ or OCH$_2$-N(H)-C(=NH)NH$_2$.

15. The oligomeric compound of claim 7 wherein each internucleo-side linking group is, independently, a phosphodiester internucleoside linking group or a phosphorothioate internucleoside linking group.

16. A double stranded composition comprising:
a first oligomeric compound and a second oligomeric compound wherein the first oligomeric compound is complementary to the second oligomeric compound and the second oligomeric compound is complementary to a nucleic acid target;
at least one of the first and second oligomeric compounds is an oligomeric compound according to claim 7; and
wherein said composition optionally comprises one or more 5' or 3' terminal groups.

17. A method of inhibiting gene expression comprising contacting a cell with an oligomeric compound of claim 7 wherein said oligomeric compound comprises from about 8 to about 40 monomeric subunits and is complementary to a target RNA.

18. The oligomeric compound of claim 1 wherein R$_b$ is O and R$_a$ and R$_c$ are each, independently, OCH$_3$.

19. The oligomeric compound of claim 7 wherein R$_b$ is O and R$_a$ and R$_c$ are each, independently, OH.

* * * * *

UNITED STATES PATENT AND TRADEMARK OFFICE
CERTIFICATE OF CORRECTION

PATENT NO. : 8,993,738 B2
APPLICATION NO. : 13/642827
DATED : March 31, 2015
INVENTOR(S) : Prakash et al.

It is certified that error appears in the above-identified patent and that said Letters Patent is hereby corrected as shown below:

In the Claims

Claim 1, column 159, line 59, to column 160, line 29, delete

"A has one of the formulas:

insert

--A has one of the formulas:

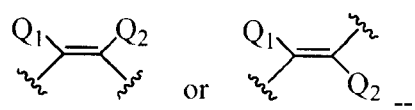 --

Claim 2, column 160, lines 55 to 63, delete

"The compound of claim 1 wherein A has the formula:

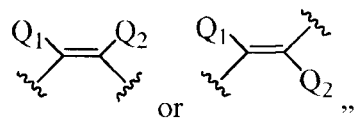 "

insert

--The compound of claim 1 wherein A has the formula:

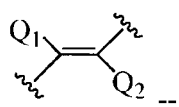 --

Signed and Sealed this
First Day of September, 2015

Michelle K. Lee
*Director of the United States Patent and Trademark Office*

Claim 8, column 162, lines 25 to 39, delete
"The oligomeric compound of claim 7 wherein A has the formula:
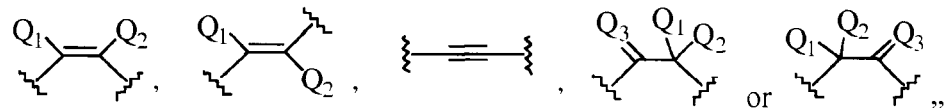
insert
--The oligomeric compound of claim 7 wherein A has the formula:
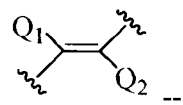 --